United States Patent [19]

Hester, Jr. et al.

[11] Patent Number: 4,880,781

[45] Date of Patent: Nov. 14, 1989

[54] RENIN INHIBITORY PEPTIDES CONTAINING AN N-ALKYL-HISTIDINE MOIETY

[75] Inventors: Jackson B. Hester, Jr., Galesburg; Suvit Thaisrivongs, Portage; Tomi K. Sawyer; Ruth E. TenBrink, both of Kalamazoo, all of Mich.; Hossain H. Saneii, Louisville, Ky.; Heinrich J. Schostarez; Donald T. Pals, both of Portage, Mich.

[73] Assignee: The Upjohn Company, Kalamazoo, Mich.

[21] Appl. No.: 147,073

[22] Filed: Jan. 20, 1988

Related U.S. Application Data

[63] Continuation-in-part of Ser. No. 753,198, Jul. 9, 1985, abandoned, which is a continuation-in-part of Ser. No. 693,320, Jan. 22, 1985, abandoned, which is a continuation-in-part of Ser. No. 663,028, Oct. 19, 1984, abandoned, which is a continuation-in-part of Ser. No. 663,024, Oct. 19, 1984, abandoned, which is a continuation-in-part of Ser. No. 663,027, Oct. 19, 1984, abandoned, which is a continuation-in-part of Ser. No. 663,023, Oct. 19, 1984, abandoned, which is a continuation-in-part of Ser. No. 663,026, Oct. 19, 1984, abandoned, which is a continuation-in-part of Ser. No. 663,093, Oct. 19, 1984, abandoned, which is a continuation-in-part of Ser. No. 638,027, Aug. 6, 1984, abandoned, which is a continuation-in-part of Ser. No. 638,041, Aug. 6, 1984, abandoned, which is a continuation-in-part of Ser. No. 638,025, Aug. 6, 1984, abandoned, which is a continuation-in-part of Ser. No. 38,023, Aug. 6, 1984, abandoned, which is a continuation-in-part of Ser. No. 638,024, Aug. 6, 1984, abandoned, which is a continuation-in-part of Ser. No. 638,026, Aug. 6, 1984, abandoned.

[51] Int. Cl.$^4$ .................. A61K 37/43; C07K 7/06; C07K 5/08; C07K 5/10; C07K 5/06
[52] U.S. Cl. .................................. 514/18; 514/19; 514/400; 530/330; 530/331; 530/328; 548/344
[58] Field of Search .............. 514/18, 19, 400; 530/330, 331, 328; 548/344

[56] References Cited

U.S. PATENT DOCUMENTS

| | | | |
|---|---|---|---|
| 4,242,256 | 12/1980 | Sharpe et al. | 530/328 |
| 4,297,346 | 10/1981 | Rips et al. | 514/19 |
| 4,424,207 | 1/1984 | Szelke et al. | 424/177 |
| 4,470,971 | 9/1984 | Boger et al. | 424/177 |
| 4,477,440 | 10/1984 | Boger et al. | 424/177 |
| 4,477,441 | 10/1984 | Boger et al. | 424/177 |
| 4,478,826 | 10/1984 | Veber et al. | 424/177 |
| 4,478,827 | 10/1984 | Haber et al. | 424/177 |
| 4,479,941 | 10/1984 | Verber et al. | 424/177 |
| 4,485,099 | 11/1984 | Boger et al. | 424/177 |
| 4,511,504 | 4/1985 | McCullagh et al. | 560/29 |

FOREIGN PATENT DOCUMENTS

| | | |
|---|---|---|
| 0045161 | 2/1982 | European Pat. Off. |
| 0045665 | 2/1982 | European Pat. Off. |
| 0053017 | 2/1982 | European Pat. Off. |
| 0077028 | 4/1983 | European Pat. Off. |
| 0077029 | 4/1983 | European Pat. Off. |
| 0081783 | 6/1983 | European Pat. Off. |
| 0104041 | 3/1984 | European Pat. Off. |
| 0111266 | 6/1984 | European Pat. Off. |
| 0114993 | 6/1984 | European Pat. Off. |
| 0118223 | 9/1984 | European Pat. Off. |
| 2621279 | 11/1977 | Fed. Rep. of Germany ...... 530/328 |

OTHER PUBLICATIONS

Derwent Abstr. 156322, 3/27/84.
Derwent Abstr. 172346, 3/22/84.
Derwent Abstr. 163237, 5/29/84.
Derwent Abstr. 156321, 3/27/84.
Derwent Abstr. 172347, 6/22/84.
Derwent Abstr. WO/8403044, 2/7/83.
Synthetic Peptides, vol. 6 (1984), 224, 225, 240, 241, 266.
Holladay et al., "Synthesis of Hydroxyethylene and Ketomethylene Dipeptide Isosteres", vol. 24, No. 41, pp. 4401-4404, 1983.

*Primary Examiner*—Delbert R. Phillips
*Attorney, Agent, or Firm*—Lawrence T. Welch

[57] ABSTRACT

The present invention provides novel renin-inhibiting peptides and novel processes and intermediates for the preparation of both novel and known renin-inhibiting peptide analogs. Such inhibitors are useful for the diagnosis and control of renin-dependent hypertension.

29 Claims, No Drawings

RENIN INHIBITORY PEPTIDES CONTAINING AN N-ALKYL-HISTIDINE MOIETY

CROSS REFERENCE TO RELATED APPLICATIONS

This application is a continuation-in-part of application Ser. No. 753,198, filed 9 July 1985, abandoned, which is a continuation-in-part of application Ser. No. 693,320, filed 22 Jan. 1985, abandoned; Ser. Nos. 663,028, abandoned; 663,024, abandoned; 663,027, abandoned; 663,023; 663,026, abandoned; and 663,093, abandoned; all filed 19 Oct. 1984, and Ser. Nos. 638,027, abandoned; 638,041, abandoned; 638,025, abandoned; 638,023, abandoned; 638,024, abandoned; and 638,026, abandoned; all filed 6 Aug. 1984.

BACKGROUND OF THE INVENTION

The present invention provides novel compounds. More particularly, the present invention provides novel renin-inhibiting peptide analogs. Additionally, the invention herein provides novel intermediates for the preparation of novel renin-inhibiting peptides and novel processes for the preparation of the intermediates and both novel and known renin-inhibiting peptide analogs. Unexpectedly advantageous novel peptide analogs are also the present invention. The renin inhibitors provided herein are useful for the diagnosis and control of renin-dependent hypertension.

Renin is an endopeptidase which specifically cleaves a particular peptide bond of its substrate (angiotensinogen), of which the N-terminal sequence in equine substrate is for example:

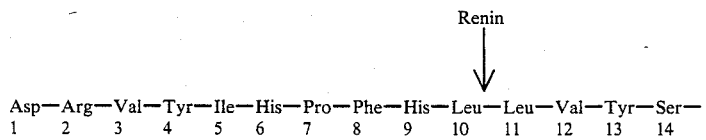

Asp—Arg—Val—Tyr—Ile—His—Pro—Phe—His—Leu—Leu—Val—Tyr—Ser—
1     2    3    4   5    6    7    8    9    10   11   12   13  14

IA as found by L. T. Skeggs et al, J. Exper. Med. 106, 439 (1957). Human renin substrate has a different sequence as recently discovered by D. A. Tewkesbury et al, Biochem. Biophys. Res. Comm. 99, 1311 (1981). It may be represented as follows:

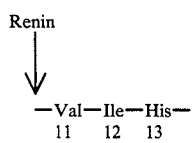

—Val—Ile—His—
  11   12  13

IB and having the sequence to the left of the arrow ($\downarrow$) being as designated in formula IA as above.

Renin cleaves angiotensinogen to produce angiotensin I, which is converted to the potent pressor angiotensin II. A number of angiotensin I converting enzyme inhibitors are known to be useful in the treatment of hypertension. Inhibitors of renin are also useful in the treatment of hypertension.

INFORMATION DISCLOSURE

A number of renin-inhibitory peptides have been disclosed. Thus, U.S. Pat. No. 4,424,207, and European published applications 45,665 and 104,041 disclose certain peptides with the dipeptide at the 10,11-position containing an isostere bond. A number of statine derivatives stated to be renin inhibitors have been disclosed, see, e.g., European published applications 77,028; 81,783; and 114,993; and U.S. Pat. Nos. 4,478,826; 4,470,971 and 4,479,941. Terminal disulfide cycles have also been disclosed in renin inhibiting peptides; see, e.g., U.S. Pat. Nos. 4,477,440 and 4,477,441. Aromatic and aliphatic amino acid residues at the 10,11 position of the renin substrate are disclosed in U.S. Pat. No. 4,478,827. C-terminal amide cycles are disclosed in U.S. Pat. No. 4,485,099. Certain tetrapeptides are disclosed in European publications 111,266 and 77,029. Further, European published application No. 118,223, which was published after the instant invention was made, discloses certain renin inhibiting peptide analogs where the 10-11 peptide link is replaced by a one to four atom carbon of carbon-nitrogen link. Additionally, Holladay et al., in "Synthesis of Hydroxyethylene and Ketomethylene Dipeptide Isosteres", Tetrahedron Letters, Vol. 24, No. 41, pp. 4401–4404, 1983 disclose various intermediates in a process to prepare stereo-directed "ketomethylene" and "hydroxyethylene" dipeptide isosteric functional groups disclosed in the above noted U.S. Pat. No. 4,424,207.

Additionally, published European Applications 45,161 and 53,017 disclose amide derivatives useful as inhibitors of angiotensin converting enzymes.

SUMMARY OF THE INVENTION

The present invention particularly provides a renin inhibitory peptide of the formula X—$A_6$—$B_7$—$C_8$—$D_9$—$E_{10}$—$F_{11}$—$G_{12}$—$H_{13}$—$I_{14}$—Z, wherein X is
(a) hydrogen,
(b) $C_1$-$C_5$alkyl
(c) $R_5$—O—$CH_2$—C(O)—,
(d) $R_5$—$CH_2$—O—C(O)—,
(e) $R_5$—O—C(O)—,
(f) $R_5$—$(CH_2)_n$—C(O)—,
(g) $R_4N(R_4)$—$(CH_2)_n$—C(O),
(h) $R_5$—$SO_2$—$(CH_2)_q$—C(O)—, or
(i) $R_5$—$SO_2$—$(CH_2)_q$—O—C(O)—;

wherein $A_6$ is absent or a divalent moiety of the formula $XL_1$, $XL_2$, or $XL_{2a}$ wherein $B_7$ is absent or a divalent moiety of the formula $XL_b$ wherein $C_8$ is absent or a divalent moiety of the formula $XL_1$, $XL_2$ or $XL_{2a}$, wherein $D_9$ is absent or a divalent moiety of the formula $XL_3$, or $XL_{2a}$, wherein $E_{10}$-$F_{11}$ is a divalent moiety of the formula $XL_6$, $XL_{6a}$, $XL_{6b}$, $XL_{6c}$, $XL_{6d}$, or $XL_{6e}$, wherein * indicates an asymmetric center which is either in the R or S configuration;

wherein $G_{12}$ is absent or a divalent moiety of the formula $XL_4$ or $XL_{4a}$ wherein $H_{13}$ is absent or a divalent moiety of the formula $XL_4$ wherein $I_{14}$ is absent or a divalent moiety of the formula $XL_5$ wherein Z is (a) —O—$R_{10}$,
(b) —N($R_4$)$R_{14}$, or
(c) $C_4$-$C_8$cyclic amino;
wherein R is
(a) isopropyl,
(b) isobutyl,
(c) phenylmethyl, or
(d) $C_3$-$C_7$cycloalkyl;
wherein $R_1$ is
(a) hydrogen,
(b) $C_1$-$C_5$alkyl,
(c) aryl,
(d) $C_3$-$C_7$cycloalkyl,
(e) —Het,
(f) $C_1$-$C_3$alkoxy, or
(g) $C_1$-$C_3$alkylthio;
wherein $R_2$ is
(a) hydrogen, or
(b) —CH($R_3$)$R_4$;
wherein $R_3$ is
(a) hydrogen,
(b) hydroxy,
(c) $C_1$-$C_5$alkyl,
(d) $C_3$-$C_7$cycloalkyl,
(e) aryl,
(f) —Het,
(g) $C_1$-$C_3$alkoxy, or
(h) $C_1$-$C_3$alkylthio;
wherein $R_4$ at each occurrence is the same or different and is
(a) hydrogen, or
(b) $C_1$-$C_5$alkyl;
wherein $R_5$ is
(a) $C_1$-$C_6$alkyl,
(b) $C_3$-$C_7$cycloalkyl,
(c) aryl,
(d) —Het, or
(e) 5-oxo-2-pyrrolidinyl;
wherein $R_6$ is
(a) hydrogen,
(b) $C_1$-$C_5$alkyl,
(c) —(CH$_2$)$_p$-aryl,
(d) —(CH)$_{2p}$—Het,
(e) $C_3$-$C_7$cycloalkyl, or
(f) 1- or 1-adamantyl;
wherein $R_7$ is
(a) hydrogen,
(b) $C_1$-$C_5$alkyl,
(c) hydroxy,
(d) amino $C_1$-$C_4$alkyl-,
(e) guanidinyl $C_1$-$C_3$alkyl-,
(f) aryl,
(g) —Het,
(h) methylthio,
(i) $C_3$-$C_7$cycloalkyl, or
(j) amino;
wherein $R_8$ is
(a) hydrogen,
(b) $C_1$-$C_5$alkyl,
(c) hydroxy,
(d) aryl,
(e) —Het,
(f) guanidinyl $C_1$-$C_3$alkyl-, or
(g) $C_3$-$C_7$cycloalkyl;
wherein $R_9$ is
(a) hydrogen,
(b) hydroxy,
(c) amino $C_1$-$C_4$alkyl-, or
(d) guanidinyl $C_1$-$C_3$alkyl-;
wherein $R_{10}$ is
(a) hydrogen,
(b) $C_1$-$C_5$alkyl,
(c) —(CH$_2$)$_n$$R_{16}$,
(d) —(CH$_2$)$_n$$R_{17}$,
(e) $C_3$-$C_7$cycloalkyl,
(f) a pharmaceutically acceptable cation,
(g) —(CHR$_{25}$)—CH$_2$—$R_{15}$, or
(h) —CH$_2$—(CHR$_{12}$)—$R_{15}$;
wherein $R_{11}$ is —R or —$R_2$;
wherein $R_{12}$ is —(CH$_2$)$_n$—$R_{13}$;
wherein $R_{13}$ is
(a) aryl,
(b) amino,
(c) mono-, di or tri-$C_1$-$C_3$alkylamino,
(d) —Het,
(e) $C_1$-$C_5$alkyl
(f) $C_3$-$C_7$cycloalkyl,
(g) $C_1$-$C_5$alkenyl,
(h) $C_3$-$C_7$cycloalkenyl,
(i) hydroxy,
(j) $C_1$-$C_3$alkoxy,
(k) $C_1$-$C_3$alkanoyloxy,
(l) mercapto,
(m) $C_1$-$C_3$alkylthio,
(n) —COOH,
(o) —CO—O—$C_1$-$C_6$alkyl,
(p) —CO—O—CH$_2$—($C_1$-$C_3$alkyl)—N($C_1$-$C_3$alkyl)$_2$,
(q) —CO—NR$_{22}$R$_{26}$;
(r) $C_4$-$C_7$cyclic amino,
(s) $C_4$-$C_7$cycloalkylamino,
(t) guanidyl,
(u) cyano,
(v) N-cyanoguanidyl,
(w) cyanoamino,
(x) (hydroxy $C_2$-$C_4$alkyl)amino, or
(y) di-(hydroxy$C_2$-$C_4$alkyl)amino;
wherein $R_{14}$ is
(a) hydrogen,
(b) $C_1$-$C_{10}$alkyl,
(c) —(CH$_2$)$_n$—$R_{18}$,
(d) —(CH$_2$)$_n$—$R_{19}$,
(e) —(CHR$_{25}$)—CH$_2$—$R_{15}$,
(f) —CH$_2$—(CHR$_{12}$)—$R_{15}$,
(g) (hydroxy $C_1$-$C_8$alkyl), or
(h) ($C_1$-$C_3$alkoxy)$C_1$-$C_8$alkyl;
wherein $R_{15}$ is
(a) hydroxy,
(b) $C_3$-$C_7$cycloalkyl,
(c) aryl,
(d) amino,
(e) mono-, di-, or tri- $C_1$-$C_3$alkylamino,
(f) mono- or di-[hydroxy $C_2$-$C_4$alkyl]amino,
(g) —Het,
(h) $C_1$-$C_3$alkoxy-
(i) $C_1$-$C_3$alkanoyloxy-,
(j) mercapto,
(k) $C_1$-$C_3$alkylthio-,
(l) $C_1$-$C_5$alkyl,
(m) $C_4$-$C_7$cyclic amino,
(n) $C_4$-$C_7$cycloalkylamino,
(o) $C_1$-$C_5$alkenyloxy,
(p) $C_3$-$C_7$cycloalkenyl;
wherein $R_{16}$ is
(a) aryl,
(b) amino, (c) mono- or di- $C_1$-$C_3$alkylamino,
(d) hydroxy,
(e) $C_3$-$C_7$cycloalkyl,
(f) $C_4$-$C_7$cyclic amino, or
(g) $C_1$-$C_3$alkanoyloxy;
wherein $R_{17}$ is
 (a) —Het,
 (b) $C_1$-$C_5$alkenyl,
 (c) $C_3$-$C_7$cycloalkenyl,
 (d) $C_1$-$C_3$alkoxy,
 (e) mercapto,
 (f) $C_1$-$C_3$alkylthio,
 (g) —COOH,
 (h) —CO—O—$C_1$-$C_6$alkyl,
 (i) —CO—O—$CH_2$—($C_1$-$C_3$alkyl)—N($C_1$-$C_3$alkyl)$_2$,
 (j) —CO—NR$_{22}$R$_{26}$,
 (k) tri-$C_1$-$C_3$alkylamino,
 (l) guanidyl,
 (m) cyano,
 (n) N-cyanoguanidyl,
 (o) (hydroxy $C_2$-$C_4$alkyl)amino, or
 (p) di-(hydroxy $C_2$-$C_4$alkyl)amino;
wherein $R_{18}$ is
 (a) amino,
 (b) mono-, or di- $C_1$-$C_3$alkylamino, or
 (c) $C_4$-$C_7$cyclic amino;
wherein $R_{19}$ is
 (a) aryl,
 (b) —Het,
 (c) tri-$C_1$-$C_3$alkylamino,
 (d) $C_3$-$C_7$cycloalkyl,
 (e) $C_1$-$C_5$alkenyl,
 (f) $C_3$-$C_7$cycloalkenyl,
 (g) hydroxy,
 (h) $C_1$-$C_3$alkoxy,
 (i) $C_1$-$C_3$alkanoyloxy,
 (j) mercapto,
 (k) $C_1$-$C_3$alkylthio,
 (l) —COOH,
 (m) —CO—O—$C_1$-$C_6$alkyl,
 (n) —CO—O—$CH_2$—($C_1$-$C_3$alkyl)—N($C_1$-$C_3$alkyl)$_2$,
 (o) —CO—NR$_{26}$R$_{22}$,
 (p) $C_4$-$C_7$cycloalkylamino,
 (q) guanidyl,
 (r) cyano,
 (s) N-cyanoguanidyl,
 (t) cyanoamino,
 (u) (hydroxy $C_2$-$C_4$alkyl)amino,
 (v) di-(hydroxy $C_2$-$C_4$alkyl)amino; or
 (w) —SO$_3$H;
wherein $R_{20}$ is
 (a) hydrogen,
 (b) $C_1$-$C_5$alkyl, or
 (c) aryl-$C_1$-$C_5$alkyl;
wherein $R_{21}$ is
 (a) —NH$_2$, or
 (b) —OH;
wherein $R_{22}$ is
 (a) hydrogen, or
 (b) $C_1$-$C_3$alkyl;
wherein $R_{23}$ is
 (a) —(CH$_2$)$_n$—OH,
 (b) —(CH$_2$)$_n$—NH$_2$,
 (c) aryl, or
 (d) $C_1$-$C_3$alkyl;
wherein $R_{24}$ is
 (a) —R$_1$,
 (b) —(CH$_2$)$_n$—OH, or
 (c) —(CH$_2$)$_n$—NH$_2$;
wherein $R_{25}$ is —(CH$_2$)$_n$—R$_{13}$;
wherein $R_{26}$ is
 (a) hydrogen,
 (b) $C_1$-$C_3$alkyl, or
 (c) phenyl-$C_1$-$C_3$alkyl;
wherein m is one or two:
wherein for each occurrence n is independently an integer of zero to five, inclusive;
wherein p is zero to 2 inclusive;
wherein q is 1 to 5, inclusive;
wherein Q is
 (a) —CH$_2$—,
 (b) —CH(OH)—,
 (c) —O—, or
 (d) —S—; and
wherein M is
 (a) —CO—, or
 (b) —CH$_2$—;
wherein aryl is phenyl or naphthyl substituted by zero to 3 to the following:
 (a) $C_1$-$C_3$alkyl,
 (b) hydroxy,
 (c) $C_1$-$C_3$alkoxy,
 (d) halo,
 (e) amino,
 (f) mono- or di-$C_1$-$C_3$alkylamino,
 (g) —CHO,
 (h) —COOH,
 (i) COOR$_{26}$,
 (j) CONHR$_{26}$,
 (k) nitro,
 (l) mercapto,
 (m) $C_1$-$C_3$alkylthio,
 (n) $C_1$-$C_3$alkylsulfinyl,
 (o) $C_1$-$C_3$alkylsulfonyl,
 (p) —N(R$_4$)—$C_1$-$C_3$alkylsulfonyl,
 (q) SO$_3$H,
 (r) SO$_2$NH$_2$,
 (s) —CN, or
 (t) —CH$_2$NH$_2$;
wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
 (i) $C_1$-$C_6$alkyl,
 (ii) hydroxy,
 (iii) trifluoromethyl,
 (iv) $C_1$-$C_4$alkoxy,
 (v) halo,
 (vi) aryl,
 (vii) aryl $C_1$-$C_4$alkyl-,
 (viii) amino, and
 (ix) mono- or di-$C_1$-$C_4$alkylamino;
with the overall provisos that
(1) $E_{10}$-$F_{11}$ is $XL_{6a}$, $XL_{6b}$, $XL_{6c}$, $XL_{6d}$, or $XL_{6e}$ only when
 (a) at least one of the following occurs:
  (i) $A_6$ is present and
   (A) $A_6$ is $XL_1$ or
   (B) $A_6$ is $XL_2$ wherein $R_6$ is Het which is $N^{in}$formul-Trp, (ii) $B_7$ is present and $R_4$ of $B_7$ is other than hydrogen,
(iii) $C_8$ is present and is $XL_1$,
(iv) $D_9$ is $N_\alpha$-methyl-histidine;
(v) $B_7$ and $C_8$ both are present and $B_7$ and $XL^b$ wherein M is $-CH_2-$ and $C_8$ is $XL_1$; or
(vi) X is $R_5-SO_2-(CH_2)_q-C(O)-$ or $R_5-SO_2-C(CH_2)_q-O-C(O)-$;

(b) $B_7$ and $C_8$ both are present and $B_7$ is $XL^b$ wherein M is $-CH_2-$ and $C_8$ is $XL_1$;

(2) $E_{10}F_{11}$ is $XL_{6e}$ only when $G_{12}$, $H_{13}$ and $I_{14}$ are absent;

(3) $B_7C_8D_9$ is Pro-Phe-His, $E_{10}F_{11}$ is $CL_6$, $R_1$ is isopropyl, or isobutyl; and $R_{11}$ is isopropyl, isobutyl, or benzyl, only when one of the following occurs:
(a) all of $G_{12}$, $H_{13}$, and $I_{14}$ are present;
(b) only 1 of $G_{12}$, $H_{13}$, and $I_{14}$ is present;
(c) $G_{12}$ is other than D or L val or D or L Ile;
(d) $H_{13}I_{14}$ is other than D or L Tyr, D or L Phe, or D or L His; or
(e) $A_6$ is FTrp or $XL_1$;

(4) $R_{16}$ or $R_{17}$ is an amino-containing substituent, hydroxy, mercapto, or —Het bonded through the hetero atom only when n for that substituent is an integer from two to five, inclusive;

(5) $R_{18}$ or $R_{19}$ is hydroxy, mercapto, or amino, or a mono-substituted nitrogen containing group bonded through the nitrogen only when n is not one;

(6) $A_6$, $B_7$, $C_8$, $H_{13}$ and $I_{14}$ are all absent, $D_9$ and $G_{12}$ are both present, and $-NR_4-$ of $D_9$ is $-NH-$ and Z is $-OR_{10}$ and $R_{10}$ is hydrogen, $C_1$-$C_5$alkyl, or $-(CH_2)_m-R_{16}$ or Z is $-N(R_4)R_{14}$ and $R_{14}$ is hydrogen, $C_1$-$C_{10}$alkyl or $-(CH_2)_n-R_{18}$, or Z is $C_4$-$C_8$cyclic amino, only when $R_5-(CH_2)_n-$ is other than $C_1$-$C_8$alkyl, $C_5$-$C_7$cycloalkyl or aryl;

(7) $A_6$, $B_7$, $C_8$, $D_9$, $H_{13}$, $I_{14}$ are all absent and $G_{12}$ is present only when Z is $-OR_{10}$ or $R_{10}$ is $-(CH_2)_n-R_{17}$, $-(CHR_{25})-CH_2R_{15}$ or $-CH_2-(CHR_{12})-R_{15}$ or when Z is $-N(R_4)R_{14}$ and $R_{14}$ is $-(CH_2)_n-R_{19}$, $-(CHR_{25})-CH_2R_{15}$, or $-CH_2-(CHR_{12})-R_{15}$;

(8) $R_{12}$ is $-(CH_2)_n-R_{13}$ and n is zero and both $R_{13}$ and $R_{15}$ are oxygen-, nitrogen-, or sulfur-containing substituents bonded through the hetero atom, only when the hetero atom is not also bonded to hydrogen;

(9) when $R_{12}$ is $-(CH_2)_n-R_{13}$ and n is zero, then $R_{13}$ and $R_{15}$ cannot both be $-COOH$;

(10) $R_{25}$ is $-(CH_2)_n-R_{13}$ and n is zero only when $R_{13}$ is other than a primary or secondary nitrogen-containing group hydroxy or mercapto group or when $R_4$ of $-N(R_4)R_{14}$ is other than hydrogen;

(11) Z is $C_4$-$C_8$cyclic amino, only when at least one of $G_{12}$, $H_{13}$, and $I_{14}$ is present;

(12) $R_{17}$ or $R_{19}$ is —Het, only when —Het is other than cyclic amino;

(13) $R_{17}$ or $R_{19}$ is —COOH only when n for that moiety is other than zero; and

(14) at least one of $A_6$, $B_7$, $C_8$, $D_9$, $G_{12}$, $H_{13}$ or $I_{14}$ must be present; or a carboxy-, amino-, or other reactive group-protected form or a pharmaceutically acceptable acid addition salt thereof.

These compounds are shown in relation to the human renin substrate as follows:

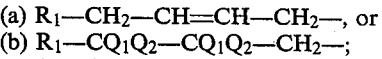

| | 6 | 7 | 8 | 9 | 10 | 11 | 12 | 13 | |
|---|---|---|---|---|---|---|---|---|---|
| | —His | Pro | Phe | His | Leu | Val | Ile | His— | |
| X | $A_6$ | $B_7$ | $C_8$ | $D_9$ | $E_{10}$ | $F_{11}$ | $G_{12}$ | $H_{13}$ | $I_{14}$ | Z, |

The present invention further provides novel intermediates used for the preparation of these renin-inhibiting compounds.

Thus, the present invention provides:
(1) a compound of the formula I-1
wherein T is
(a) $R_1-CH_2-CH=CH-CH_2-$, or
(b) $R_1-CQ_1Q_2-CQ_1Q_2-CH_2-$;
wherein R is
(a) isopropyl,
(b) isobutyl,
(c) phenylmethyl, or
(d) $C_3$-$C_7$cycloalkyl;
wherein $R_1$ is
(a) hydrogen,
(b) $C_1$-$C_5$alkyl,
(c) aryl,
(d) $C_3$-$C_7$cycloalkyl,
(e) —Het,
(f) $C_1$-$C_3$alkoxy, or
(g) $C_1$-$C_3$alkylthio;
wherein $Q_1$ and $Q_2$ are different and are hydrogen or hydroxy; including all isomers thereof;

(2) a compound of the formula I-2 where the configuration at the asymmetric center* is either R or S;
wherein R is
(a) isopropyl,
(b) isobutyl,
(c) phenylmethyl, or
(d) $C_3$-$C_7$cycloalkyl;
wherein $R_1$ is
(a) hydrogen,
(b) $C_1$-$C_5$alkyl,
(c) aryl,
(d) $C_3$-$C_7$cycloalkyl,
(e) —Het,
(f) $C_1$-$C_3$alkoxy, or
(g) $C_1$-$C_3$alkylthio;
wherein $R_2$ is
(a) hydrogen or
(b) $-CH(R_3)R_4$;
wherein $R_3$ is
(a) hydrogen,
(b) hydroxy,
(c) $C_1$-$C_5$alkyl,
(d) $C_3$-$C_7$cycloalkyl,
(e) aryl,
(f) —Het,
(g) $C_1$-$C_3$alkoxy, or
(h) $C_1$-$C_3$alkylthio;
wherein $R_4$ at each occurrence is the same or different and is
(a) hydrogen, or
(b) $C_1$-$C_5$alkyl; and
wherein TBDMS is t-butyldimethysilyl;

(3) a compound of the formula I-3
wherein R is
(a) isopropyl,
(b) isobutyl,
(c) phenylmethyl, or
(d) $C_3$-$C_7$cycloalkyl; and
wherein $R_1$ is (a) hydrogen,
(b) $C_1$-$C_5$alkyl,
(c) aryl,
(d) $C_3$-$C_7$cycloalkyl,
(e) —Het,
(f) $C_1$-$C_3$alkoxy, or
(g) $C_1$-$C_3$alkylthio,
wherein $R_{110}$ is H or t-butoxycarbonyl and wherein $R_{111}$ is OH or a protecting group;
(4) and a compound of the formula I-4
wherein L is
(a) H, OH, or
(b) $\alpha$-NHBOC, $\beta$-H;
wherein BOC is t-butoxycarbonyl;
wherein R is
(a) isopropyl,
(b) isobutyl,
(c) phenylmethyl, or
(d) $C_3$-$C_7$cycloalkyl; and
wherein $R_2$ is
(a) hydrogen, or
(b) —$CHR_3(R_4)$;
wherein $R_3$ is
(a) hydrogen,
(b) hydroxy,
(c) $C_1$-$C_5$alkyl,
(d) $C_3$-$C_7$cycloalkyl,
(e) aryl,
(f) —Het,
(g) $C_1$-$C_3$alkoxy, or
(h) $C_1$-$C_3$alkylthio;
wherein $R_4$ at each occurrence is the same or different and is
(a) hydrogen, or
(b) $C_1$-$C_5$alkyl;
(c) aryl,
(d) $C_3$-$C_7$cycloalkyl,
(e) —Het,
(f) $C_1$-$C_3$alkoxy, or
(g) $C_1$-$C_3$alkylthio;
wherein $R_{11}$ is R or $R_2$.

Additionally, the present invention provides:
(a) a process for preparing a compound of the formula I which comprises
  (1) treating a compound having the formula XIVA/B (see, e.g., steps VIIIA and IXA of Chart D, Scheme IIIA) wherein R, $R_1$ and BOC are as defined above; with an alkali metal hydroxide in the presence of dilute acetonitrile in water;
  (2) treating the product of step (1) with t-butyldimethylsilyl chloride in the presence of imidazole in dimethylformamide; and then
  (3) hydrolyzing selectively the t-butyldimethylsilyl ester of step (2) and acidifying to obtain the compound I-3 wherein $R_{110}$ is —OH;
(b) a process for preparing a compound of the formula (XIVA/B) where the configuration at the asymmetric center* is either R or S; and wherein R, $R_1$ and BOC are as defined above (see, e.g., Steps VIA and VIIA of Chart D, Scheme IIIA); which comprises
  (1) reducing a compound having the formula XIIA/B where the configuration at the asymmetric center* is either R or S, and R and $R_1$ are as defined above; with aluminum amalgam or hydrogen in the presence of a hydrogenation catalyst to produce a compound of the formula XIVA; and
  (2) treating the product of step (1) with di-t-butylcarbonate to obtain the compound of formula XIVA/B.
(c) a process for preparing a compound of the formula XIIA/B where the configuration at the symmetric center* is either R or S, and wherein R and $R_1$ are as defined above (see, e.g., Steps XB and XIB of Chart C, Scheme IIIB); which comprises
  (1) reacting a compound having the formula XB/C where the configuration at the asymmetric center* is either R or S, and wherein R and $R_1$ are as defined above, with omethanesulfonyl chloride in the presence of triethylamine in dichloromethane; and
  (2) reacting the product of step (1) with an alkali metal azide to obtain the compound of formula XIIA/B;
(d) a process for the preparation of a compound having the formula XIIA/B where the configuration at the asymmetric center* is either R or S, and wherein R and $R_1$ are as defined above (see, e.g., Steps IVA and VA of Chart D, Scheme IIIA); which comprises
  (1) reacting a compound having the formula XA/D where the configuration at the asymmetric center* is either R or S, and wherein R and $R_1$ are as defined above; with a phosphorus-containing halogenating reagent; and
  (2) reacting the product of step (1) with an alkali metal azide to obtain the compound of formula XIIA/B;
(e) a process for preparing a compound of the formula AX/B/C/D where the configuration at the asymmetric center* is either R or S; and wherein R and $R_1$ are as defined above (see, e.g., Step IIIA, Chart D, Scheme IIIA); which comprises
  (1) treating a compound having the formula IX-A/B/C/D where the configuration at the asymmetric center* is either R or S, and wherein R and $R_1$ are as defined above; with an acid to obtain the corresponding compound of formula XA/B/C/D;
(f) a process for preparing a compound of the formula IXC/D wherein R and $R_1$ are as defined above, and $Q_1$ and $Q_2$ are different and are hydrogen or hydroxy (see, e.g., Step IIB of Chart F, scheme IIID/D); which comprises treating a compound having the formula VIIIB wherein R and $R_1$ are as defined above; with a tertiary amine oxide in the presence of osmium tetroxide to obtain the compound having the formula IXC/D;
(g) a process for preparing a compound of the formula IXA/B wherein R, $R_1$, $Q_1$ and $Q_2$ are as defined above (see, e.g., Step IIA, Chart C, Scheme IIIA/B); which comprises treating a compound having the formula VIIIA where R and $R_1$ are as defined above; with a tertiary amine oxide in the presence of osmium tetroxide to obtain the compound of formula IXA/B;
(h) a process for preparing a compound of the formula VIIIB wherein R and $R_1$ are as defined above (see, e.g., Step IB, Chart F, Scheme C/D); which comprises
  (1) treating a compound of formula II wherein R is as defined above with lithium diisopropylamide, then then adding hexamethylphosphoramide to the reaction mixture, and (2) aklylating the product of step (2) with a compound having the formula VII wherein $R_1$ is as defined above to obtain a compound of a formula VIIIB; and (i) a process for preparing a compound of the formula VIIIA wherein R and $R_1$ are as defined above (see, e.g., Step IA of Chart C, Scheme IIIA/B); which comprises (1) treating a compound having the formula II wherein R is as defined above; with lithium diisopropylamide, then adding hexamethylphosphoramide to the reaction mixture, and (2) alkylating with a compound having the formula V wherein $R_1$ is as defined above to obtain the compound of formula VIIIA.

Examples of pharmaceutically acceptable acid addition salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethansulfonate, fumarate, glucoheptanoate, glycerophosphate, hemisulfate, heptanoate, haxanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_4)$alkyl refers to alkyl of one to 4 carbon atoms, inclusive, or methyl, ethyl, propyl, butyl, and isomeric forms thereof. $C_4-C_7$cyclic amino indicates a monocyclic group containing one nitrogen and 3 to 7 carbon atoms.

Examples of $(C_3-C_{10})$cycloalkyl which include alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, cyclopentyl, 2,2-dimethylcyclopentyl, and cyclohexyl.

Examples of aryl include phenyl, naphthyl, (o-, m-, p-)tolyl, (o-,m-, p-) ethylphenyl, 2-ethyl-tolyl, 4-ethyl-o-tolyl, 5-ethyl-m-tolyl, (o-, m-, or p-) propylphenyl, 2-propyl-(o-, m-, or p-)tolyl, 4-isopropyl-2,6-xylyl, 3-propyl-4-ethylphenyl, (2,3,4- 2,3,6-, or 2,4,5-)trimethylphenyl, (o-, m-, or p-)fluorophenyl, (o-, m-, or p-trifluoromethyl)phenyl, 4-fluoro-2,5-xylyl, (2,4- 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-) chloro-2-fluorophenyl, (o-, m-, or p-)trifluoromethylphenyl, (o-, m-, ot p-)ethoxyphenyl, (4- or 5-)chloro-2-methoxyphenyl, and 2,4-dichloro(5- or 6-)methylphenyl.

Examples of —Het include: 2-, 3-, or 4-pyridyl, imidazolyl, indolyl, $N^{in}$-formyl-indolyl, $N^{in}$-$C_2$-$C_5$alkyl-C(O)-indolyl, [1,2,4]-triazolyl, 2-, 4-, 5-pyrimidinyl, 2-, 3-thienyl, piperdinyl, pyrryl, pyrrolinyl, pyrrolidinyl, pyrazolyl, pyrazolinyl, pyrazolindinyl, imidazolinyl, imidazolindinyl, pyrazinyl, piperazinyl, pyridazinyl, oxazolyl, oxazolindinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, thienyl, and benzothienyl. Each of these moieties may be substituted as noted above.

As would be generally recognized by those skilled in the art of organic chemistry, a heterocycle as defined herein for —Het would not be bonded through oxygen or sulfur or through nitrogen which is within a ring and part of a double bond.

Halo is halogen (fluoro, chloro, bromo, or iodo) or trifluoromethyl.

Examples of pharmaceutically acceptable cations include: pharmacologically acceptable metal cations, ammonium, amine cations, or quaternary ammonium cations. Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are also within the scope of this invention. Pharmacologically acceptable amine cations are those derived from primary, secondary, or tertiary amines.

The novel peptides herein contain both natural and synthetic amino acid residues. These residues are depicted using standard amino acid abbreviations (see, e.g., Roberts, et al., Basic Principles of Organic Chemistry, pp. 703-705 (New York 1965)) unless otherwise indicated.

All the renin-inhibiting compounds of the present invention may be administered in the conventional forms, such as disclosed in U.S. Pat. No. 4,424,207 which is incorporated by reference herein. Likewise, the amounts disclosed in the U.S. Pat. No. 4,424,207 are examples applicable to the compounds of the present invention.

Preferably, the dosages of the present invention are for oral administration for treatment of humans to effect renin inhibition for the purpose of favorably affecting blood pressure. For this purpose, the compounds are administered from 0.1 to 1000 mg per kg per dose, administered from 1 to 4 times daily. Equivalent dosages for other routes of administration are also employed.

The exact dose depends on the age, weight, and condition of the patient and on the frequency and route of administration. Such variations are within the skills of the practitioner or can readily be determined.

The compounds of the present invention may also be administered in association with known diuretic agents. An ordinarily skilled physician can readily determine when such concomitant therapy is appropriate.

The compounds of the present invention may be pharmaceutically acceptable salts both those which can be produced from the free bases by methods well known in the art and those with which acids have pharmacologically acceptable conjugate bases.

Surprisingly and unexpectedly, the compounds of the present invention are preferably administered in the form of pharmacologically acceptable acid addition salts. These salts retain their potent hypotensive activity when orally administered to both renin-infused rats and sodium depleted monkeys, as demonstrated by Examples B3 and B4 below. Preferred pharmacologically acceptable salts for oral administration include the citrate and aspartate salts, although any pharmacologically acceptable salt is useful in this invention, including those listed above. These salts may be in hydrated form.

In appropriate cases, micronization of the compounds of this invention may be advantageous for optimal drug delivery.

The compounds of the present invention are prepared as depicted in the charts and as described more fully in the Preparations and Examples.

The description below refers to the structures depicted on the formula page and in the Charts A–Q. In those formulas, all variables are as defined above except where noted.

Generally, the renin inhibiting polypeptides may be prepared by either polymer assisted or solution phase peptide synthetic procedures analogous to those described hereinafter or to those methods known in the art. For example, the carboxylic moiety of Nα-t-butyloxycarbonyl (Boc)-substituted amino acid derivatives having suitable side chain protecting groups, if necessary, may be condensed with the amino functionality of a suitably protected amino acid, peptide or polymer-bound peptide using a conventional coupling protocol such as dicyclohexylcarbodiimide (DCC) and 1-hydroxybenzotriazole (HOBT) in methylene chloride or dimethylformamide. The synthetic procedures used to incorporate the novel moieties herein are also described, for example, in U.S. Pat. Nos. 4,424,207; 4,470,971; 4,477,440; 4,477,441; 4,478,826; 4,478,827; 4,479,941; and 4,485,099, which are expressly incorporated by reference herein. See, also, published European patent applications Nos. 45,161; 45,665; 53,017; 77,028; 77,029; 81,783; 104,041; 111,266; 114,993; and 118,223.

Following coupling reaction completion, the Nα-Boc moiety may be selectively removed with 45% trifluoroacetic acid/2% anisole (v/v) in methylene chloride. Neutralization of the resultant trifluoroacetate salt may be accomplished with 10% diisopropylethylamine in methylene chloride. In the case of polymer-assisted peptide synthesis, this stepwise, coupling strategy may be partially or completely automated to provide the desired peptide-polymer intermediates. Anhydrous hydrofluoric acid treatment of the peptide-polymer intermediate may then be used to effect simultaneous protecting group removal and cleavage of the peptide from its polymeric support. A notable exception to this includes $N^{in}$-formyl-indolyl-substituted peptides in which the $N^{in}$formyl-indolyl moiety is stable to TFA or HF but may be removed by $NH_3$ or NaOH. Because FTrp is somewhat unstable to base in synthetic procedures, possibly causing lower yields, it may be desirable in solution phase synthesis to introduce the FTrp-containing moiety late in the synthetic sequence so that it is not exposed to such conditions.

The incorporation of $N^{in}$-formyl-Trp into compounds of the present invention is easily accomplished because of the commercial availability of Nα-Boc-$N^{in}$-formyl-Trp-OH. However, the $N^{in}$-formyl moiety may be introduced into indolyl-substituted amino acid derivatives or related compounds by reaction with HCl-formic acid as reported in the literature, see A. Previero et al, Biochim. Biophys. Acta 147,453 (1967); Y. C. S. Yang et al, Int. J. Peptide Protein Res. 15, 130 (1980).

The processes of (h) and (i) above, shown in Chart F, Scheme IIIC/D as (Step IB) and Chart C, Scheme IIIA/B (Step IA), respectively, for the preparation of a compound having the formula VIIIB and VIIIA, respectively; and the processes of (f) and (g) above, shown in Chart F, Scheme IIIC/D as (Step IIB) and Chart C, Scheme IIIA/B (Step IIA, respectively, for the preparation of a compound having the formula IXC/D and IXA/B, respectively, establish the asymmetric centers of the intermediates ($I_1$) and final novel and known renin-inhibiting peptide analogs.

That is, the (2S) stereochemistry is established by a stereoselective alkylation in Step I, and the relative stereochemistry at C-4 and C-5 is controlled by a cis-oxidation of either a trans (VIIIA) or cis (VIIIB) double bond in Step II. Further, all four of the possible isomers having the formula IXA, IXB, IXC, or IXD can be isolated, identified and manipulated to give the desired compounds of formula $I_1$ as shown in the Schemes III, i.e., A/B, C/D, A, B, C and D.

The processes of the invention also include a single step or combination of steps as shown in Schemes III, IV, V, VI, VII, VIII and IX, described above, for the preparation of the compounds therein.

Preparation of the compounds having the formula XX wherein $A_6$ or $C_8$ is $XL_1$ is accomplished by appropriate coupling with a compound having the formula $XX_1T$ wherein X, $R_4$ and $R_6$ are as defined above. The compound having the formula $XX_1T$ may be prepared by methods known in the art.

In all of the processes of the present invention, the starting materials are either known or can be prepared by known methods.

The differences and advantages of the present invention of intermediates and processes over the above references are readily apparent to one of skill in the art contemplating large scale production of the desired analogs disclosed in U.S. Pat. No. 4,424,207. For example, all the asymmetric centers* (designated with *) of the moiety $XL_6$ in the renin-inhibiting analogs are established in the first two steps of the synthesis of one of the novel compounds herein of the formula IXA/B or IXC/D wherein R and $R_1$ are as defined above, as shown in Scheme IIIA/B or IIIC/D, Steps I and II. That is, the 2(S) stereochemistry is established by a stereoselective alkylation in Step I. Then, the relative stereochemistry at C-4 and C-5 in the above noted compounds of formula IXA/B/C/D is controlled by a cis-oxidation in Step II or either a trans compound as shown in VIIIA or cis compound as shown in VIIIB relative to the double bond.

One of the completely unexpected advantages of the present invention is evident in Scheme III, either A or B, and particularly the Step VIII therein. Here the hydrolysis of the compounds XIVA/B wherein R, $R_1$ and BOC are as defined above, proceeds without racemization of the R bearing carbon. That this is unexpected can be seen if the compound XA/B, wherein R and $R_1$ are as defined above, is hydrolyzed. For example, by comparison, the alcohol of the lactone having the formula XA/B protected with a benzyl carbamate, hydrolyzes with the result that undesirable racemization of the R bearing carbon occurs.

Finally, all of the isomers IXA/B/C/D can be isolated, identified and manipulated to give the desired intermediates $I_1$ wherein R, $R_1$ and BOC are as defined above, and TBDMS is t-butyldimethylsilyl which intermediates $I_1$ can be incorporated into appropriate peptides as shown in U.S. Pat. No. 4,424,207 discussed above, as well as to make the novel isosteric peptides of the present invention.

In the incorporation of intermediate I into peptides, it is noteworthy that the TBDMS oxygen-protecting group on the compound of formula $I_1$ is unexpectedly not removed if a BOC nitrogen protecting group is present and removed with trifluoroacetic acid from the N terminal group. Such selective removal of the BOC protecting group is advantageous for simple coupling of the N of the formula $I_1$ to the carboxyl of other compounds using standard coupling conditions or as taught herein to the carboxyl of other peptides. Therefore, compounds of formula $I_1$ of the present invention having TBDMS as a protecting group are not obvious from the teachings in the prior art.

Generally, methods of alkylation useful in alkylating histidine for use in the present invention are found in Cheung, S. T. et al, Can. J. Chem., Vol 55, pp. 906-910 (1977). However, it is now found that in Cheung, S. T. et al methods it is critical that the reaction conditions for the alkylation of histidine by anhydrous. Further, it is now found also that during work-up instead of adding water directly to the reaction mixture, it is preferred that a buffered aqueous solution be added to the reaction mixture, for example, aqueous sodium or potassium hydrogen sulfate. Specifically, although this is not meant to be limiting, in the manner described in the reference, 5S-Amino-2S-isopropyl-7-methyl-4S-tert-butyldimethylsilyloxy-octanoyl-L-isoleucyl-2-pyridylmethylamide is converted to N-tert-Butyloxycarbonyl-N-methyl-N$^{im}$-tosyl-L-histidyl-5S-amino-2S-isopropyl-7-methyl-4S-tert-butyldimethylsilyloxy-octanoyl-L-isoleucyl-2-pyridylmethylamide, which is converted to N-Methyl-N$^{im}$-tosyl-L-histidyl-5S-amino-4S-hydroxy-2S-isopropyl-7-methyloctanoyl-L-isoleucyl-2-pyridylmethylamide, which is converted to N-tert-Butyloxycarbonyl-L-phenylalanyl-N-methyl-N$^{im}$-tosyl-L-histidyl-5S-amino-4S-hydroxy-2S-isopropyl-7-methyloctanoyl-L-isoleucyl-2-pyridylmethylamide; and N-tert-Butyloxycarbonyl-L-phenylalanyl-N-methyl-L-histidyl-5S-amino-4S-hydroxy-2S-isopropyl-7-methyl-octanoyl-L-isoleucyl-2-pyridylmethylamide.

In a similar manner, using appropriate starting materials, the following compound is prepared:

Boc—Pro—PheNMHis—LVA—IleAMP.

A more detailed description of this method is set forth in Preparation XX$_{20}$II$_1$ (C68) below. This example is analogous to that found in Cheung, S. T. et al, Can. J. Chem. Vol 55, pp. 906-910 (1977)), however, it has been found that the process requires anhydrous reaction conditions which are not taught by Cheung et al. The remaining compounds are prepared as described in Preparation XX$_{20}$IV (C70); Preparation XX$_{20}$VI$_3$ (C72); Preparation XX$_{20}$VI$_2$ (C73); Preparation XX$_2$VI$_1$ (C74); and Preparation XX$_{20}$VI (C75) below. See, also, U. N. Reinhold, J. Med. Chem. 11:258-260 (1968).

Variations in the above description for starting materials, reactants, reaction conditions and required protecting groups to obtain other such N-alkylated compounds are known to an ordinarily skilled chemist or are readily available in the literature.

Preferred compounds of this invention where D$_9$ contains N-alkylated histidine are Tba—Phe—NMHis—Leu—Ψ—[CHOHCH$_2$-]Val—Ile—AMP PGA—Phe—NMHis—Leu—Ψ—[CHOHCH$_2$-]Val—Ile—AMP Boc—FTrp—Pro—Phe—NMHis—Leu—Ψ—[-CHOHCH$_2$]Val—Ile—AMP POA—His—Leu—Val—Ile—AMP Boc—Phe—NMHis—LVA—MBA Boc—Phe—NMHis—LVA—IBA Ac—FTrp—Pro—Phe—NMHis—Sta—Ile—NH$_2$ Ac—FTrp—Pro—Phe—NMHis—PRP—NH$_2$ Ac—Pro—Phe—NMHis—PRP—NH$_2$ and Ac—Pro—Phe—NMHis—LVA—Ile—AMP.

Where a bracketed number appears next to a compound named below, physicochemical data is provided for that compound in TABLE B.

In addition to the above compounds prepared generally for alkylating the appropriate N, it is now unexpectedly found that enhanced enzymatic stability is provided by renin-inhibiting polypeptide analogues modified by a fragment wherein B$_7$ is XL$_b$ and R$_4$ is methyl.

Polypeptides of the present invention having this moiety include for example:

—α—Me—Pro—Phe—Phe—Sta—,

—α—Me—Pro—Phe—His—Sta—, and

—α—Me—Pro—Phe—His—Leu—Ψ—[CHOHCH$_2$]—Val—.

Preferred compounds are as follows:
(a) Boc—α—Me—Pro—Phe—Phe—Sta—Ile—AMP [165],
(b) Boc—α—Me—Pro—Phe—His—Sta—Ile—AMP [166],
(c) Boc—α—Me—Pro—Phe—His—Leu—Ψ—[CH$_2$NH]Val—Ile—AMP, and
(d) Boc—α—Me—Pro—Phe—His—Leu—Ψ—[-CHOHCH$_2$]Val—Ile—AMP [167].

Of these the most preferred is (d).

These α—Me—Pro containing compounds are prepared as exemplified in Preparations XX$_{30}$I$_7$ (C76) through XX$_{30}$I (C83) below. See also Seebach, D., et al., J. Am. Chem. Soc., Vol. 105, pp. 5390-5398 (1983).

The unexpectedly advantageous stability of these polypeptides results from the α-methyl group on the prolyl portion of the fragment.

Compounds containing B$_7$-C$_8$ as the moiety Proψ(CH$_2$O)Phe, i.e., where the —CO—NH moiety in ProPhe is replaced by —CH$_2$—O—(abbreviated PEP), are prepared as depicted in Charts P and Q. The requisite appropriately protected α-amino starting materials for the synthesis of compounds of this invention are known or are prepared using known methods. See, "The Peptides: Analyses, Synthesis, Biology", Vol. 1-5, Ed. E. Gross and J. Meienhofer, Academic Press, NY, 1979-1983; "Peptides: Synthesis-Physical Data", Vol. 1-6, ed. W. Voelter and E. Schmid-Siegmann, G. Addison-Wesley Publishing Co., Inc., Reading, Mass., 1983; "Chemistry and Biochemistry of Amino Acids, Peptides, and Proteins", Vols. 1-7, ed. B. Weinstein, Marcel Dekker, Inc., NY, 1971-1983; "The Practice of Peptide Synthesis", M. Bodanszky and A. Bodanszky, Springer-Verlag, Berlin, 1984; "Peptide Synthesis", 2nd ed., M.

Bodansky, Y. Klausner, and M. Ondetti, Wiley, NY, 1976.

In general, the amide bonds linking the individual amino acids are formed using a condensation such as N,N'-dicyclohexylcarbodimide (DCC) with or without an additive such as 1-hydroxybenzotriazole (1-HOBT) in solvents such as methylene chloride (CH$_2$Cl$_2$) and/or dimethylformamide (DMF). A general scheme illustrating the synthesis of a peptide of this invention containing PEP is described in Chart P, Scheme P-I.

These peptides may also be prepared by the standard solid phase techniques of Merrifield. Appropriate protecting groups, reagents, and solvents for both the solution and solid phase methods can be found in "The Peptides: Analysis, Synthesis, and Biology," Vols. 1–5, eds. E. Gross and T. Meienhofer, Academic Press, NY, 1979–1983.

The protected amino acid Boc—Pro$\psi$[CH$_2$O]-Phe—OH is prepared as shown in Chart Q Scheme Q-I. L-Prolinol is acylated with (R)-2-bromo-3-phyenylpropionic acid using DCC as the coupling agent and methylene chloride as the solvent. The resulting amide is treated with sodium hydride in tetrahydrofuran at 0°–10° to give the bicyclic lactone where each chiral center is one of the S configuration. Hydrolysis of the lactone with 6 N HCl at 100° affords the hydrochloric salt of the amino acid H—Pro$\psi$[CH$_2$O]Phe—OH.

The compounds of the present invention may be in either free form or in protected form at one or more of the remaining (not previously) protected) peptide, carboxyl, amino, hydroxy, or other reactive groups. The protecting groups may be any of those known in the polypeptide art. Examples of nitrogen and oxygen protection groups are set forth in T. W. Greene, Protecting Groups in Organic Synthesis, Wiley, New York, (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (Boc), benzyloxycarbonyl, acetyl, allyl, phthalyl, benzyl, benzoyl, trityl and the like. However, the need for variation of protective groups in the present invention may be limited, as described above, whereby the protective group's removal is selective as for BOC on the compound of formula I, relative to the TBDMS group which may be used to protect the hydroxy in the same compound. Thus, although the incorporation into selected peptides of an isosteric group which includes the unit of the present invention having the formula I$_1$ where the configuration at the asymmetric center* is either R or S, and R and R$_1$ are as defined above, was first accomplished in U.S. Pat. No. 4,424,207, the unexpected advantage of the compound I$_1$ to accomplish such incorporation is not evident from the above noted references. That is, compounds of formula I$_1$ are amenable to advantageous synthetic strategies for both polymer supported (U.S. Pat. No. 4,424,207—columns 11 through 17, under EXAMPLES) and solution peptide synthesis. They can be transformed into renin inhibitors of the present invention by standard methods known in the art. For example, the carboxylic acid moiety can be condensed with the amino terminus suitably protected amino acids or peptides using standard coupling conditions such as dicyclohexylcarbodiimide (DCC)/1-hydroxybenzotriazole (HOBT). The BOC protecting group of the resulting peptides can be selectively removed with 50% trifluoroacetic acid (TFA) CH$_2$Cl$_2$, and the resulting amino terminus condensed with the free carboxyl group of suitably protected amino acids or peptides again using standard coupling conditions. The resulting protected peptides are then deprotected using standard conditions for the protecting groups employed and, if necessary, using mild acid, 50% trifluoroacetic acid, (e.g., dilute acetic acid) or fluoride ion (e.g., HF or nBu$_4$N$^{30}$F$^-$) to remove the TBDMS alcohol protecting group. The choice of amino acids or peptides used for these condensations is based on the structure of the ultimate renin inhibitor desired. These may be as described in U.S. Pat. No. 4,424,207, but more preferred inhibitors are the novel inhibitors of the present invention.

In general, the processes of the present invention may be carried out in the following manner.

Amides of the formula II are prepared as shown in Chart A, Scheme I by acylating the L-2 pyrrolidinemethanol with an activated derivative of the appropriate acid. Activated derivatives useful in this reaction are the acid halides or anhydrides which can if desired be employed with an equivalent of a tertiary amine such as triethylamine, pyridine or p-dimethylaminopyridine to consume the acid generated in the reaction. Alternatively the acylation can be accomplished with condensing agents such as 1,1'-carbonyldiimidazole or dicyclohexylcarbodiimide. Aprotic solvents useful for this reaction include THF, DMF, dioxane ether, CH$_2$Cl$_2$ and pyridine. If selective acylation of the nitrogen is not successful the N,O-diacylated products are prepared as shown in Scheme I$_1$, and in a second step hydrolyzed with base, for example, sodium or potassium hydroxide as shown in Scheme I$_2$; in solvents such as ethanol, water, acetonitrile, to give the compounds of formula II.

The preparation of compounds having the formulas V and VII shown in Chart B, Scheme II is accomplished in a manner generally according to the description of the respective steps therein as follows:

Step I: Reduction of the acetylenic alcohols (III) to the (E) olefins (IV) is accomplished either by the reaction of an alkali metal (Na, Li) in liquid ammonia [A. J. Birch, Quarterly Reviews, IV, 69 (1950)] or by the reaction of an aluminum hydride, e.g. lithium aluminum hydride in a solvent such as diethylether, THF or dioxane.

Steps II and IV: The allylic alcohols are conveniently converted to the corresponding bromides, with rearrangement, by one of the phosphorus reagents, e.g. triphenylphosphine/carbon tetrabromide or triphenylphosphine/N-bromosuccinimide, or phosphorus tribromide. Solvents such as acetonitrile, methylene chloride or benzene are useful for those reactions.

Step III: The acetylenic alcohols (III) are conveniently reduced to the (Z)-alkenes (VI) with hydrogen and a modified palladium-on-calcium carbonate catalyst (Lindlar catalyst). Solvents such as methanol or ethanol are suitable for this reaction. Quinoline can be used to help control the selective reduction to the (Z)-olefin.

The starting material of formula III in Scheme II when R$_1$ is isopropyl may be obtained from the commercially available 4-methyl-1-pentyne by successive reactions with ethylmagnesium bromide and formaldehyde as shown in scheme II, using conditions appropriate for the reactions as generally known for analogous reactions.

However, the starting material of formula III wherein R₁ is phenyl may be prepared according to the procedures of W. J. Bailey and E. Fugiwara, J. Am. Chem. Soc. 77, 165 (1955); and G. Dupont, et al., Bull. Soc. Chim. France, 816 (1954) as illustrated by Scheme II₂.

Generally, for the reactions shown as various steps I through IX in Scheme III may be described in a manner applicable to each step having the same Roman numeral without regard to the letters A, B, C or D. The distinction among the compounds and, therefore, also among the steps which are denoted by the letters A, B, C or D, do not affect the conditions as described for the respective steps as follows:

Step I: The dianion of compound II is prepared at ambient temperature (18°-25° C. (bath temperature) in THF with two equivalents of lithium diisopropylamide. It is then treated with two equivalents of hexamethylphosphoramide cooled to −78° C. (bath temperature) and treated with the alkylating agent, either V or VII. This reaction is carried out essentially as described by D. A. Evans, et al., Tetrahedron Letters 21, 4233 (1980) and gives predominantly the (2S)-product.

Step II: Cis hydroxylation of the double bond is accomplished by an osmium tetroxide catalyzed oxidation using trimethylamine oxide as the oxidant. Other tertiary amine oxides such as N-methylmorpholine oxide can also be used for this purpose. Separation of isomers by column chromatography is accomplished at this stage.

Step III: The L-2-pyrrolidinemethanol amide of formula IX is hydrolyzed by an acid catalyzed N→O acyl transfer to give the lactones (X). A variety of mineral acids and aqueous solvents could also be used in this reaction.

Step IV: Conversion of the alcohol to a leaving group with inversion of stereochemistry is required. The phosphorus based reagents, for example, Ph₃P/CX₄, Ph₃P/Br₂, Ph₃P/NBS, and (Me₂N)₃P/CCl₄ are particularly suitable for this transformation. Solvents such as CCl₄ (excess), CH₂Cl₂, CH₃CN, PhH can be used. For a review, see B. R. Castro, Org. Reactions 29, 1 (1983).

Step V: The displacement is accomplished with one or more equivalents of an alkali metal azide (LiN₃, NaN₃, KN₃) in a solvent such as DMF or DMSO. Reaction temperatures of from 30° to 90° are required.

Step VI: Reduction of the azide can be accomplished with aluminum amalgam or preferably catalytic hydrogenation. A variety of catalysts such as Pd/C, PtO₂ or Raney Ni can be used. We used the modified palladium-on-calcium carbonate, Lindlar catalyst. Solvents such as methanol or ethanol are suitable.

Step VII: The amino group is converted to the t-butoxycarbonyl (BOC) derivative under standard conditions. Standard conditions include under nitrogen at ambient temperature for a time required to show by TLC or silica gel with 5% MeOH—CH₂Cl₂ using ninhydrin spray that the reaction is complete. It is allowed to react at 25° with di-t-butyl dicarbonate in a solvent such as THF or dioxane.

Step VIII: The lactone is hydrolyzed without epimerization with an alkali metal hydroxide in dilute acetonitrile-water. The resulting mixture can be concentrated and freeze dried to give the anhydrous alkali metal salt. Alternatively a cold aqueous solution of the salt can be acidified with dilute KHSO₄. The resulting acid can be isolated by filtration or extraction with a suitable solvent. Either the salt or the acid corresponding to compound XV can be used in Step IX.

Step IX: The reaction of compounds XV with t-butyldimethylsilyl chloride and imidazole in DMF at 25°, standard conditions for this reaction, gives the t-butyldimethylsilyl ether and ester. The ester is selectively hydrolyzed with K₂CO₃ in methanol and the resulting potassium salt is acidified with dilute KHSO₄ to give the acids (I).

Step X: The methanesulfonate (mesylate) derivatives of compounds XB and XC are prepared under standard conditions: methanesulfonyl chloride and triethylamine in CH₂Cl₂ at 0°.

Step XI: Conversion of the mesylates (XVIB and C) to the azides (XIIB and C) is accomplished in the same manner as step V.

Compounds of the present invention wherein E₁₀F₁₁ is LeuΨ(CH[OH]CH₂)Val (LVA) include

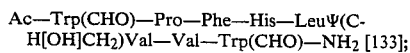

and

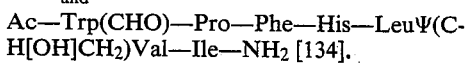

Compounds of the present invention wherein E₁₀F₁₁ is PheΨ(CH₂NH)Phe include

Ac—Trp(CHO)—Pro—Phe—His—PheΨ(CH₂NH)-Phe—Val—Trp(CHO)—NH₂ [135],

Ac—Trp(CHO)—Pro—Phe—His—PheΨ(CH₂NH)-Phe—Val—Tyr—NH₂ [136],

Ac—Trp(CHO)—Pro—Phe—His—PheΨ(CH₂NH)-Phe—Val—D—Trp(CHO)—NH₂ [137],

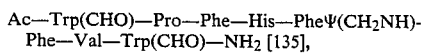

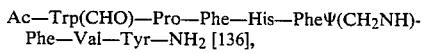

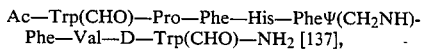

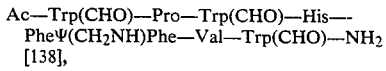

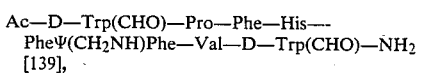

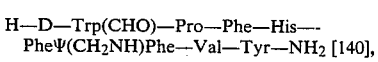

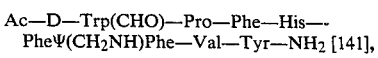

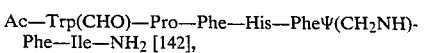

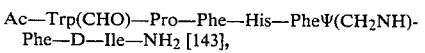

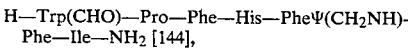

and

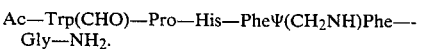

Compounds of the present invention wherein E₁₀F₁₁ is LeuΨ(CH₂NH)Val include

Ac—Trp(CHO)—ProΨ(CH$_2$NH)-
Phe($\alpha$—Me)—His—LeuΨ(CH$_2$NH)Val—Ile—Tyr—Lys—OH[147], Ac—Trp(CHO)—Pro—Phe—His—LeuΨ(CH$_2$NH)Val—Ile—Tyr—D—Lys—OH [148], and H—Trp(CHO)—Pro—Phe—His—LeuΨ(CH$_2$NH)Val—Ile—Tyr—D—Lys—OH [149].

Compounds of the present invention wherein E$_{10}$F$_{11}$ is Sta include

Ac—Trp(CHO)—Pro—Phe—His—Sta—Val—FTrp—NH$_2$ [150],

Ac—Trp(CHO)—Pro—Phe—His—Sta—Val—NH$_2$ [151],

Ac—Trp(CHO)—Pro—Phe—His—Sta—Ile—NH$_2$ [152],

Ac—Trp(CHO)—Pro—Phe—D—His—Sta—Ile—NH$_2$ [153],

Ac—Trp(CHO)—Pro—D—Phe—His—Sta—Ile—NH$_2$ [154],

Ac—Trp(CHO)—Pro—D—Phe—D—His—Sta—Ile—NH$_2$ [155],

Ac—Trp(CHO)—Pro—Phe—Dap—Sta—Ile—NH$_2$ [156],

Boc—Trp(CHO)—ProΨ(CH$_2$NH)—Phe—His—Sta—Ile—AMP,

Boc—Trp(CHO)—ProΨ(CH$_2$NH)—Phe—His—Sta—Ile—Trp(CHO)—OCH$_3$,

Ac—Trp(CHO)—ProΨ(CH$_2$NH)—Phe—His—Sta—Ile—Trp(CHO)—OCH$_3$,

Ac—Trp(CHO)—ProΨ(CH$_2$NH)—Phe—His—Sta—Ile—AMP,

H—Trp(CHO)—ProΨ(CH$_2$NH)—D—Phe($\alpha$—Me)—His—Sta—Ile—NH$_2$ [157],

H—Trp(CHO)—ProΨ(CH$_2$NH)-
Phe($\alpha$—Me)—His—Sta—Ile—NH$_2$ [158],

Ac—Trp(CHO)—ProΨ(CH$_2$NH)—D—Phe($\alpha$—Me)—His—Sta—Ile—NH$_2$ [159],

Ac—Trp(CHO)—ProΨ(CH$_2$NH)—Phe($\alpha$—Me)—His—Sta—Ile—NH$_2$ [160],

Ac—Trp(CHO)—Pro—Phe—His—Sta—Gly—NH$_2$, and

Ac—Trp(CHO)—Pro—Phe—His—Sta—NH$_2$.

Compounds of the present invention wherein E$_{10}$F$_{11}$ is Sta(NH$_2$) include Ac—Trp(CHO)—Pro—Phe—His—Sta(NH$_2$)—Ile—NH$_2$ [161], H—Trp(CHO)—Pro—Phe—His—Sta(NH$_2$)—Ile—NH$_2$ [162].

It is now further understood that the renin inhibiting peptide of the present invention includes both an N-alkyl His, preferably N-methyl His in the 9 position and a 1-formyl Trp in the 6 position of a renin inhibiting peptide, and further, a compound having (1) 1-formyl Trp as A$_6$ and (2) N-alkyl His, preferably N-methyl His, as D$_9$. Examples of compounds having combinations of N-alkyl His and 1-formyl Trp generally described above include:

AcFtrpProPheNMHisLeuΨ(CH[OH]CH$_2$)ValIleNH$_2$

AcFtrpProPheNMHisLeuΨ(CH[OH]CH$_2$)ValIleAMP [163]

and

BocFTrpProPheNMHisLeuΨ(CH[OH]CH$_2$)ValIleAMP [164].

The intermediate compound of formula I$_1$ may be used to prepare compounds known in the art, for example, the compounds of European published patent applications 45,161 and 53,017, and U.S. Pat. No. 4,424,207 cited above by methods described therein or otherwise known in the art. Additionally, the compound of formula I$_1$ may be modified to include novel compounds which are prepared by incorporating appropriate amino acids into the C-terminal or N-terminal portion of the formula I. These amino acids can have either the D- or L- configuration, the chain length can vary depending on the number of amino acids added to the N or C terminal ends of formula I$_1$ and any multitude of the contiguous amino acids may be included in this invention which provides novel isosteric polypeptides which are now found to have renin-inhibiting properties without the natural peptide sequence, i.e., ProPheHis left of the isosteric moiety as provided in U.S. Pat. No. 4,424,207. In other words, each of the amino acids Pro, Phe, His can be replaced by another appropriate amino acid to provide a novel isosteric polypeptide. For example, Phe can be replaced by dehydro Phe, Tyr, Trp, or 4-ClPhe, and Pro can be replaced by Δ3,4-Pro, 4-hydroxy Pro and thiazolidine-4-carboxylic acid. Further, it may be advantageous to alkylate the amide nitrogen with either methyl or ethyl to provide metabolic stability to the desired peptide. The N-terminal amino acid can be acylated by carboxylic acids such as acetic, isobutyric, isovaleric, hydrocinnamic, propionic, benzoic, $\alpha$-phenyl acetic acids. The C terminal amino acid can be derivatized to give esters of lower alkanols and amides of amines such as NH$_3$, NH$_2$—CH$_3$, NH$_3$—Et, NH$_2$—CH$_2$N(CH$_3$)CH$_3$, NH$_2$(CH$_2$)$_n$—NH$_2$, NH(CH$_2$)$_n$—NH—C(=NH)—NH$_2$ wherein n is limited to two to five carbons, inclusive.

The isostere of formula I$_1$ may be incorporated in peptide analogs by either methods as described in U.S. Pat. No. 4,424,207 and as described herein or by methods of peptide synthesis generally known in the art. In the case of the novel peptides of the formula XX$_1$, XX$_{10}$, the invention extends to the peptide itself or in any of various possible protected forms.

Although it is recognized that the amide nitrogen of various polypeptides can be alkylated to provide stability (see text above), it is now found that surprising and unexpected results are obtained through the methylation of the N as now shown in the divalent moiety XL$_3$ within the scope of D$_9$ above wherein R$_4$ is C$_1$-C$_5$alkyl. Preferred compounds of this type are as follows:

First, it is preferred that XL$_3$ represent an Nα-alkylated histidine and it is more preferred that it is an Nα-methylated histidine.

Species of the present invention which are among the more preferred having this feature are:

Boc—Pro—Phe—NMHis—LVA—Ile—AMP;

Boc—Phe—NMHis—LVA—Ile—AMP;

the former compound being most preferred.

Compounds containing the fragment XL$_1$ can be derived from 2-hydroxy acids. Several methods of synthesis of 2-hydroxy acids are found in R. Nishizawa, et al., J. Med. Chem., 20:510 (1977); R. Gamboni, et al., Tet. Letters, 26:203 (1985); H. C. Brown, et al., J. Am. Chem. Soc., 106:1531 (1984); M. Enomoto, et al., Tet. Letters, 26:1343 (1985), and references cited therein.

Some 2-hydroxy acids, such as L-phenyllactic acid, are available commercially. The method used to prepare S-3-(1-naphthyl)lactic acid of Example C61 is addition of NaNO$_2$ to L-3(1-naphthyl)alamine in 2.5N H$_2$SO$_4$. A double inversion occurs to give S-3-(1-naphthyl)lactic acid. In cases where the amino acid starting material is not available, the method of R. Nishizawa, et al., J. Med. Chem., 20:510 (1977) may be used to produce the R,S-2-hydroxy acid. The racemic acid may then be resolved by coupling to a chiral amine, such as L-prolinol, or L-prolinol silyl ether chromatographic separation of isomers, followed by hydrolysis of the amide bond to give the desired chiral 2-hydroxy acid. Acetylation of the 2-hydroxy group with Ac$_2$O and pyridine gives the O-acetyl acid, which is coupled to intermediates such as His(Tos)—LeuΨ[CH(OH)CH$_2$]Val—Ile—AMP with DCC or DEPC and Et$_3$N in CH$_2$Cl$_2$. The tosyl protecting group may be then removed with HOBT and MeOH. The 2-hydroxy acid may also be reacted with 2-equivalents of NaH in THF, followed by a carbamoyl chloride or isocyanate to give intermediates such as (CH$_3$CH$_2$)$_2$N—CO—L$_1$—OH for the example of diethyl carbamoyl chloride. This may then be coupled to a peptide intermediate as described immediately above. In addition to being novel amino acid replacements, resistance to chymotrypsin hydrolysis is expected as discussed by T. A. Steitz, R. Henderson, and D. Blow, HJ. Mol. Biol, 46:337-348 (1969).

Preferred compounds of this invention having this moiety are:

O—Ac—S—NLA(1)—His—LeuΨ[CH(OH)CH$_2$]Val—Ile—AMP

O—Ac—R—NLA(1)—His—LeuΨ[CH(OH)CH$_2$]Val—Ile—AMP

H—S—NLA(1)—His—LeuΨ[CH(OH)CH$_2$]Val—Ile—AMP (CH$_3$CH$_2$)$_2$N—C(O)—S—NLA(1)—His—LeuΨ[CH(OH)CH$_2$]Val—Ile—AMP

O—Ac—S—PLA—His—LeuΨ[CH(OH)CH$_2$]Val—Ile—AMP

Tba—S—PLA—His—Statine—Ile—AMP

O—Ac—S—NLA(1)—His—LeuΨ[CH(OH)CH$_2$]Val—MBA

H—PLA—His—Statine—Ile—AMP

O—Ac—PLA—His—Statine—Ile—AMP

O—Ac—PLA—His—Statine—Ile—Phe—OCH$_3$

H—PLA—His—LeuΨ[CH(OH)CH$_2$]Val—Ile—AMP

O—Ac—R—PLA—His—LeuΨ[CH(OH)CH$_2$]Val—Ile—AMP

O—Ac—PLA—His—LeuΨ[CH(OH)CH$_2$]Val—Ile—BPA.

Other compounds within the scope of this invention include:

Ac—FTrp—Pro—Phe—NMHis—Statine—NH$_2$,

Ac—FTrp—Pro—Phe—NMHis—LVA—NH$_2$,

Ac—FTrp—Pro—Phe—His—LVA—NH$_2$, (CH$_3$)$_2$NC(O)—NLA1—His—LVA—Ile—AMP, (CH$_3$)$_3$—CCH$_2$—NH—CO—NLA1—His—LVA—Ile—AMP,

Ac—NLA1—His—LVA—CMA, and

DEC—NLA1—His—LVA—CMA.

The most preferred compound of this invention is the citrate salt of Boc—Pro—Phe—NMHis—LVA—Ile—AMP.

DESCRIPTION OF THE PREFERRED EMBODIMENTS

The following Preparations and Examples illustrate the present invention. Unless otherwise noted the Preparations are illustrative of the corresponding steps as shown in Scheme II and in various of the lettered steps in the Scheme II's and Scheme III's. For example, Preparation I corresponds to Step I of Scheme II, but Preparation IA corresponds to Step IA of Scheme IIIA/B.

In this disclosure:
Ph is phenyl
DCC is dicyclohexylcarbodiimide
BOC is t-butoxycarbonyl
TBDMS is t-butyldimethylsilyl
TFA is trifluoroacetic acid
M or mol is mole
C is centigrade
ml is milliliter
THF is tetrahydrofuran
TLC is thin layer chromatography
EtOAc is ethyl acetate
A Lindlar catalyst is
   a modified 5% palladium or calcium carbonate catalyst, obtained from Engelhard Industries and used for reduction.
DMF is dimethylformamide
p-TSA salt is para-toluene sulfonic acid salt.
MS is mass spectroscopy.
IR is infra red spectra.
NMR is nuclear magnetic resonance.
HPLC is high performance liquid chromatography.
Skellysolve B is as defined in the Merck Index, 10th edition.
g. is grams.
min. is minute.

Me is methyl.
AMP is 2-(aminomethyl)pyridinyl.
Sta is statine as shown in FORMULAS.
Tos is p-toluenesulfonyl.
BOM is benzyloxymethyl.
Bz is benzyl.
The wedge-shaped line indicates a bond which extends above the plane of the paper relative to the plane of the compound thereon.
The dotted line indicates a bond which extends below the plane of the paper relative to the plane of the compound thereon.
Celite is a filter aid.
RIP means a compound having the formula H—Pro—His—Phe—His—Phe—Phe—Val—Tyr—Lys—OH.2($CH_3C(O)OH$).$XH_2O$ which is a known renininhibiting peptide.
Also, as used herein, particularly in Table A:
Abs means the moiety is absent;
AEP is 2-(2-pyridinyl)ethylamino;
ASta is 3-amino-3-deoxy-statine;
ASta3R is (3R)-amino-3-deoxy-statine;
AHPPA is (3S,4S)-4-amino-3-hydroxy-5-phenylpentanoyl;
BPA is N-benzyl-4-piperidinylamino;
Bla is racemic 2-oxy-4-phenylbutanoyl;
Boc is t-butoxycarbonyl;
CMA is cyclohexylmethylamide;
CRC is Cal$\Psi$($CH_2NH$)Cal where Cal is 3-cyclohexylalanyl;
Dap is 3-amino-alanyl;
DPhe is D-Phe;
DEC is diethylcarbamoyl ($Et_2NCO$-);
DMA is dimethylacetyl;
DNal2 is 3(2-naphthyl)-D-alanyl;
FIEA is 2-($N^{in}$-formyl-3-indolyl)ethylamino;
FTrp is $N^{in}$-formyl-Trp (also abbreviated Trp(CHO));
FTrpD is $N^{in}$-formyl-D-Trp;
Hyp is 4-hydroxyprolinyl;
HPhe is homoPhe i.e., (S)-2-amino-4-phenylbutanoyl;
IBA is isobutylamino;
IlR is "Isoleucyl reduced" i.e., isoleucyl with the carbonyl reduced to —$CH_2$—;
LeR is "leucyl reduced" i.e., leucyl with the carbonyl reduced to —$CH_2$—;
LRV is Leu$\Psi$($CH_2NH$)Val;
LVA is Leu$\Psi$(CH(OH)$CH_2$)Val with the S configuration at $C_4$ (the hydroxy-bearing carbon atom);
LVA4R is the same as LVA except the configuration at $C_4$ is R;
LVAME is like LVA except the carbonyl of "Val" has been reduced to hydroxymethyl which has been methylated (it is thus monovalent);
MBA is (S)-(−)-2-methylbutylamino;
Me is methyl;
MEC is methanesulfonylethoxycarbonyl (also known as MSOC);
MIl is N-methylisoleucyl;
MPhe is α-methyl-Phe;
MPr is α-methyl-Pro;
MSA is 2-(methanesulfonyl)acetyl;
MSP is 3-(methanesulfonyl)propionyl;
Nal1 is 3-(1-naphthyl)alanyl;
Nal2 is 3-(2-naphthyl)alanyl;
NBA is n-butylamino;
NHM is methylamino;
NLA1 is (s)-3-(1-naphthyl)lactoyl;
Nla1 is racemic 3-(1-naphthyl)lactoyl;
NLA1R is (R)-3-(1-naphthyl)lactoyl;
NLA2 is (s)-3-(2-naphthyl)lactoyl;
Nla2 is racemic 3-(2-naphthyl)lactoyl;
Nle is norleucine, i.e., the amino acid like Leucine but having n-butyl rather than isobutyl attached to the alpha carbon atom;
NMHis is Nα-methyl-histidine (also defined as N($CH_3$)His);
NMPhe is N-methyl-Phe;
NPG is N-(2-phenylethyl)glycyl;
NOA1 is (1-naphthyloxy)acetyl;
NOA2 is (2-naphthyloxy)acetyl;
OAcStat is O-acetylstatine;
OME is $OCH_3$;
PAP is Pro$\Psi$-($CH_2NH$)Phe, i.e., a group wherein the —COHN— of ProPhe is replaced by —$CH_2NH$—;
PEA is racemic 3-(2-phenylethyl)alanyl;
PEP is Pro$\Psi$($CH_2O$)Phe, i.e., a group wherein the —CO—NH— of ProPhe is replaced by —$CH_2$—O—;
PGA is pyroglutamoyl;
PhR is "phenylalanyl reduced" i.e., phenylalanyl with the carbonyl reduced to —$CH_2$—;
PLA is (S)-3-phenyllactoyl;
PLAR is (R)-3-phenyllactoyl;
POA is phenoxyacetyl;
PRP is Phe$\Psi$($CH_2NH$)Phe;
PrR is "prolyl reduced" i.e., prolyl with the carbonyl reduced to —$CH_2$—;
TBA is t-butylacetyl;
TMA is trimethylacetyl;
TSP is 3-(p-toluenesulfonyl)propionyl;
2HPA is (±)-(2-hydroxypropyl)amino;
3PA is 2-amino-3-(3-pyridinyl)propionyl, Isomer A (also abbreviated 3PAla(A));
3PB is 2-amino-3-(3-pyridinyl)propionyl, Isomer B (also abbreviated 3PAla(B));
2PR is 2-amino-3-(2-pyridinyl)propionyl (racemic) (also abbreviated 2PAla(d,l)); and
4PR is 2-amino-3-(4-pyridinyl)propionyl (racemic) (also abbreviated 4PAla(d,l)).
Chemical syntheses are indicated using a C prefix.
Biological Examples are indicated with a B prefix.

C1.

Preparation Scheme $I_1$ (S)-1-(3-Methyl-1-oxobutyl)-2-(3-methyl-1-oxobutyl)oxymethyl pyrrolidine.

A stirred solution of L-2-pyrrolidinemethanol (15.17 g, 0.15 mol) and pyridine (26.55 ml, 0.33 mol) in THF (200 ml) is cooled, under $N_2$ in an ice bath and treated dropwise during 45 min. with isovaleryl chloride (40.23 ml, 0.33 mol). The ice bath is removed after 15 min. and the mixture is kept at ambient temperature for 18 hr. and filtered. The solid is washed with dry ether and the filtrate is concentrated in vacuo. The residue is dissolved in ether; washed successively with cold 0.1N HCl, brine, saturated $NaHCO_3$ and brine; dried ($MgSO_4$) and concentrated to give a viscous oil.

The TLC system for this material is 2.5% MeOH-$CHCl_3$ on silica gel using phosphomolybdic acid spray to visualize the spots. It has been purified by distillation: b.p. 134°–139°/0.15 mm.

Anal. calcd. for $C_{15}H_{27}NO_3$: C, 66.87; H, 10.10; N, 5.20. Found: C, 66.72; H, 10.00; N, 5.24.

$[\alpha]_D^{25} = -55°$; IR, NMR, M.S. are consistent with the formula for the compound (S)-1-(3-Methyl-1- oxobutyl)-2-(3-methyl-1-oxobutyl)-oxymethylpyrrolidine.

C2.

Preparation Scheme I$_2$ (S)-1-(3-Methyl-1-oxobutyl)-2-(hydroxymethyl)pyrrolidine, II wherein R is isopropyl A stirred solution of the crude product from Preparation Scheme I$_1$ in acetonitrile (750 ml) is treated with 1.03N KOH (200 ml) and kept at ambient temperature for 18 hr. TLC with 2.5% MeOH-CHCl$_3$ on silica gel using phosphomolybdic acid or potassium permanganate spray indicates the absence of starting material. It is then concentrated in vacuo to remove acetonitrile; the remaining aqueous solution is saturated with NaCl, and extracted three times with CH$_2$Cl$_2$. The extracts are washed with dilute NaCl, dried (Na$_2$SO$_4$) and concentrated. The residue is treated with a little benzene and concentrated to give 28 g. of crude product which is distilled in a short path column with an air condenser at 0.05 mm to give 1.44 g., b.p. 114°–118° C. and 23.7 g., b.p. 118°–125° C. of (S)-1-(3-Methyl-1-oxobutyl)-2-(hydroxymethyl)pyrrolidine.

This material has been characterized by M.S., I.R. and NMR and found to be consistent with the formula for the compound (S)-1-(3-Methyl-1-oxobutyl)-2-(hydroxymethyl)pyrrolidine. It has $[\alpha]_D^{25} -56.0°$ C.

Anal. calcd. for C$_{10}$H$_{19}$NO$_2$: C, 64.83; H, 10.34; N, 7.56. Found: C, 65.09; H, 10.42; N, 7.43.

C3.

Preparation Scheme II$_1$

1-Hydroxy-5-methyl-2-hexyne, III wherein R$_1$ is isopropyl.

A stirred solution of 3M ethyl magnesium bromide in ether (121.7 ml, 0.365 mol) and ether (120 ml) under N$_2$, at ambient temperature is treated, dropwise during 1 hr. 45 min. with 4-methyl-1-pentyne (30.0 g., 0.365 mol) and the mixture is kept at ambient temperature for 18 hours. Use of the Gilman test, which shows the reaction is complete, is a faint positive. Paraformaldehyde (21.9 g., 0.730 mol), contained in a small flask, is then heated at 195°–200° C. and the formaldehyde gas with the aid of a slow N$_2$ stream is passed into the reaction mixture during 1 hour 50 minutes. After the addition the mixture is stirred for 50 minutes, cooled in an ice bath and treated with saturated aqueous NH$_4$Cl (330 ml) and ether (300 ml). The organic layer is separated and washed with water and brine. Filtration through celite may be necessary to break emulsions at this point. It may also be useful to include a wash with 10% aqueous sodium bisulfite to break up any formaldehyde polymers formed during the reaction. The aqueous layers are extracted with ether and the combined ether solution dried (MgSO$_4$) and concentrated. The residue is distilled at 1 mm to give 33.3 g., b.p. 46°–47° C. of 1-Hydroxy-5-methyl-2-hexyne.

This material has been characterized by IR, MS, and NMR.

Anal. calcd. for C$_7$H$_{12}$O; C, 74.95; H, 10.79. Found: C, 73.96; H, 10.91. The characterization is consistent with the formula for the compound 1-Hydroxy-5-methyl-2-hexyne.

C4.

Preparation I (E)-1-Hydroxy-5-methyl-2-hexene, IV wherein R$_1$ is isopropyl.

The alkyne prepared in Preparation Scheme II, above (40.53 g., 0.361 mol) is dissolved in THF (400 ml) and added during 35 minutes to a stirred suspension of LiAlH$_4$ (27.5 g., 0.723 mol) in THF (1500 ml) under N$_2$. The mixture is heated gently for 3 hours. TLC on silica gel with 20% EtOAc-cyclohexane and I$_2$ visualization indicates that the reaction is complete. It is then cooled in an ice bath and treated with H$_2$O (27.5 ml added slowly), 15% NaOH (27.5 ml) and water (82.5 ml). Stirring is continued for about 15 minutes. The solid is then collected by filtration and washed with Et$_2$O. The combined Et$_2$O solution is concentrated and the residue distilled at 8.2 mm to give 33.7 g., b.p. 67°–68° C. of (E)-1-Hydroxy-5-methyl-2-hexene.

This material is characterized by NMR, IR, MS.

Anal. calcd. for C$_7$H$_{14}$O: C, 73.63; H, 12.36. Found: C, 73.35; H, 12.49.

The characterization is consistent with the formula for the compound (E)-1-Hydroxy-5-methyl-2-hexene.

C5.

Preparation II (E)-1-Bromo-5-methyl-2-hexene, V wherein R$_1$ is isopropyl

A stirred solutin of the alcohol (16.14 g., 0.142 mol) and triphenylphosphene (40.85 g., 0.156 mol) in benzene (250 ml) is cooled in an ice bath and treated, portion wise with N-bromosuccinimide (27.72 g., 0.156 mol) during 50 minutes keeping the temperature of the reaction mixture at 40°–8° C. The mixture is kept in the bath for 27 minutes and at ambient temperature for 5 hours 30 minutes. TLC on silica gel with 5% MeOH-CHCl$_3$ using potassium permanganate spray to visualize the spots may be used to indicate the absence of starting material and thus reduce the reaction time. The resulting suspension is mixed with pentane (200 ml) and cooled in an ice bath. The solid is collected by filtration and washed well with pentane. The combined filtrate is concentrated under reduced pressure. The product is very volatile. Great care must be used to avoid losing it during the concentration steps. The residue is mixed with a little pentane and cooled in an ice bath to allow further precipitation of the solid biproducts which are removed by filtration. The filtrate is washed with cold 5% Na$_2$S$_2$O$_3$, twice with 0.5N NaOH and brine, dried (MgSO$_4$) and concentrated. The residue is distilled at about 20 mm to give 0.57 g. of a forerun and 20.85 g., b.p. 84°–87° C. of (E)-1-Bromo-5-methyl-2-hexene. The overall yield of this material is 40.3–55.8%.

This product is characterized by IR, NMR and MS.

Anal. calcd. for C$_7$H$_{13}$Br: C, 47.48; H, 7.40; Br, 45.12. Found: C, 46.58; H, 7.62; Br, 44.82.

The characterization is consistent with the formula for the compound (E)-1-Bromo-5-methyl-2-hexene.

C6.

Preparation IA (S)-1-[(2S,4E)-2-isopropyl-7-methyl-1-oxo-4-octenyl]-2-(hydroxymethyl)pyrrolidine, VIIIA wherein $R_1$ is isopropyl A stirred solution of diisopropylamine (30.09 ml, 0.2147 mol) in dry THF (75 ml) is cooled, under $N_2$, in a Dry Ice-acetone bath and treated during 29 minutes with 1.6M n-butyllithium (134.0 ml, 0.2144 mol). The mixture is kept in the bath for 9 minutes (a light precipitate may be observed) and then treated during 7 minutes with a solution of (S)-1-(3-methyl-1-oxobutyl)-2-hydroxymethylpyrrolidine as prepared in Preparation Scheme $I_2$ (19.84 g., 0.1071 mol) in THF (75 ml). The precipitate dissolves. The mixture is kept in the bath for 6 minutes and at ambient temperature for 3 hours 52 minutes (a light precipitate is again observed); it is then treated with hexa-methylphosphoramide (37.34 ml, 0.214 mol) and cooled in a dry ice-acetone bath. The mixture is treated during the 30 minutes with a solution of (E)-1-bromo-5-methyl-2-hexene from Preparation II (20.85 g., 0.1177 mol) in THF (40 ml) and kept in the dry ice bath for 5 hours. TLC on silica gel with 50% EtOAc-Skellysolve B may be used to indicate the absence of the starting material. The bath is re-moved and the mixture is stirred without cooling for 30 minutes; it is then poured into cold water (about 600 ml) and extracted three times with $Et_2O$. The extracts are washed with brine, dried ($MgSO_4$) and concentrated in vacuo to give 33.9 g. of crude (S)-1-[(2S,4E)-2-isopropyl-7-methyl-1-oxo-4-oxtenyl]-2-(hydroxymethyl) pyrrolidine. This is chromatographed on silica gel (about 2 kg) with 50% EtOAc-hexane to give 22.74 g. of the product as an amber oil.

This material is characterized by MS, IR and NMR. It has $[\alpha]_D^{25} -35.5°$ C.

The characterization is consistent with the formula for the compound (S)-1-[(2S,4E)-2-isopropyl-7-methyl-1-oxo-4-octenyl]-2-(hydroxymethyl) pyrrolidine.

C7.

Preparation IIA (S)-1-[(2S,4S,5S)-4,5-Dihydroxy-2-isopropyl-7-methyl-1-oxooctyl]-2-(hydroxymethyl)pyrrolidine (Isomer A), IXA wherein $R_1$ is isopropyl; and (S)-1-[(2S,4R,5R)-4,5-dihydroxy-2-isopropyl-7-methyl-1-oxooctyl]-2-(hydroxymethyl)pyrrolidine (Isomer B), IXB wherein $R_1$ is isopropyl A stirred mixture of (S)-1-[(2S,4E)-2-isopropyl-7-methyl-1-oxo-4-octenyl]-2-(hydroxy-methyl) pyrrolidine from the Preparation Scheme IA (22.74 g., 0.0808 mol), trimethylamine oxide dihydrate (12.17 g., 0.1095 mol), t-butanol (170 ml), distilled water (48.5 ml), pyridine (6.5 ml) and 2.5% $OsO_4$ in t-butanol (3.18 ml) is warmed to the reflux temperature during 45 minutes and refluxed for 3 hours. A slow stream of $N_2$ is passed through the system to help remove the trimethylamine formed in the reaction. TLC on silica gel with 35% acetone-$CH_2Cl_2$ and phosphomolybdic acid spray may be used to indicate the absence of starting material. The mixture is cooled to ambient temperature, treated with 20% aqueous $NaHSO_3$ (67 ml) and concentrated in vacuo to remove t-butanol. The residual aqueous mixture is saturated with NaCl and extracted four times with $Et_2O$. The extracts are washed twice with brine, dried ($MgSO_4$) and concentrated to give 27.94 g. of crude product. This material is chromatographed on silica gel to give 11.45 g. of Isomer A, 5.56 g. of a mixture and 7.79 g. of Isomer B. Rechromatog-raphy of the mixture gives 1.77 g. of additional Isomer A, and 1.81 g. of additional Isomer B. The overall yield for Isomer A (Step 1A to Step IIA) is 27.5-38.3%. The overall yield for Isomer B (Step 1A to Step IIA) is 20.7-27.8%.

Isomer A was characterized by NMR and MS; M+ calcd. for $C_{17}H_{33}NO_4$: 315.2409. Found: 315.2440. It has $[\alpha]_D^{25} -78.5$ (EtOH).

The characterization is consistent with the formula for the compound noted above as Isomer A.

Isomer B was characterized by NMR and MS; M+ calcd. for $C_{17}H_{33}NO_4$: 315.2409. Found: 315.2421. It has $[\alpha]_D^{25} -13.7$ (EtOH). Although Isomer B appears to be pure by TLC, an HPLC (Brownlee Labs 4.6 mm ID×25 cm RP 18 Spheri 10 column flow rate 2 ml/min. with 50% $H_2O$-MeOH for 0.5 minutes followed by a gradient from 50% $H_2O$ to 30% $H_2O$-MeOH during the 15 minutes) analysis demonstrated that later fractions contained an impurity (tR=9.8 min.). Isomer B has tR=9.4 min. This impurity can be separated by crystallization in the next step (IE) but apparently some of the desired product is lost in the process. HPLC pure Isomer B has $[\alpha]_D^{25} -6.1°$ (EtOH).

The characterization is consistent with the formula for the compound noted above as Isomer B.

C8.

Preparation IIIA

γ-Lactone of (2S,4S,5S)-4,5-Dihydroxy-2-isopropyl-7-methyloctanoic acid, XA wherein R and $R_1$ are isopropyl A stirred solution of (S)-1-[(2S,4S,5S)-4,5-dihydroxy-2-isopropyl-7-methyl-1-oxooctyl)-2-(hydroxymethyl) pyrrolidine (Isomer A from Preparation IIA) (11.45 g., 0.0363 mol) in dioxane (275 ml) is treated with 2N $H_2SO_4$ (275 ml) and the mixture refluxed, under $N_2$, for 4 hours. TLC on silica gel with 35% acetone-$CH_2Cl_2$ using phosphomolybdic acid spray may be used to indicate the absence of the starting material, thus reducing the reaction time. It is cooled to ambient temperature, saturated with NaCl, and extracted three times with $Et_2O$. The extracts are washed successively with brine, saturated with $NaHCO_3$ and brine, dried ($MgSO_4$) and concentrated in vacuo. A solution of the residue in $Et_2O$ is filtered through a small pad of Magnisol and crystallized from $Et_2O$-pentane to give: 5.02 g., m.p. 95.5-96.5; 1.02 g., m.p. 96°-97° C. and 0.094 g., m.p. 95°-96° C. of the γ-lactone of (2S,4S,5S)-4,5-dihydroxy-2-isopropyl-7-methyloctanoic acid.

Characterization by NMR, IR, MS; and Anal. calcd. for $C_{12}H_{22}O_3$: C, 67.25; H, 10.35. Found: C, 67.33; H, 10.29 is carried out on a product of the above reaction. It had $[\alpha]_D^{25} +13$ (EtOH).

The NMR (200 MHz, $CDCl_3$) had δ0.91-1.04 (octet, 12, $CH_3$), 1.26 (septet, 1, C-6HB), 1.55 (septet, 1, C-6HA), ~1.85 (m, 1, C-7H), ~2.14 (m, 4, C-2a, 3H, OH), 2.68 (d,d,d, 1, C-2H), 3.63 (decet, 1, C-5H), 4.30 (d,d,d, 1, C-4H).

The characterization is consistent with the formula for the γ-lactone of (2S,4S,5S)-4,5-Dihydroxy-2-isopropyl-7-methyloctanoic acid.

C9.

Preparation IVA using CCl$_4$

γ-Lactone of (2S,4S,5R)-5-Chloro-4-hydroxy-2-isopropyl-7-methyloctanoic acid, XIA wherein R and R$_1$ are isopropyl A stirred solution of γ-lactone of (2S,4S,5S)-4,5-dihydroxy-2-isopropyl-7-methyloctanoic acid from Preparation IIIA (3.8 g., 0.0177 mol) in CCl$_4$ (75 ml) is treated with triphenylphosphine (6.98 g., 0.0266 mol) and refluxed, under N$_2$, for 9 hours. TLC on silica gel with 20% EtOAc-Skellysolve B using phosphomolybdic acid spray may be used to indicate the absence of the starting material. The solution is kept at ambient temperature for 8 hours, diluted to a volume of 250 ml with Et$_2$O (pentane may be used for this purpose, thus allowing a more complete removal of triphenylphosphine oxide) and filtered. The solid is washed well with Et$_2$O (pentane may be used for this purpose, thus allowing a more complete removal of triphenylphosphine oxide) and the combined filtrates are concentrated to give 10.41 g. of a semi-solid residue. This is chromatographed on silica gel (600 g.) with 5% EtO-Ac-hexane to give 3.91 g. of the γ-lactone of (2S,4S,5S)-5-chloro-4-hydroxy-2-isopropyl-7-methyloctanoic acid.

This compound was crystallized from cold pentane for analysis, m.p. 49.5°–50° C.

Anal. calcd. for C$_{12}$H$_{21}$ClO$_2$: C, 61.92; H, 9.10; Cl, 15.23. Found: C, 62.32; H, 9.12; Cl, 15.34. [α]$_D^{25}$+35 (EtOH). The structure was also supported by IR, NMR and MS.

It has been found by TLC on silica gel with 50% CH$_2$Cl$_2$-hexane that this material is contaminated by an elimination product that cannot be detected with the 5% EtOAc-hexane system. Chromatography with 50% CH$_2$Cl$_2$-hexane can be used to separate these compounds. The product can be crystallized from pentane at or below 0° C. The next reaction (Preparation VA can, however, be carried out on the product obtained as described here.

C10.

Preparation VA (starting from Preparation IVA using CCl$_4$)

γ-Lactone of (2S,4S,5S)-5-Azido-4-hydroxy-2-isopropyl-7-methyloctanoic acid, XIIA wherein R and R$_1$ are isopropyl A stirred solution of the γ-lactone of (2S,4S,5R)-5-chloro-4-hydroxy-2-isopropyl-7-methyloctanoic acid from Preparation IVA, using CCl$_4$ (3.86 g., 0.0166 mol) in dimethylsulfoxide (50 ml), is treated with sodium azide (3.23 g., 0.0498 mol) and warmed under N$_2$, in an oil bath at 85°–90° C. for 39 hours. TLC on silica gel using both 50% EtOAc-hexane and 70% CH$_2$Cl$_2$-hexane as developing solvents, (with the former system the product azide moves just slower than the starting material—biproduct mixture and with the latter system the azide and biproduct move almost together but slower than the starting material) can be used to follow the disappearance of the starting material. The reaction is complete at this time (39 hours). Phosphomolybdic acid spray is used to visualize the spots. The mixture is cooled, poured into 250 ml of ice water and extracted four times with 50 ml portions of EtOAc. The extracts are washed with water and brine, dried (MgSO$_4$) and concentrated in vacuo to give 3.88 g. of crude product.

This is chromatographed on silica gel (250 g.) with 4% EtOAc-hexane to give 2.62 g. of the product.

This product was characterized by IR and NMR. It has [α]$_D^{25}$+29.38 (EtOH).

The characterization is consistent with the formula for the γ-lactone of (2S,4S,5S)-5-azido-4-hydroxy-2-isopropyl-7-methyloctanoic acid.

C11.

Preparation IVA (using CBr$_4$)

γ-Lactone of (2S,4S,5R)-5-Bromo-4-hydroxy-2-isopropyl-7-methyloctanoic acid, XIA wherein R and R$_1$ are isopropyl A stirred solution of the γ-lactone of (2S,4S,5S)-4,5-dihydroxy-2-isopropyl-7-methyloctanoic acid from Preparation IIIA (0.214 g., 1 mmol) and carbontetrabromide (0.431 g., 1.3 mmol) in acetonitrile (3 ml), under N$_2$ is cooled in a bath maintained at about 10° C. and treated, portion wise during the 20 minutes with triphenylphosphine (0.341 g., 1.3 mmol); a copious precipitate forms and additional aceto-nitrile (5 ml) is added to facilitate stirring. The mixture is kept at ambient temperature for 1 hour 30 minutes, at reflux for 3 hours 40 minutes, and at ambient temperature for 18 hours. By TLC on silica gel with 20% EtOAc-hexane there appears to be an equal mixture of starting material and product. Additional carbontetrabromide (0.332 g.) and triphenylphosphine (0.262 g.) are added and the mixture is kept at ambient temperature for 1 hour 45 minutes, and at reflux for 1 hour 30 minutes. The cooled mixture is mixed with Et$_2$O and filtered. The filtrate is concentrated and the residue chromatographed on silica gel (100 g.) with 7.5% EtOAc-hexane. The product thus obtained is crystallized from Et$_2$O-pentane to give 0.063 g., m.p. 61°–62.5° C. of the γ-lactone of (2S,4S,5R)-5-bromo-4-hydroxy-2-isopropyl-7-methyloctanoic acid.

The analytical sample was crystallized from cold pentane and had a m.p. 63.5°–64.5°; [α]$_D^{25}$+39° (EtOH). The structure was supported by IR, NMR and MS.

Anal. calcd. for C$_{12}$H$_{21}$BrO$_2$: C, 51.99; H, 7.64; Br, 28.83. Found: C, 51.92; H, 7.49; Br, 28.77.

C12.

Preparation IVA (using N-Bromosuccinimide)

γ-Lactone of (2S,4S,5R)-5-Bromo-4-hydroxy-2-isopropyl-7-methyloctanoic acid, XIA wherein R and R$_1$ are isopropyl A stirred solution of the γ-lactone of (2S,4S,5S)-4,5-dihydroxy-2-isopropyl-7-methyloctanoic acid from Preparation IIIA (0.214 g., 1 mmol) and triphenylphosphine (0.289 g., 1.1 mmol) in benzene (3 ml) is cooled in an ice bath and treated during 5–10 minutes with N-bromosuccinimide (0.196 g., 1.1 mmol). The mixture is kept cold for an additional 30 minutes and then at ambient temperature for 4 hours. It is diluted with Et$_2$O and filtered. The filtrate is con-centrated and the residue chromatographed on silica gel (100 g.) with 7.5% EtOAc-hexane. The product, the γ-lactone of (2S,4S,5R)-5-bromo-4-hydroxy-2-isopropyl-7-methyloctanoic acid, thus obtained was crystallized

C13.

Preparation VA (starting from Preparation IVA using CBr₄ or N-bromosuccinimide

γ-Lactone of (2S,4S,5S)-5-Azido-4-hydroxy-2-isopropyl-7-methyloctanoic acid, XIIA wherein R and R₁ are isopropyl A stirred solution of NaN₃ (98.5 mg, 1.52 mmol) in dry DMSO (3 ml) is treated with the γ-lactone of (2S,4S,5R)-5-bromo-4-hydroxy-2-isopropyl-8-methyloctanoic acid from Preparation IVA (using CBr₄) or IVA (using N-bromosuccinimide) (0.105 g., 0.379 mmol) and warmed, under $N_2$, at 80° C. for 15 hours 20 minutes. The reaction is over, as indicated, by TLC on silica gel with 70% CH₂Cl₂-hexane. It is mixed with cold water and extracted with EtOAc. The extracts are washed with water and brine, dried (MgSO₄) and concentrated. The residue is chromatographed on silica gel (50 g.) with 4% EtOAc-hexane to give 65 mg of the γ-lactone of (2S,4S,5S)-5-azido-4-hydroxy-2-isopropyl-7-methyloctanoic acid which is, therefore, identical to the material obtained in Preparation VA (starting from Preparation IVA using CCl₄).

C14.

Preparation VIA

γ-Lactone of (2S,4S,5S)-5-Amino-4-hydroxy-2-isopropyl-7-methyloctanoic acid, XIIIA wherein R and R₁ are isopropyl A mixture of the azide from any of the above described Preparations VA (2.85 g., 0.0119 mol), ethanol (150 ml) and Lindlar catalyst (1.0 g.) is hydrogenated at atmospheric pressure for 5 hours. The reaction is followed by TLC on silica gel using 4% EtOAc-hexane and phosphomolybdic acid spray to follow disappearance of the starting material and 5% MeOH-CH₂Cl₂ with ninhydrin spray to follow formation of the product. The catalyst is removed by filtration through Celite and the filtrate is concentrated in vacuo. To remove residual ethanol the residue is dissolved twice in benzene with concentration after each addition to give 2.64 g of an oily product.

This material was prepared and characterized by IR and NMR spectra which supports the formula for the γ-lactone of (2S,4S,5S)-5-amino-4-hydroxy-2-isopropyl-7-methyloctanoic acid.

C15.

Preparation VIIA

γ-Lactone of (2S,4WS,5S)-5-(t-Butoxycarbonylamino)-4-hydroxy-2-isopropyl-7-methyloctanoic acid, XIVA wherein R and R₁ are isopropyl.

A stirred solution of the γ-lactone of (2S,4S,5S)-5-amino-4-hydroxy-2-isopropyl-7-methyloctanoic acid from Preparation VIA (2.57 g) in THF (80 ml) is treated during 15 minutes with a solution of di-t-butyl dicarbonate (6.5 g, 0.0298 mol) in THF (50 ml). The mixture is kept under $N_2$ at ambient temperature for 15.5 hours, (TLC on silica gel with 5% MeOH-CH₂Cl₂ and ninhydrin spray shows the reaction is complete. It may be necessary to wash the γ-lactone from Preparation VIA with saturated sodium bicarbonate during workup to remove small amounts of acid which gives the amine salt which salt doesn't react with the anhydride. Alternatively, a small amount of aqueous NaHCO₃ may be added to the present reaction mixture.) and concentrated in vacuo to give 7.67 g of a semi-solid residue. This is chromatographed (The product is eluted in fractions (35 ml) 108–190. Ninhydrin spray can be used to visualize this material on a TLC plate.) on silica gel (400 g) with 8% EtOAc-hexane to give 3.48 g of a solid product, m.p. 143°–144.5° C.

The product may be crystallized from EtOAc-Skellysolve B. An analytical sample had m.p. 144.5°–146° C.

Anal. calcd. for C₁₇H₃₁NO₄: C, 65.14; H, 9.97; N, 4.47. Found: C, 65.26; H, 9.92; N, 4.34.

The Ir, NMR and MS support the structure for the γ-lactone of (2S,4S,5S)-5-(t-butoxycarbonylamino)-4-hydroxy-2-isopropyl-7-methyloctanoic acid. It has $[\alpha]_D^{25} -41°$ C.

C16.

Preparation VIIIA

Potassium Salt of (2S,4S,5S)-5-(t-Butoxycarbonylamino)-4-hydroxy-2-isopropyl-7-methyloctanoic acid, XVA wherein R and R₁ are isopropyl A stirred solution of the γ-lactone of (2S,4S,5S)-5-(t-butoxycarbonylamino)-4-hydroxy-2-isopropyl-7-methyloctanoic acid prepared in Preparation VIIA above (4.31 g., 0.0138 mol) in acetonitrile (215 ml) is mixed with water (170 ml) forming a precipitate and then the mixture is treated with 1N KOH (15.1 ml). The mixture is kept at ambient temperature under $N_2$, for 18 hours. (The mixture may be checked for starting material by TLC on silica gel with 10% EtOAc-hexane using ninhydrin spray.) and concentrated in vacuo to remove acetonitrile. The remaining aqueous solution is freeze dried. The residue, a potassium salt of (2S,4S,5S)-5-(t-butoxycarbonylamino)-4-hydroxy-2-isopropyl-7-methyloctanoic acid, which amounts to 5.64 g., is dissolved in absolute EtOH, treated with a little benzene and concentrated. The residue either is mixed with benzene and again concentrated to give a foam or lyopholized for 3 days to obtain a residue which is a white powder and is used directly in the following Preparation IXA. In this case the ethanol-benzene treatment is used to remove last traces of water.

C17.

Preparation IXA (Step 1)

t-Butyldimethyl silyl Ester of (2S,4S,5S)-5-(t-Butoxycarbonylamino)-4-(t-butyldimethylsilyloxy)-2-isopropyl-7-methyloctanoic acid.

A stirred mixture of the crude product, a potassium salt of (2S,4S,5S)-5-(t-butoxycarbonylamino)-4-hydroxy-2-isopropyl-7-methyloctanoic acid, from Preparation VIIIA in dry DMF (85 ml) is treated with imidazole (4.70 g., 0.069 mol) and t-butyldimethylsilyl chloride (5.2 g., 0.0345 mol). It is kept at ambient temperature, under $N_2$, for four days, (TLC on silica gel with 10% EtOAc-hexane and ninhydrin spray may be used to follow the reaction. This reaction mixture contains only one product by TLC. The spot has $R_F$ 0.6.) mixed with cold water (250–300 ml) and extracted four times with hexane. The extracts are washed twice with cold water, once with brine, dried (Na₂SO₄) and concentrated to give 8.23 g. of a colorless gum.

The structure for a t-butyldimethylsilyl ester of (2S,4S,5S)-5-(t-butoxycarbonylamino)-4-(t-butyldimethylsilyloxy)-2-isopropyl-7-methyloctanoic acid is supported by NMR.

C18.

Preparation IXA (Steps 2 and 3)

(2S,4S,5S)-5-t-Butoxycarbonylamino-4-t-butyldimethylsilyloxy-2-isopropyl-7-methyloctanoic acid, IA wherein R and $R_1$ are isopropyl A stirred solution of the t-butyldimethylsilyl ester of (2S,4S,5S)-5-(t-butoxycarbonylamino)-4-(t-butyldimethylsilyloxy)-2-isopropyl-7-methyloctanoic acid from Preparation IXA (Step 1) in MeOH (110 ml), under $N_2$, is treated with a solution of $K_2CO_3$ (2.1 g., 0.015 mol) in water (10 ml); and the mixture is kept at ambient temperature for 50 minutes. An immediate precipitate forms and TLC on silica gel with 10% EtOAc-hexane using ninhydrin spray may be used to indicate absence of starting material, thus showing less reaction time may be sufficient. It is then concentrated in vacuo to remove the MeOH. The residue is treated with ice cold brine (40 ml) and EtOAc (50 ml), cooled in an ice bath and acidified (pH 2-3) with 0.5M $KHSO_4$. The layers are separated and the aqueous layer is extracted twice with EtOAc (50 ml). The extracts are washed with brine, dried ($MgSO_4$) and concentrated to give 5.93 g of a gum. By TLC on silica gel with 10% MeOH-$CH_2Cl_2$ using ninhydrin spray this material has two spots. The faster spot represents the desired product, (2S,4S,5S)-5-t-butoxy-carbonylamino-4-t-butyldimethylsilyloxy-2-isopropyl-7-methyloctanoic acid. It is not known with certainty what the slower spot represents. This is chromatographed on silica gel (300 g.) with 3% MeOH-$CH_2Cl_2$ to give 4.81 g. (78.2%) of the product. The overall yield for this preparation (Step IIA to Step IXA) is 18.4-48%.

Characterization by IR, MS and NMR; $[\alpha]_D^{25} -33°$ (EtOH) supports the structure for (2S,4S,5S)-5-t-butoxycarbonylamino-4-t-butyldimethylsilyloxy-2-isopropyl-7-methyloctanoic acid.

C19.

Preparation IIIB

γ-Lactone of (2S,4R,5R)-4,5-Dihydroxy-2-isopropyl-7methyloctanoic acid, XB wherein R and $R_1$ are isopropyl A stirred solution of 1-[(2S,4R,5R)-4,5-dihydroxy-2-isopropyl-1-oxobutyl]-(S)-2-(hydroxymethyl) pyrrolidine (Isomer B) from Preparation IIA in dioxane (250 ml) is treated with 2N $H_2SO_4$ (240 ml) and refluxed gently for 3.5 hours. The starting material is gone by TLC on silica gel with 35% acetone-$CH_2Cl_2$ and phosphomolybdic acid spray. It is cooled to ambient temperature, saturated with NaCl and extracted three times with $Et_2O$. The extracts are washed with brine, saturated with $NaHCO_3$ and brine, dried ($MgSO_4$) and concentrated in vacuo. The residue is mixed with a little benzene and concentrated. The resulting material is dissolved in $Et_2O$, filtered through a small pad of Magnisol and crystallized from $Et_2O$-pentane to give three crops of product, γ-lactone (2S,4R,5R)-4,5-dihydroxy-2-isopropyl-7-methyloctanoic acid. (Crystallization is carried out by concentrating the $Et_2O$ on a steam bath and slowly replacing the $Et_2O$ with pentane. The higher melting product begins to crystallize from the warm solution during concentration. It is usually recrystallized once or twice.) This preparation gave 3.04 g., having an m.p. 93.5°-95.5° C.; 0.78 g., m.p. 94°-95.5° C. and 0.219 g., m.p. 94°-95° C. of the α-lactone of (2S,4R,5R)-4,5-dimethyl-2-isopropyl-7-methyl-octanoic acid. Crystallization of the mother liquors from $Et_2O$-pentane or pentane gave 0.663 g., m.p. 73.5°-82° C.; 0.104 g., m.p. 70°-72.5° C.; 0.424 g., m.p. 69°-73.5° C. and 0.200 g., m.p. 65.5°-69° C.

The product was characterized by IR, NMR and MS. Anal. calcd. for $C_{12}H_{22}O_3$: C, 67.25; H, 10.35. Found: C, 67.30; H, 10.53.

It had $[\alpha]_D^{25} -28°$. The NMR (200 MHz, $CDCl_3$) had: δ1.86 (sextet; 1; J=10.3, 12.4, 12.4); C-3HB, 2.15 (d,d,d; 1; J=6.2, 9.0, 12.5; C-3HA), 2.64 (d,d,d; 1; J=5.1, 9.0, 12.3; C-2H), 4.22 (d,d,d; 1; J=5.4, 6.1, 10.3; C-4H).

The characterization supports the structure for the γ-lactone of (2S,4R,5R)-4,5-dihydroxy-2-isopropyl-7-methyloctanoic acid.

C20.

Preparation XB

γ-Lactone of (2S,4R,5R)-4-Hydroxy-2-isopropyl-5-methanesulfonyloxy-7-methyloctanoic acid, IVIB wherein R and $R_1$ are isopropyl A stirred solution of the γ-lactone of (2S,4R,5R)-4,5-dihydroxy-2-isopropyl-7-methyloctanoic acid from Preparation IIIB above (7.28 g., 0.0340 mol). in $CH_2Cl_2$ (155 ml) is cooled in an ice bath under $N_2$ and treated with triethylamine (7.10 ml, 0.0510 mol) and then also treated dropwise during 10 minutes with a solution of methanesulfonyl chloride (2.9 ml, 0.0374 mol) in $CH_2Cl_2$ (20 ml). The mixture is kept in the ice bath for 30 minutes, (This reaction may be followed by TLC on silica gel using phosphomolybdic spray. With $CH_2Cl_2$ the $R_f$'s of starting material and product are 0.07 and 0.23; with 20% EtOAc-hexane they are 0.27 and 0.24, respectively.) and mixed with ice water (75-100 ml). The layers are separated and the aqueous layer is extracted twice with $CH_2Cl_2$. The organic layers are washed with 1N HCl. aqueous $NaHCO_3$ and dilute NaCl, dried ($MgSO_4$) and concentrated in vacuo to give 10.37 g. of the product.

The product is characterized by NMR which supports the structure for the γ-lactone of (2S,4R,5R)-4-hydroxy-2-isopropyl-5-methanesulfonyloxy-7-methyloctanoic acid.

C21.

Preparation XIB

γ-Lactone of (2S,4R,5S)-5-Azido-4-hydroxy-2-isopropyl-7-methyloctanoic acid, XIIB wherein R and $R_1$ are isopropyl A stirred mixture of sodium azide (6.63 g., 0.102 mol) in dimethylsulfoxide (130 ml) is treated with a solution of the mesylate, γ-lactone of (2S,4R,5R)-4-hydroxy-2-isopropyl-5-methanesulfonyloxy-7-methyloctanoic acid, formed in Preparation XB above in DMSO (25 ml), and the mixture is kept at 85° C. under $N_2$ for 22 hours. The reaction is shown to be complete by TLC on silica gel with 10% EtOAc-hexane and phosphomolybdic acid spray. It is cooled, poured into ice water (750 ml) and extracted four times with EtOAc (150 ml). The extracts are washed with water and brine, dried (MgSO$_4$) and concentrated in vacuo. The residue is chromatographed on silica gel with 8% EtOAc-hexane to give 7.31 g. of product, γ-lactone of (2S,4R,5S)-5-azido-4-hydroxy-2-isopropyl-7-methyloctanoic acid.

This product was characterized by IR and NMR and the characterization supports the structure for the γ-lactone of (2S,4R,5S)-5-azido-4-hydroxy-2-isopropyl-7-methyloctanoic acid.

C22.

Preparation VIB

γ-Lactone of (2S,4R,5S)-5-Amino-4-hydroxy-2-isopropyl-7-methyloctanoic acid, XIIIB wherein R and R$_1$ are isopropyl A solution of the product, the γ-lactone of (2S,4R,5S)-5-azido-4-hydroxy-2-isopropyl-7-methyloctanoic acid from Preparation XIB above (7.31 g.) in 95% EtOH (350 ml) is treated with Lindlar catalyst (2.4 g.) and hydrogenated at atmospheric pressure by a process analogous to that described by E. J. Corey et al., Synthesis 590 (1975). The system is evacuated and filled with hydrogen after 25, 55, 90 and 265 minutes. Stirring is continued for a total of 4 hours 55 minutes. TLC on silica gel with 10% EtOAc-hexane and phosphomolybdic acid spray shows the reaction is complete. The product is represented by a single spot (R$_f$ 0.3) on silica gel TLC with 5% MeOH-CHCl$_3$ and ninhydrin spray. The catalyst is removed by filtration through Celite, and the filtrate is concentrated in vacuo. The residue is dissolved in a little toluene and concentrated to remove the EtOH.

C23.

Preparation VIIB

γ-Lactone of (2S,4R,5S)-5-(t-Butoxycarbonylamino)-4-hydroxy-2-isopropyl-7-methyloctanoic acid, XIVB wherein R and R$_1$ are isopropyl.

A stirred solution of the product, the γ-lactone of (2S,4R,5S)-5-amino-4-hydroxy-2-isopropyl-7-methyloctanoic acid from Preparation VIB above in THF (50 ml) is cooled slightly in an ice-water bath and treated with di-t-butyldicarbonate (13.3 g., 0.0610 mol) and THF (10 ml). The mixture is kept at ambient temperature, under N$_2$ for 18 hours, (TLC on silica gel with 5% MeOH-CHCl$_3$ and ninhydrin spray may be used to show if starting material is present) treated with additional di-t-butyldicarbonate (3.32 g.) and stirred for 6 hours. The mixture is treated with a solution of NaHCO$_3$ (0.84 g., 0.01 mol) in water (10 ml), kept at ambient temperature for 2 hours and concentrated in vacuo. The residue is mixed with a little brine and extracted three times with EtOAc. The extracts are washed with brine, dried (MgSO$_4$) and concentrated. The residue is chromatographed on silica gel with 2% EtOAc-CH$_2$Cl$_2$. The product, γ-lactone of (2S,4R,5S)-5-(t-butoxycarbonylamino)-4-hydroxy-2-isopropyl-7-methyloctanoic acid, thus obtained was dissolved in pentane, filtered through a small pad of Magnisol and crystallized to give 6.73 g., m.p. 87.5°–89° C., 0.98 g., m.p. 87°–89° C. and 0.498 g., m.p. 87°–88.5° C.

It may be advantageous to cool the crystallizing mixture when crystallization is almost complete (cooling too soon may result in gel formation) at ambient temperature. The crystals may be washed with a little cold pentane.

The product of the present preparation is characterized by IR, NMR, MS.

Anal. calcd. for C$_{17}$H$_{31}$NO$_4$: C, 65.14; H, 9.97; N, 4.47. Found: C, 65.52; H, 10.10; N, 4.36. $[\alpha]_D^{25} - 62°$ (EtOH).

The characterization supports the structure for the γ-lactone of (2S,4R,5S)-5-(t-butoxycarbonylamino)-4-hydroxy-2-isopropyl-7-methyloctanoic acid.

A yield of 77% is obtained for Preparations beginning with IIIB, and continuing through XB, XIB, XIIB, XIIIB and VIIB.

C24.

Stability Test (Step VIIB)

γ-Lactone of (2S,4R,5S)-5-(t-Butoxycarbonylamino)-4-hydroxy-2-isopropyl-7-methyloctanoic acid—Determination of Diastereomeric Stability to Alkaline Hydrolysis Conditions A stirred solution of the γ-lactone of (2S,4R,5S)-5-(t-butoxycarbonylamino)-4-hydroxy-2-isopropyl-7-methyloctanoic acid from Preparation VIIB (100 mg, 0.319 mmol) in acetonitrile (5 ml) is treated with water (4 ml) and 1N KOH (0.35 ml). It is kept at ambient temperature, under N$_2$ for 5 hours. By TLC on silica gel with 10% EtOAc-hexane there appeared to be a trace of unreacted starting material. An additional one drop of 1N KOH is added and the mixture is kept at ambient temperature for two additional hours. It is then concentrated in vacuo to remove CH$_3$CN and the residue is freeze dried. The resulting fluffy white powder still appears to contain a trace of starting material by TLC. It is mixed with dioxane (5 ml), treated with 2N H$_2$SO$_4$ (5 ml), stirred and warmed at 70° C. for 2 hours 10 minutes. By TLC on silica gel with 5% MeOH-CHCl$_3$ the product appears to be the same as an authentic sample of the γ-lactone of (2S,4R,5S)-5-amino-4-hydroxy-2-isopropyl-7-methyloctanoic acid. The mixture is neutralized with solid NaHCO$_3$, saturated with NaCl and extracted to give 70 mg of the product. A stirred solution of this material in THF is treated with di-t-butyldicarbonate (140 mg) and kept at ambient temperature for 18 hours. By TLC on silica gel with 20% EtOAc-hexane the product appears to be the same as an authentic sample of γ-lactone of (2S,4R,5S)-5-(t-butoxycarbonylamino)-4-hydroxy-2-isopropyl-7-methyloctanoic acid. The mixture is concentrated and the residue chromatographed on silica gel (75 g.) with 15% EtOAc-hexane. The product thus obtained is crystallized from pentane to give 32 mg, m.p. 87°–88.5° C. The mixture melting point with an authentic sample of γ-lactone of (2S,4R,5S)-5-(t-butoxycarbonylamino)-4-hydroxy-2-isopropyl-7-methyloctanoic acid is undepressed. The IR spectrum is the same as that of the authentic sample.

The above test has provided evidence of the stability of the (2S) substituent of the compound XIVB to the alkaline hydrolysis conditions of Step VIIIB.

C25.

Preparation VIIIB

Potassium Salt of (2S,4R,5S)-5-(t-Butoxycarbonylamino)-4-hydroxy-2-isopropyl-7-methyloctanoic acid, XVB wherein R and $R_1$ are isopropyl A stirred solution of the γ-lactone of (2S,4R,5S)-5-(t-butoxycarbonylamino)-4-hydroxy-2-isopropyl-7-methyloctanoic acid prepared in Preparation VIIB (1.262 g., 4 mmol) in acetonitrile (63 ml) is treated with distilled water (50 ml) and 1N KOH (4.4 ml). The mixture is kept under $N_2$ for 20 hours and concentrated in vacuo to remove the acetonitrile. The aqueous solution that remains is freeze dried to give the product, a potassium salt of (2S,4R,5S)-5-(t-butoxycarbonylamino)-4-hydroxy-2-isopropyl-7-methyloctanoic acid, a fluffy white solid.

This reaction may be followed by TLC on silica gel with 20% EtOAc-hexane and ninhydrin spray. There is a trace of the starting material present after 3 hours and none after 20 hours.

C26.

Preparation IXB (Step 1)

t-Butyldimethylsilyl ester of (2S,4R,5S)-5-(t-butyldimethylsilyloxy)-2-isopropyl-7-methyloctanoic acid, IB wherein R and $R_1$ are isopropyl A stirred mixture of the product, the potassium salt of (2S,4R,5S)-5-(t-butoxycarbonylamino)-4-hydroxy-2-isopropyl-7-methyloctanoic acid from Preparation VIIIB (1.63 g., 4 mmol) in dry DMF (30 ml) is treated with imidazole (1.63 g., 24 mmol) and t-butyldimethylsilyl chloride (1.81 g., 12 mmol) and kept under $N_2$ at ambient temperature for 20 hours. By TLC on silica gel with 10% EtOAc-hexane and ninhydrin spray there are two product spots at $R_f$ 0.7 and 0.18. It appears that the slow moving material is an ester alcohol. This reaction should, therefore, be ran longer than 20 hours, perhaps 2-4 days. It is poured into cold water (90-100 ml) and extracted four times with hexane. The extracts are washed twice with water and once with brine, dried ($Na_2SO_4$) and concentrated to give 2.26 g. of a colorless oil.

C27.

Preparation IXB (Steps 2 and 3)

(2S,4R,5S)-5-(t-Butoxycarbonylamino)-4-(t-butyldimethylsilyloxy)-2-iso-propyl-7-methyloctanoic acid, IB wherein R and $R_1$ are isopropyl A stirred solution of the product, a t-butyldimethylsilyl ester of (2S,4R,5S)-5-(t-butoxycarbonylamino)-4-(t-butyldimethylsilyloxy)-2-isopropyl-7-methyloctanoic acid from Preparation IXB (Step 1) above (2.26 g.) in MeOH (30 ml) is treated with a solution of potassium carbonate (0.62 g., 4.4 mmol) in water (2.8 ml). The solution becomes cloudy and a white precipitate forms. The mixture is kept at ambient temperature for 1 hour 15 minutes (by TLC on silica gel with 10% EtOAc-hexane and ninhydrin spray the reaction is complete) and concentrated in vacuo to remove the MeOH. The residue which contains a suspended solid is cooled in an ice bath, treated with a little cold brine and EtOAc, stirred and acidified to pH 3.5-4 with 0.5M $KHSO_4$. During this process the solid dissolves. The layers are separated and the aqueous layer is extracted twice with EtOAc. The extracts are washed twice with brine, dried ($MgSO_4$) and concentrated to give a solid residue (1.51 g.). By TLC on silica gel (ninhydrin spray) there are two products. With 5% MeOH-$CHCl_3$ they have $R_f$ 0.39 and 0.19; with 40% EtOAc-$CH_2Cl_2$ they have $R_f$ 0.8 and 0.2. This material was chromatographed on silica gel with 5% MeOH-$CH_2Cl_2$. Two products were obtained. The first material eluted from the column was crystallized from a very small volume of cold EtOAc to give 0.077 g., m.p. 106°-108.5° C.; 0.364 g., m.p. 94.5°-106.5° C. and 0.293 g., m.p. 103.5-106.5° C. of (2S,4R,-5S)-5-(t-butoxycarbonylamino)-4-(t-butyldimethylsilyloxy)-2-isopropyl-7-methyloctanoic acid. The analytical sample had a m.p. 107°-108.5° C. It was characterized by IR, NMR and MS; $[\alpha]_D^{25}$ −42° (EtOH).

Anal. calcd. for $C_{23}H_{47}NO_5Si$: C, 61.98; H, 10.63; N, 3.14. Found: C, 61.89; H, 10.78; N, 3.01.

This characterization supports the structure for (2S,4R,5S)-5-(t-butoxycarbonylamino)-4-(t-butyldimethylsilyloxy)-2-isopropyl-7-methyloctanoic acid.

The second material eluted from the column amounts to 0.36 g. of a white powder, m.p. 131°-132° C.

This material is the hydroxy acid by IR and NMR analysis. In separate experiments carrying through the procedures of Preparation IXB (Step 1), a reaction time of 3 days gave only the faster moving product. Then the only product here is (2S,4R,5S)-5-(t-butoxycarbonylamino)-4-(t-butyldimethylsilyloxy)-2-isopropyl-7-methyloctanoic acid.

C28.

Preparation III (Z)-1-Hydroxy-5-methyl-2-hexene, VI wherein $R_1$ is isopropyl A solution of 1-hydroxy-5-methyl-2-hexyne (7, 7.19 g., 0.0641 mol) in MeOH (100 ml) is treated with a 5% solution of quinoline in MeOH (5.4 ml) and Engelhard Lindlar catalyst (3.6 g.). The mixture is hydrogenated at an initial pressure of 30 psi. Hydrogen uptake is very rapid and the reaction is stopped briefly after 5 minutes to allow the mixture to cool. When the reduction stops after the uptake of about one equivalent of hydrogen the mixture is filtered through Celite and concentrated in vacuo. A solution of the residue in $Et_2O$ is washed with cold 0.1 NHCl (saturated with NaCl), brine, saturated $NaHCO_3$ and brine, dried ($MgSO_4$) and concentrated. The residue is combined with the product from the reduction of 1.0 g. (8.9 mmol) of alkyne and distilled to give 0.5 g. of a forerun and 6.44 g. of (Z)-1-hydroxy-5-methyl-2-hexene, which has a b.p. 61°-62°/6 mm. The structure was supported by IR, UV, NMR and MS.

Anal. calcd. for $C_7H_{14}O$: C, 73.63; H, 12.36. Found: C, 73.78; H, 12.53.

C29.

Preparation IV (Z)-1-Bromo-5-methyl-2-hexene, VII where $R_1$ is iso-propyl

A stirred solutin of (Z)-1-hydroxy-5-methyl-2-hexene as prepared in Preparation III, (9, 6.25 g., 0.0548 mol) and triphenylphosphene (15.8 g., 0.0603 mol) in benzene (100 ml) is cooled to 4° in an ice bath and treated portionwise during 15 minutes with N-bromosuccinimide (10.7 g., 0.0603 mol); the temperature of the mixture is maintained at 4°-8° during the addition; a solid begins to form by the end of the addition. The ice bath is removed after 15 minutes and the mixture is kept at ambient temperature for 2 hours 15 minutes, diluted with Et₂O and cooled in an ice bath. The cold mixture is filtered and the solid is washed with Et₂O. The combined filtrate is concentrated and the residue is mixed with pentane and filtered. The solid is washed with pentane and the combined filtrate concentrated. A solution of the residue in Et₂O is washed with 5% Na₂S₂O₃, twice with 0.5N NaOH and brine, dried (MgSO₄) and concentrated. The residue is distilled at 23 mm to give 0.42 g., b.p. 73°–74° and 6.89 g., b.p. 74°–75° of the product, (Z)-1-bromo-5-methyl-2-hexene. The structure was supported by NMR.

C30.

Preparation IB (S)-1-[(2S,4Z)-2-isopropyl-7-methyl-1-oxo-4-octenyl]-2-pyrrolidinemethanol, VIIIB wherein $R_1$ is isopropyl A stirred solution of diisopropylamine (9.91 ml) in THF (26 ml) is cooled in a Dry Ice-acetone bath, under $N_2$, and treated during 10 minutes with 1.6N n-butyl lithium (44.2 ml). After 22 minutes a solution of (S)-1-(3-methyl-1-oxobutyl)-2-pyrrolidinemethanol as prepared in Preparation Scheme $I_2$ above (6.54 g.) in THF (26 ml) is added during 7 minutes. The mixture is kept in the cooling bath for 5 minutes and at ambient temperature for about 3 hours. It is then treated with hexamethylphosphoramide (12.3 ml), cooled in a Dry Ice-acetone bath and treated during 10 minutes with a solution of (Z)-1-bromo-5-methyl-2-hexene (6.87 g.) in THF (13 ml). The mixture is kept in the bath for 3 hours 20 minutes and without cooling for an additional 25 minutes. It is then poured into cold water (200 ml) and extracted with Et₂O. The extracts are washed with brine, dried (MgSO₄) and concentrated. The residue is chromatographed on silica gel (500 g.) with 50% EtOAc-hexane to give 7.0 g. of the product, (S)-1-[(2S,4Z)-2-isopropyl-7-methyl-1-oxo-4-octenyl]-2-pyrrolidine-methanol, which had $[\alpha]_D^{25} - 50.8°$ (EtOH). The structure was supported by IR and NMR MS calcd. for $C_{17}H_{31}NO_2(M+)$: 281.2355. Found: 281.2357.

C31.

Preparation IIB ((S)-1-[(2S,4S,5R)-4,5-dihydroxy-2-isopropyl-7-methyl-1-oxooctyl]-2-pyrrolidinemethanol, Isomer C, IXC wherein R and $R_1$ are isopropyl; and
((S)-1-[(2S,4R,5S)-4,5-dihydroxy-2-isopropyl-7-methyl-1-oxooctyl]-2-pyrrolidinemethanol, Isomer D, IXD wherein R and $R_1$ are isopropyl.

A stirred mixture of (S)-1-[(2S,4Z)-2-isopropyl-7-methyl-1-oxo-4-octenyl]-2-pyrrolidinemethanol as prepared in Preparation IB (2.81 g., 0.01 mol), trimethylamine-N-oxide dihydrate (1.50 g., 0.0136 mol). pyridine (0.8 ml), water (6.0 ml) and t-butanol (21.1 ml), under $N_2$, is treated with a 2.5% solution of osmiumtetroxide in t-butanol (0.393 ml), warmed slowly (1 hour 15 minutes) to the reflux temperature and refluxed for 7 hours. It is kept at ambient temperature for 18 hours, mixed with 20% aqueous NaHSO₃ (10 ml) and concentrated in vacuo to remove t-butanol. The residual mixture is saturated with NaCl and extracted with Et₂O. The extracts are washed with brine, dried (MgSO₄) and concentrated. The residue is chromatographed on silica gel (250 g.) with 40–100% acetone-CH₂Cl₂. The first compound eluted from the column amounts to 0.21 g. of recovered starting material. The second compound amounts to 0.12 g. of an unknown biproduct. The third compound (A) amounts to 0.06 g. of a minor glycol isomer that had $[\alpha]_D^{25} - 76.6°$ (EtOH). The structure was supported by IR and NMR.

MS calcd. for $C_{17}H_{33}NO_4(M+)$: 315.2409. Found 315.2421.

The fourth compound amounts to 1.07 g. of Isomer C ((S)-1-[(2S,4S,5R)-4,5-dihydroxy-2-isopropyl-7-methyl-1-oxooctyl]-2-pyrrolidinemethanol that had $[\alpha]_D^{25} - 45.1°$ (EtOH). The structure was supported by IR and NMR.

MS calcd. for $C_{17}H_{33}NO_4(M+)$: 315.2409. Found: 315.2427.

The fifth compound (B) amounts to 0.09 g. of a second minor isomer that had $[\alpha]_D^{25} - 27.0°$ (EtOH). Its structure was supported by IR and NMR.

MS calcd. for $C_{17}H_{33}NO_4(M+)$: 315.2409. Found: 315.2414.

The sixth compound amounts to 0.93 g. of an oil which crystallized from cold Et₂O-pentane gives 0.291 g. of Isomer D ((S)-1-[(2S,4R,5S)-4,5-dihydroxy-2-isopropyl-7-methyl-1-oxooctyl]-2-pyrrolidinemethanol, m.p. 71°–73°. The analytical sample had m.p. 70°–73.5°, $[\alpha]_D^{25} + 44°$ (EtOH). The structure was supported by IR, NMR and MS.

Anal. calcd. for $C_{17}H_{33}NO_4$: C, 64.73; H, 10.54; N, 4.44. Found: C, 64.74; H, 10.27; N, 4.37.

C32.

Preparation IIIC

γ-Lactone of (2S,4S,5R)-4,5-Dihydroxy-2-isopropyl-7-methyloctanoic acid, XC wherein R and $R_1$ are isopropyl A stirred solution of (S)-1-[(2S,4S,5R)-4,5-dihydroxy-2-isopropyl-7-methyl-1-oxooctyl]-2-pyrrolidinemethanol, which is Isomer C prepared in Preparation IIB above (1.10 g., 0.00349 mol) in dioxane (26 ml) is treated with 2N H₂SO₄ (26 ml) and kept under $N_2$ at about 100° for 4 hours 20 minutes. It is then cooled, saturated with NaCl and extracted with Et₂O. The extracts are washed with brine, saturated with NaHCO₃ and brine, dried (MgSO₄) and concentrated. A solution of the residue in Et₂O is filtered through Magnisol and the product is crystallized from cold Et₂O-pentane to give 0.325 g., m.p. 70.5°–72.5° and 0.243 g., m.p. 70.5°–71.5° of the γ-lactone of (2S,4S,5R)-4,5-Dihydroxy-2-isopropyl-7-methyloctanoic acid. The analytical sample is crystallized from pentane and has m.p. 70.5°–72.5°; $[\alpha]_D^{25} + 12°$ (EtOH). The structure was supported by MS. The IR (Nujol) had bands at 3427 (OH) and 1737 (C=O) cm⁻¹. The NMR (200 MHz, CDCl₃) had δ1.97 (d,d,d; J=7.0, 8.5, 13.1; C-3HA), 2.30 (d,d,d; J=5.2, 10.4, 13.3; C=3HB), 2.68 (d,d,d; J=5.4, 7.0, 10.2; C-2H), 4.33 (d,d,d; J=3.2, 5.3, 8.4; C-4H).

C33.

Preparation IIID

γ-Lactone of (2S,4R,5S)-4,5-Dihydroxy-2-isopropyl-7-methyloctanoic acid, XD wherein R and $R_1$ are isopropyl.

A stirred solution of (S)-1-[(2S,4R,5S)-4,5-dihydroxy-2-isopropyl-7-methyl-1-oxooctyl]-2-pyrrolidinemethanol, which is Isomer D prepared in Preparation IIB above (0.792 g.) in dioxane (18 ml) is treated with 2NH₂SO₄ and warmed under N₂. After 4.5 hours of gentle reflux the colorless solution is cooled, saturated with NaCl and extracted with Et₂O. The extract is washed with brine, saturated with NaHCO₃ and brine, dried (MgSO₄) and concentrated. The residue is crystallized from cold Et₂O-pentane to give 0.393 g., m.p. 58°–60° and 0.085 g., m.p. 56°–58.5° of the γ-lactone of (2S,4R,5S)-4,5-dihydroxy-2-isopropyl-7-methyloctanoic acid. The analytical samples was recrystallized from pentane and had m.p. 58°–60°, $[\alpha]_D^{25} -44°$ (EtOH). The structure was supported by IR, NMR and MS.

Anal. calcd. for $C_{12}H_{22}O_3$: C, 67.25; H, 10.35. Found: C, 67.23; H, 10.21.

This compound is converted by Step IVD shown in Scheme IIID to the chloride XID, which is converted by Step VD shown in Scheme IIID to azide XIIB, all having R and R₁ as an isopropyl group.

C34.

Preparation XC and XIC

γ-Lactone of (2S,4S,5S)-5-Azido-4-hydroxy-2-isopropyl-7-methyloctanoic acid, XIIA wherein R and R₁ are isopropyl from γ-Lactone of (2S,4S,5R)-4,5-Dihydroxy-2-isopropyl-7-methyloctanoic acid.

A stirred solution of γ-lactone of (2S,4S,5R)-4,5-dihydroxy-2-isopropyl-7-methyloctanoic acid as prepared in Preparation IIIC above (214 mg, 1 mmol) in CH₂Cl₂ (4.5 ml) is cooled under N₂ in an ice bath and treated first with triethylamine (0.21 ml, 1.5 mmol) and then added dropwise during 5–10 minutes with a solution of methanesulfonyl chloride (0.085 ml, 1.1 mmol) in CH₂Cl₂ (0.5 ml). The mixture is kept in the ice bath for 40 minutes and then washed with cold water, dilute HCl, saturated NaHCO₃ and dilute NaCl, dried (Na₂SO₄) and concentrated. The residue amounts to 0.32 g. of the mesylate, XVIC wherein R and R₁ are isopropyl, which was pure by TLC on silica gel with 20% EtOAc-hexane ($R_{f=0.28}$). The structure was supported by IR and NMR.

A stirred mixture of NaN₃ (195 mg, 3 mmol) in DMSO (4 ml) is treated with a solution of the mesylate (0.31 g., 1 mmol) in DMSO (5–10 ml) and the mixture is kept under N₂ at 80°–85° for 7 hours and at ambient temperature for 8 hours. It is then mixed with ice water and extracted with EtOAc. The extracts are washed with water and brine, dried (MgSO₄) and concentrated. The residue is chromato-graphed on silica gel (75 g.) with 4% EtOAc-hexane. The product thus obtained amounts to 0.207 g. of an oil. The NMR spectrum of this material is essentially identical to that of an authentic sample obtained from γ-lactone of (2S,4S,5R)-5-chloro-4-hydroxy-2-isopropyl-7-methyloctanoic acid, prepared in Preparation IVA above. It has $[\alpha]_D^{25} +29.6°$ (EtOH). A sample of this azide is converted to γ-lactone of (2S,4S,5S)-5-(t-butoxycarbonylamino-4-hydroxy-2-isopropyl-7-methyloctanoic acid, as prepared in Preparation VIIA, which has m.p. 144°–146° and $[\alpha]_D^{25} -41°$. The IR spectrum of this material is identical to that of an authentic sample.

This compound is identical to the azide obtained from Isomer A above and obtained in Preparation VA.

In a manner similar to Preparations as shown above for Schemes I, II and III, compounds of the Schemes having R defined as isobutyl or phenylmethyl and R₁ defined as phenyl can be prepared. Thus, a novel compound having the formula I¹ wherein R is isopropyl, isobutyl, or phenylmethyl; R₁ is isopropyl or phenyl; R is OH or a protecting group; and R₁₁ is H or t-butoxycarbonyl can readily be prepared by the present invention processes.

Then reference may be made for synthetic methods by which isosteric replacement is generally accomplished. For example, see the disclosure of U.S. Pat. No. 4,424,207 or procedures generally known in the art.

Therefore, a reaction sequence for the preparation of compounds of formula XX disclosed herein is for example.

C35.

Example IA

Benzyl ester of N-[(2S,4S,5S)-5-(t-Butoxycarbonylamino)-4-(t-butyldimethylsilyloxy)-2-isopropyl-7-methyl-1-oxo-octyl]-L-isoleucine See Scheme IV, Step I A stirred solution of the benzyl ester of L-isoleucine, p-TSA salt (1.77 g., 4.49 mmol) in mmol) in DMF (25 ml) is cooled, under N₂, in an ice bath and treated with N-methylmorpholine (0.54 ml, 4.94 mmol). The mixture is kept in the ice bath of 1 hour, cooled in a salt-ice bath and treated with a solution of (2S,4S,5S)-5-(t-butoxycarbonylamino)-4-(t-butyldimethylsilyloxy)-2-isopropyl-7-methyloctanoic acid as prepared in Preparation IXA (Steps 2 and 3) above (2.0 g., 4.49 mmol) in DMF (10 ml), 1-hydroxybenztriazole (0.91 g., 6.73 mmol) and then during 7 minutes with a solution of dicyclohexylcarbodiimide (1.02 g., 4.94 mmol) in DMF (25 ml). The ice bath is maintained for about 3 hours and then allowed to warm slowly to ambient temperature. After a total reaction time of 24 hours the mixture is concentrated in vacuo. The residue is mixed with EtOAc and filtered. The filtrate is cooled in an ice bath and washed with ice cold 1N HCl, cold 1N NaOH, water and brine, dried (MgSO₄) and concentrated. The residue is chromatographed on silica gel (250 g.) with 10% EtOAc-Skellysolve B. The product, a benzyl ester of N-[(2S,4S,5S)-5-(t-butoxycarbonylamino)-4-(t-butyldimethylsilyloxy)-2-isopropyl-7-methyl-1-oxooctyl]-L-isoleucine, thus obtained amounts to 2.28 g. and has $[\alpha]_D^{25} -22.7°$ (EtOH); it is essentially pure by HPLC, isocratic with 10% H₂O-CH₃CN and a flow rate of 2 ml/minute on an RP-18, Spheri 10 column. The structure was supported by IR and NMR. MS had m/z 649 [m+H⁺].

C36.

Example IB

Benzyl ester of N-[(2S,4R,5S)-5-(t-Butoxycarbonylamino)-4-(t-butyldimethylsilyloxy)-2-isopropyl-7-methyl-1-oxo-octyl]-L-isoleucine A stirred solution of the benzyl ester of L-isoleucine, p-TSA salt (0.393 g., 1 mmol) in DMF (5 ml), under N₂, is cooled in an ice bath, treated with N-methylmorpholine (0.121 ml, 1.1 mmol) and kept for 45 minutes. The mixture is then cooled in a salt-ice bath and treated with (2S,4R,5S)-5-(t-butoxycarbonylamino)-4-(t-butyldimethylsilyloxy)-2-isopropyl-7-methyloctanoic acid (0.446 g., 1 mmol), hydroxybenztriazole (0.203 g., 1.5 mmol) and added dropwise during 3–5 minutes with a solution of dicyclohexylcarbondiimide (0.227 g., 1.1 mmol) in DMF (5 ml). The mixture is kept in the salt-ice bath for several hours while it warms to 0°; it is then replaced by an ice bath which is allowed to warm slowly to ambient temperature. After 20 hours the mixture is concentrated in vacuo. The residue is mixed with EtOAc and filtered. The filtrate is cooled in an ice bath and quickly washed with ice cold 1N HCl, 1N NaOH, water and brine, dried ($MgSO_4$) and concentrated. The residue is chromatographed on silica gel (100 g.) with 10% EtOAc-hexane. The product, benzyl ester of N-[(2S,4R,5S)-5-(t-butoxycarbonylamino)-4-(t-butyldimethylsilyloxy)-2-isopropyl-7-methyl-oxooctyl]-L-isoleucine, thus obtained amounts to 0.59 g. The structure was supported by IR and NMR. MS has [M+H$^+$] at m/z 649; [M+K$^+$] at 687.

Calcd. for $C_{36}H_{64}N_2O_6SiK$: 687.4170. Found: 687.4239.

C37.

Example IIB

Benzyl ester of N-[(2S,4R,5S)-5-(t-Butoxycarbonylamino)-4-hydroxy-2-isopropyl-7-methyl-1-oxooctyl]-L-isoleucine A stirred solution of the benzyl ester of N-[(2S,4R,5S)-5-(t-butoxycarbonylamino)-4-(t-butyldimethylsilyloxy)-2-isopropyl-7-methyl-1-oxooctyl]-L-isoleucine (0.40 g., 0.616 mmol) in THF (5 ml) is cooled in an ice bath, under $N_2$, and treated with a 1M solutin of tetrabutylammonium fluoride in THF (1.23 ml). The mixture is allowed to warm to ambient temperature. By TLC on silica gel with 10% EtOAc-hexane there is still starting material present after 1 hour. Additional tetrabutylammonium fluoride (0.62 ml) is added and the mixture is kept at ambient temperature for 22 hours. It is then mixed with water and extracted with EtOAc. The extracts are washed with brine, dried ($MgSO_4$) and concentrated. The residue is chromatographed on silica gel (75 g.) with 1% MeOH-$CH_2Cl_2$. The product, benzyl ester of N-[(2S,4R,5S)-5-(t-butoxycarbonylamino)-4-hydroxy-2-isopropyl-7-methyl-1-oxooctyl]-L-isoleucine, which is eluted after a minor biproduct amounts to 0.21 g. The structure was supported by IR and NMR. MS has [M+H$^+$] at m/z 535; [M+K$^+$] at m/z 573.

Calcd. for $C_{30}H_{50}N_2O_6K$: 573.3306. Found: 573.3329.

C38.

Example IIA

N-[(2S,4S,5S)-5-(t-Butoxycarbonylamino)-4-(t-butyldimethylsilyloxy)-2-isopropyl-7-methyl-1-oxooctyl]-L-isoleucine, A compound of formula XXIV wherein R and $R_1$ are isopropyl. See Scheme IV, step II.

A mixture of the benzyl ester of N-[(2S,4R,5S)-5-(t-butoxycarbonylamino)-4-(t-butyldimethylsilyloxy)-2-isopropyl-7-methyl-1-oxooctyl]-L-isoleucine as prepared in Example IA above (2.08 g., 3.21 mmol) in ethanol (100 ml) with 10% Pd/C (1.0 g.) is placed under hydrogen in the atmospheric hydrogenation unit. The mixture is vigorously stirred for over 40 minutes. 104 ml. of $H_2$ is consumed and uptake stops. Stirring is allowed to continue for 45 minutes. Then the stirring is stopped and the mixture is allowed to stand for one hour. TLC (15% EtOAc:SSB and 5% MeOH:$CH_2Cl_2$) indicates the reaction is complete. The mixture is filtered and washed with a methanol and methylene chloride mixture. The NMR is consistent with the product desired, N-[(2S,4S,5S)-5-(t-butoxycarbonylamino)-4-(t-butyldimethylsilyloxy)-2-isopropyl-7-methyl-1-oxooctyl]-L-isoleucine.

C39.

Example III

Compound of formula XXI wherein $R_1$ and $R_2$ are isopropyl

See Scheme IV, step III

Phenylalanine methyl ester hydrogen chloride (0.64 g., 0.00295 mol, 1 equiv.) is dissolved in DMF (18 ml) under $N_2$ and is cooled in an ice water bath. N-methylmorpholine (0.33 g., 0.36 ml, 0.00325 mol, 1.1 equiv.) is added to the solution. The reaction mixture is stirred in the ice $H_2O$ bath for an additional hour. A solution of N-[(2S,4S,5S)-5-(t-butoxycarbonylamino)-4-(t-butyldimethylsilyloxy)-2-isopropyl-7-methyl-1-oxooctyl]-L-isoleucine as prepared in Example IIA above (1.65 g., 0.00295 mol) in DMF (9 ml) is added to the reaction mixture which is cooled further in an ice brine bath. Then 1-hydroxybenzotriazole (0.60 g., 0.00443 mol, 1.5 equiv.) is added to the mixture, followed by the addition of dicyclohexylcarbodiimide (0.67 g., 0.00325 mol, 1.1 equiv.) in DMF (18 ml) over six minutes. Stirring of the mixture is continued. The cold bath along with the reaction mixture is allowed to warm to room temperature. Stirring of the mixture is continued at room temperature. After stirring for a total of 18 hours, the reaction mixture is filtered and concentrated. TLC, one with one run 5% MeOH:$CH_2Cl_2$, and another with 15% EtOAc:$CH_2Cl_2$ using ninhydrin on the first and phosphomolybdic acid on the second shows an absence of phenylalanine starting material and presence of product. The the reaction mixture is filtered and concentrated. The residue is treated with ethyl acetate; filtered again and the filtrate cooled in an ice bath. The filtrate is washed once with cold normal HCl and successively with cold normal NaOH, $H_2O$ and brine. Aqueous washes are backwashed with EtOAc. Then the organic fractions are dried over $MgSO_4$ and concentrated to give a clear gum which yields on of two isomers which is the desired product, a compound of formula XXIA wherein R and $R_1$ are isopropyl.

The isomer was prepared and an analysis using HPLC, TLC and MS showed the isomer was consistent with the desired product of formula XXI wherein R and $R_1$ are isopropyl.

Anal. calcd. for $C_{39}H_{69}N_3O_7SiK=758.4542$. Found [m.+K]$^+$ at m/z=758.4601.

C40.

Example IV

Methyl ester of N-[N-[(2R,4S,5S)-4-hydroxy-7-methyl-2-(1-methylethyl)-1-oxo-5-[[N-(phenoxyacetyl)-L-phenylalanyl]amino]octyl]-L-isoleucyl]-L-phenylalanine Compound of formula $XX_1$, wherein R and $R_1$ are isopropyl
See Scheme V.
Step I:
Preparation of the compound of formula $H_2N$—XXII wherein R and $R_1$ are isopropyl.

The protected amine of formula XXI as prepared in Example III above (0.07 g., 0.097 mmol) is dissolved in methylene chloride (1 ml) under $N_2$. Trifluoroacetic acid (1 ml) is added to the solution which is then stirred at room temperature for an hour and 10 minutes. TLC with 15% EtOAc:$CH_2Cl_2$ on silica gel indicates the reaction is complete. The reaction mixture is concentrated to a gummy residue which is then treated with $Et_2O$. The residue dissolves except for a small amount of flocculent material which is filtered through celite and concentrated. The residue is dissolved in $Et_2O$ again, washed with aqueous $NaHCO_3$, backwashed with $Et_2O$, dried and concentrated to a gummy solid residue.

An NMR and MS of the residue agreed with the desired compound $H_2NXXII$, having isopropyl as R and $R_1$.

$[m.+K]^+$ at m/z 658. Calcd. 658.4017. Found 658.4032.

Step II:

Preparation of step II reactant-Scheme V′, Peptide of formula B, hereinafter V′B.

A mixture of ester of formula V′A, shown in Scheme V′ (0.5 g., 0.00128 mol) in ethanol (22 ml) is placed in an atmospheric hydrogenation unit. Hydrogen (35.2 ml) in the presence of 10% Pd/C (0.2 g.) is taken up within 5 minutes. Over the next 10 minutes an additional 0.5 ml is consumed and then uptake stops. After 30 minutes the mixture is removed from the unit and TLC with 20% EtOAc: hexane indicates the reaction is complete. The catalyst is filtered off and a solid, apparently crystalline, residue remains after concentration on a rotary evaporator. A solid results from recrystallization from aqueous methanol having a melting point of 128–129.5° C.

MS and IR confirms that the structure of the solid is consistent with that shown as V′B in Scheme V′. $[\alpha]_D = +39°$.

Anal. Calcd. for $C_{17}H_{17}NO_4$: C, 68.21; H, 5.73; N, 4.68. Found: C, 67.91; H, 5.73; N, 4.56.

Preparation of the product shown for Step II.

The amine of formula $H_2N$-XXII as prepared in Example IV, Scheme V, step I above (0.07 g., 0.000113 mol) is dissolved in methylene chloride (8 ml) under $N_2$ and cooled in an ice bath. The compound of formula V′B as prepared immediately above (0.037 g., 0.000124 mol, 1.1 equiv.) is added to the solution. HOBT (1-hydroxybenzotriazole) (0.017 g., 0.000124 mol, 1.1 equiv.) is added to the reaction mixture and then a a solution of DCC (Dicyclohexylcarbodiimide) (0.026 g., 0.000124 mol, 1.1 equiv.) in dichloromethane (2 ml) is added. The mixture is stirred in the cold bath. After stirring for about four hours the TLC with 5% MeOH: $CH_2Cl_2$ using ninhydrin and heat indicates the amine of formula $H_2N$-XXII is gone. Stirring of the mixture in the cold bath is continues. After 20.5 hours of stirring in the cold bath, the reaction mixture is filtered, washed successively with ice cold aqueous $NaHCO_3$, $H_2O$ and dilute brine. The aqueous washes are then backwashed with EtOAc. Pooled organic fractions are dried over $MgSO_4$ and concentrated to a gummy residue. The gummy residue of 0.0638 g. was the desired product shown as the product of step II in Scheme V, by HPLC, TLC and MS.

MS found $[m.+H]^+$ at m/z=901 and calculated: 901.24.

Step III:

The product as prepared in Scheme V shown in step II above (0.063 g., 0.0000687 mol) is dissolved in THF (0.67 ml) under $N_2$. $H_2O$ (0.67 ml) is added to the solution. The solution is then cooled in an ice bath and glacial acetic acid (2 ml) is added. The complete solution is removed from the cooling bath and stirred at room temperature. After stirring for about 20 hours a precipitate appears. An aliquot is removed, the precipitate dissolved by adding methylene chloride, methanol and $CH_3CN$ and tested by TLC with 5% MeOH: $CH_2Cl_2$. There appears to be only a trace of the starting 'product' present. The reaction mixture is concentrated and placed under vacuum at room temperature for 2 hours. TLC with 5% MeOH: $CH_2Cl_2$ *shows considerable starting 'product' so additional THF* (1 ml), $H_2O$ (1 ml) and glacial acetic acid (3 ml) is added under $N_2$ and the mixture is again stirred for an additional 20 hours at room temperature. The mixture is then concentrated and again placed under vacuum at room temperature for 2 hours resulting in a solid residue which is washed, filtered three times with 0.5 ml aliquots of EtOAc. Then the resulting material is dried in a vacuum oven. HPLC and MS of the product was consistent with the desired product of formula $XX_1$. $[m.+H]^+$ at m/z. Calculated: 786.98. Found: 787.

C41.

Example V

Monoacetate of the methyl ester of N-[N-[(2S*,4S*,6S*)-4-hydroxy-7-methyl-2-(1-methylethyl-1-oxo-6-[[N-(phenoxyacetyl)-L-histidyl-]amino]heptyl]-L-isoleucyl)-L-phenylalanine See Scheme VI, compound $XX_2$ wherein R and $R_1$ are isopropyl.

Step I:

A protected histidine, shown as a reactant in step I of Scheme VI (0.66 g., 0.000177 mol, 1.1 equiv.) and the compound of formula $H_2N$-XXII as prepared in Example IV, step I (0.1 g., 0.000161 mol) above are dissolved in methylene chloride (3.1 ml) under $N_2$. The solution is cooled in a cold bath to $-12°$ C. 1-Hydroxybenzotriazole, HOBT, (0.024 g., 0.000177 mol, 1.1 equiv.) and 1-ethyl-3-(3-dimethylaminopropyl) carbodiimide hydrogen chloride (0.034 g., 0.000177 mol, 1.1 equiv.) are added to the cooled solution. Stirring is continues in the cold for 3 hours. The cooling bath and, therefore, also the reaction mixture are allowed to warm and the mixture is stirred at room temperature overnight. The pH of the mixture is about 5. After stirring overnight the TLC with 5% MeOH: $CH_2Cl_2$ *using ninhydrin spray appears to indicate the compound of formula $H_2N$-XXII is gone*. The reaction mixture is concentrated and residue is partitioned between EtOAc and ice cold 5% $NaHCO_3$. The organic fraction is separated and washed with additional cold 5% $NaHCO_3$. Additional washing is then carried out two times with 5% cold citric acid, and once each with $H_2O$ and brine. Aqueous washed are backwashed with EtOAc. The pooled organic fractions are dried over $MgSO_4$ and concentrated to an amorphous residue. TLC and MS was consistent with the formula for the desired product as shown for step I of Scheme VI. Calcd: 977.34. Found: $[m.+H]^+$ at m/z 977.

Step II: $H_2N$-XXII, having R and $R_1$ as isopropyl

The product as prepared in step I, Example V above (0.23 g., 0.000208 mol) is dissolved in methylene chloride (2 ml) under $N_2$. The solution is cooled in an ice bath. Trifluoroacetic acid (TFA) (2 ml) is added to the solution dropwise over 3 minutes. The mixture is stirred in the cold bath for 2 hours. An aliquot is removed, diluted with methylene chloride and treated with sufficient aqueous $NaHCO_3$ to make basic. The TLC on this treated aliquot with 7% MeOH: $CH_2Cl_2$ indicates the reaction is essentially complete. Concentration and drying under vaccum at room temperature followed by the usual workup yielded an amorphous solid.

The TLC, NMR and MS are consistent with a product desired for the compound having the formula $H_2N$-XXIII, wherein R and $R_1$ are isopropyl.

MS Found $[m.+H]^+$ at m/z=763. Calcd. for $C_{42}H_{62}N_6O_7$ 762.97.

Step II: $H_2N$-XXIII having R and $R_1$ as isopropyl, repeated

The product as prepared in step I, Example V above (0.119 g., 0.000124 mol) is again dissolved in methylene chloride (1.5 ml). Trifluoroacetic acid (TFA) (2 ml) is added to the solution dropwise over 5 minutes. The reaction mixture is stirred at room temperature for one hour 25 minutes. TLC with 7.5% minutes. TLC with 7.5% MeOH: $CH_2Cl_2$ indicates the reaction is complete. The mixture is concentrated and then concentrated again from toluene. The residue is dissolved in EtOAc and washed consecutively once each with aqueous $N_aHCO_3$, $H_2O$ and brine. After backwashing the aqueous washes with EtOAc, the pooled fractions are dried over $MgSO_4$ and concentrated. The NMR of this product indicates it is the same as that obtained in step II, immediately above.

Step III:

The compound of formula $H_2N$-III as prepared in Step II above (0.09 g., 0.000120 mol) is dissolved in $CH_2Cl_2$ (2 ml) under $N_2$. Phenoxyacetic acid (0.02 g., 0.000133 mol, 1.1 equiv.) is added to the solution. The resulting reaction mixture is cooled in an ice: MeOH bath. 1-Hydroxybenzotriazole (HOBT) (0.02 g.) is added to the mixture followed by the addition of 1-ethyl-3(3-dimethylaminopropyl)carbodiimide hydrogen chloride (WSCI.HCl) (0.025 g., 0.000133 mol, 1.1 equiv.). The mixture is maintained in an ice bath for about 45 minutes. Then the ice in the bath is allowed to melt and both the bath and reaction mixture are allowed to come to room temperature. The mixture is stirred at room temperature overnight, after which it contains a solid suspension. TLC, one with 7.5% MeOH: $CH_2Cl_2$ and another with 7.5% MeOH: $CH_2Cl_2$ and 0.5% $NH_4OH$, both using ninhydrin, show the amine which is the starting compound of formula $H_2N$-III is gone. The reaction mixture is concentrated and then EtOAc and cold 5% $NaHCO_3$ are added to residue. The solid material does not go into solution but an NMR in DMSO shows this could be the desired product.

Separation, washing, and backwashing of aqueous washes yields pooled fractions, which are dried and concentrated to give a material having a TLC with 7.5% MeOH: $CH_2Cl_2$ showing multiple spots. Again the insoluble material was separated, washed two times with EtOAc and air dried.

Step IV:

The insoluble material obtained in step III, immediately above (0.074 g., 0.0000825 mol), glacial acetic acid (0.5 ml) and absolute ethanol (1 ml) are combined having 10% Pd/C (0.1 g.) added and placed in an atmospheric hydrogenator with an excess of $H_2$ and stirred for 6 hours. Then the stirrer is turned off and the reaction mixture is allowed to stand at room temperature over the weekend. The stirrer is again started and allowed to continue for an additional 7 hours. The reaction mixture is removed from the hydrogenator, the catylst filtered off and the remainder concentrated to a gummy solid residue.

After the usual workup, 0.03363 g. of solid was obtained.

The MS of the solid is consistent with a product having the formula $XX_2$ wherein R and $R_1$ are isopropyl. That is 0.03363 g. of the monoacetate of the methyl ester of N-[N-[(2S*,4S*,6S*)-4-hydroxy-7-methyl-2-(1-methyl-ethyl-1-oxo-6-[[N-(phenoxyacetyl)-L-histidyl-]amino]heptyl]-L-isoleucyl)-L-phenylalanine is obtained.

The MS for the compound without the —$CH_3$-C(O)—OH salt is calcd. for $C_{42}H_{60}N_6O_8=776.95$. Found: $[m.+H]^+$ at m/z=777 and after the addition of KI, $[M+K]_+ = 815.4192$.

C42.

Example VI

A compound of formula $XX_3$ wherein R and $R_1$ are isopropyl

See Scheme VII.

Step I:

The compound of formula $H_2N$-XXIII as prepared in Example V, step II (see Scheme VI) (0.096 g., 0.000121 mol) is dissolved in $CH_2Cl_2$ (5 ml) under $N_2$ to which solution is added the acid having the formula XXV shown as a reactant in step I, Scheme VII (0.035 g., 0.000133 mol, 1.1 equiv.). The reaction mixture is stirred until a solution is obtained and then cooled in an ice: MeOH bath. 1-Hydroxybenzotriazole (HOBT) (0.018 g., 0.000133 mol, 1.1 equiv.) is added to the solution after which 1-ethyl-3(3-dimethylamino-propyl)carbodiimide hydrogen chloride (WSCI.HCl) (0.025 g., 0.000133 mol) is also added. Stirring is continued in the cold bath for about 2 hours and then the ice in the bath is allowed to melt and both the bath and the reaction mixture are allowed to come to room temperature. After stirring overnight the mixture contains a gel-like precipitate. TLC with 7% MeOH: $CH_2CL_2$ using ninhydrin indicates no amine of the starting compound having the formula $H_2N$-XXII remains. The mixture is concentrated, the residue treated with EtOAc and cold aqueous $NaHCO_3$. The mixture is filtered and the filtered material washed once each with EtOAc and then $H_2O$. The solid product is dried in a vacuum oven at room temperature to give 0.104 g. An additional 0.03 g. of product is obtained from the mixture by repeating the separation, backwashing the aqueous washes and then pooling these fractions and further drying and concentrating this material. The NMR in DMSO of the product is consistent with the desired structure shown as the product of step I in Scheme VII.

Step II:

Compound of formula $XX_3$ having R and $R_1$ as isopropyl

See Scheme VII, step II

The product as prepared in step I, immediately above (0.1 g., 0.0000992 mol) is dissolved in glacial acetic acid (0.6 ml) under $N_2$ to which is added absolute ethanol (1.2 ml). After the catalyst, 10% Pd/C (0.1 g.) is added, the resulting solution is spaced in an atmospheric hydrogenation unit. After stirring under $H_2$ for 25 hours the mixture is removed from the unit and filtered off the catalyst, concentrated and then concentrated two additional times but from toluene. The concentrate is placed under vacuum at room temperature which yields 0.0806 g. of a white powder, pure by HPLC.

The MS of the powder is consistent with the desired compound of formula $XX_3$. MS $[m.+H]^+$ at m/z. Found: 888. Calculated: 888.13.

To obtain a high resolution spectrum, KI was added. Theory for $C_{49}H_{73}N_7O_8K = 926.5157$. Found: 926.5168.

C43.

Example VII

A compound having the formula $XX_4$ wherein R and $R_1$ are isopropyl

See Scheme VIII.

Step I:

The compound of formula XXIV having R and $R_1$ as isopropyl as prepared in Example IIA and shown in Scheme IV (0.5 g., 0.000895 mol), 4-amino-1-benzylpiperidine (in excess of 0.29 g.), and 1-hydroxybenzotriazole, HOBT, (0.14 g., 0.001 mol) are dissolved in $CH_2Cl_2$ (5 ml) under $N_2$ and cooled in an ice bath. 1-Ethyl-3(3-dimethylamino propyl) carbodiimide hydrogen chloride (EDC.HCl) (0.19 g., 0.001 mol) is then added to the solution in portions over about one minute. The mixture is stirred in the cold bath for one-half hour, then allowed to warm to room temperature. Stirring is continued for four additional hours. TLC with 1% acetic acid: 10%MeOH; $CH_2Cl_2$ shows that the starting material having formula XXIV is still present. Stirring is continued at room temperature for one hour. Repeated TLC still shows starting material. Additional EDC.HCl (0.02 g.) is added and the mixture stirred an additional hour at room temperature. The TLC is still the same. The reaction mixture is concentrated in vacuo. The residue is added to ethyl acetate (50 ml) and extracted with 4% $NaHCO_3$/ice (25 ml) two times. The aqueous layers are extracted again with ethyl acetate (25 ml) and the pooled layers are washed with 5% citric acid/ice (10 ml) two times and then once with brine (10 ml). The product is worked up by conventional methods to give 0.30 g. solid.

Step II(1):

The purified product as prepared in step I immediately above (0.30 g.) is dissolved in $CH_2Cl_2$ (1.5 ml). The solution is cooled in an ice bath and trifluoroacetic ace (1.5 ml) is added dropwise over 2 minutes. The mixture is stirred at 5% for 10 minutes and then allowed to warm to room temperature. Stirring is continued for one and one-half hours. The mixture is then concentrated under a stream of $N_2$ for over one hour. TLC With 5% MeOH/$CH_2Cl_2$ shows no purified product that was used as starting material remains. The residue is added to cold ethyl acetate (15 ml) and then washed with 4% $NaHCO_3$ (6 ml) and ice, then again with 4% $NaHCO_3$ (3 ml) and ice. The aqueous layers are pooled and extracted with cold ethyl acetate (15 ml). Then the pooled ethyl acetate layers are dried with $Na_2SO_4$ and concentrated.

The NMR is consistent with the desired product having the TBDMS substituent present but no BOC substituent.

Step II(2):

The product of step II(1), immediately above (0.233 g., 0.00037 mol) is dissolved in $CH_2Cl_2$ (3 ml). Then protected histadine having the formula as shown as the reactant in step II(2) (0.165 g., 0.00402 mol) is added to the solution and the mixture is cooled with an ice bath. Dicyclohexylcarbodiimide (0.093 g., 0.00045 mol) in $CH_2Cl_2$ (2 ml) is added to the cooled mixture dropwise over five minutes. Then the reaction mixture is stirred in the cold bath for one-half hour. The reaction mixture is stirred overnight at room temperature. TLC shows good "product" and no remaining starting material. The solid product is filtered off the cool mixture and the filtrate concentrated. EtOAc is added to filtrate and the mixture cooled. No precipitate appears. Conventional workup procedures resulted in 0.32 g. product.

The MS of the product is consistent with that shown for step II of Scheme VIII. MS $[M.+H]^+$. Found: 1022. Calculated: 1022.

Step III:

First, a compound having the formula XXV, to be used as a reactant in step III(2) (see Scheme VIII), is prepared as follows:

α-Tert-butyloxycarbonylphenylalanine benzyl ester p-toluene sulfonate (2.15 g., 0.005 mol) is dissolved in $CH_2Cl_2$ (20 ml) under $N_2$. Dimethylaminopyridine (only about 0.06 g., 1 equiv.) is added to the solution at room temperature and the solution then cooled in an ice bath. t-Butylacetyl chloride (1.0 g., 0.0075 mol) is added to the cold solution and the rest of the dimethylaminopyridine (up to a total of 1.54 g., 0.0125) in $CH_2Cl_2$ (5 ml) over 15 minutes is then also added. During the initial drops the mixture becomes cloudy, but by the completion of the addition, a clear solution is obtained. The solution is stirred in the cold bath for four and one-half hours. TLC with 5% MeOH/$CH_2Cl_2$ shows some of the starting material, t-phenylalanine benzyl ester p-toluene sulfonate but good "product". So the solution is removed from the ice bath and stirred at ambient temperature for one hour. Then the reaction mixture is diluted with $CH_2Cl_2$ (20 ml), washed twice with water-ice (10 ml), once with 8% $NaHCO_3$/ice (10 ml) and then 1M $KHSO_3$-ice (10 ml) and finally, once with brine (10 ml). The product is dried with $MgSO_4$ and concentrated overnight to give 2.03 g. oil. The NMR of this product was consistent with the desired compound and is for use in the reaction hydrogenation without further purification which hydrogenation then gives the compound of formula XXV as follows.

The compound of the above reaction (2.0 g., 0.0059 mol) is dissolved in ethanol (150 ml) having the 5% Pd/C (0.35 g.) catalyst therein. Hydrogen is added on Parr at Pi of about 33 which after 10 minutes is 29. After 30 minutes the Pi is still about 29 psi. The reaction mixture is removed from the apparatus. TLC with 5% MeOH/$CH_2Cl_2$ shows no starting material remains. The catalyst is filtered off and the remaining mixture concentrated and dried in a vacuum oven overnight to give 1.36 g. of solid.

The NMR is consistent with that of a compound having formula XXV. Recrystallization provided a purified product of which showed a m.p. of 167°–68° C. $α_D$(MeOH)=6°, and Anal. calcd. C, 68.41; H, 8.04; N, 5.32. Found: C, 67.22; H, 7.91; N, 5.23.

Step III(1):

Now the product as prepared in step II(2), as shown in Scheme VIII above (0.3 g.) is dissolved in $CH_2Cl_2$ (1.5 ml). The solution is cooled in an ice bath. Trifluoroacetic acid (1.5 ml) is added dropwise to the cooled solution over about five minutes. The mixture is stirred over the cold bath for one-half hour. Then the mixture is removed from the ice bath and stirred at ambient temperature for an additional one one-fourth hours. After concentration under a stream of $N_2$ the mixture is set in freezer overnight. The residue is partitioned between about 10 ml of 4% $NaHCO_3$/ice and EtOAc (20 ml). The layers were separated and the aqueous layer extracted with EtOAc, the organic layers pooled and dried to yield 0.176 g. of product.

Step III(2):

The product of step III(1) immediately above (0.176 g., 0.000191 mol) is dissolved in $CH_2Cl_2$ (5 ml) having the product therein, the formula XXV as prepared above for use as a reactant now (0.055 g., 0.00021 mol). The solution is cooled in an ice bath to which is then added a solution of dicyclohexylcarbodiimide (0.047 g., 0.00023 mol) in $CH_2Cl_2$ (2ml) over about five minutes. The mixture is stirred in the cold bath for one-fourth hour and then removed from the ice bath. Stirring is continued at ambient temperature overnight. A gummy film deposits on the side of the flask. TLC shows mostly starting material which may be identified as the product of step III(1) above. More $CH_2Cl_2$ (5 ml) is added. TLC still shows some starting material but also shows a new product. Additional reactant XXV shown in Scheme VIII (0.011 g.) is added and also additional dicyclohexylcarbodiimide (0.009 g.) is added as above. This mixture is stirred for four hours at room temperature. TLC still shows some starting material as discussed above. A gummy precipitate continues to be present. More $CH_2Cl_2$ is added but filtering is unsuccessful. The mixture is dissolved in trichloromethane (about 100 ml), then concentrated. The residue is added to about 100 ml of EtOAc, washed with cold 4% $NaHCO_3$ (8 ml) and dried over $Na_2SO_4$. Concentration, silica chromatography using 1% $NH_4OH/5\%$ $MeOH/CHCl_3$ gives a product (0.081 g. and 0.043 g.) having a MS $[m.+H]^+$, Found: 1053; calcd.: 1053, which is consistent with the compound shown as the product of step III in Scheme VIII.

Step IV: A compound of formula $XX_4$ having R and $R_1$ as isopropyl

The compound which is the product of step III as prepared immediately above and shown in Scheme VIII (0.08 g.) is added to dimethylformamide (2 ml). 1-Hydroxybenzotriazole (HOBT) (0.032 g.) is then added to the solution and stirred at room temperature for 24 hours. TLC shows only a faint mark for remaining starting material and good "product". The mixture is concentrated under a stream of $N_2$ over four hours. EtOAc (25 ml) and ice cold dilute $NaHCO_3$ (4 ml) is added to the residue. The aqueous layer is removed and the organic layer is further extracted with another portion of dilute $NaHCO_3$ (4 ml), then water-ice and finally brine. The organic layer is dried over $Na_2SO_4$ and concentrated to give the product having the formula $XX_4$ wherein R and $R_1$ are isopropyl. Trituration of the product with EtOAc gives 0.055 g. of the purified product as a gummy solid which was further purified by silica gel chromatography.

The above step IV is repeated using a mixture of THF/DMF (6 ml/3 ml) as solvent. Both reactions of step IV gave the desired product of formula $XX_4$. TLC, HPLC and MS are consistent with this formula.

MS $[m.+H]^+$ calcd.: 898. Found: 899; and $[m.+K]^+$ calcd: 937.5681. Found: 937.5660.

C44.

Example VIII

Compound having formula $XX_5$ wherein R and $R_1$ are isopropyl

See Scheme IX

Step I

To a stirred solution of the benzyl ester of N-[(2S,4S,5S)-5-(t-butoxycarbonylamino)-4-(t-butyldimethylsilyloxy)-2-isopropyl-7-methyl-1-oxooctyl]-L-isoleucine as prepared in Example 1A above (0.5 g., 0.77 mmol) in ethanol (25 ml) is added Pd/C under $N_2$. The ester is hydrogenated on atmospheric hydrogenation apparatus (Pi=52 at 1:35 mm) to Pf 44 at 2:25 mm. The catalyst is filtered off and the filtrate concentrated in vacuum, taken up in ethanol, then filtered through a pad of celite. The material is again concentrated to obtain 0.41 g. of the acid, N-[(2S,4R,5S)-5-(t-butoxycarbonylamino)-4-(t-butyldimethylsilyloxy)-2-isopropyl-7-methyl-1-oxooctyl]-L-isoleucine.

TLC with 5% $MeOH/CH_2Cl_2$ and NMR results are consistent with the formula of the obtained product which is desired.

Step II

To the acid, N-[(2S,4R,5S)-5-(t-butoxycarbonylamino)-4-(t-butyldimethylsilyloxy)-2-isopropyl-7-methyl-1-oxooctyl]-L-isoleucine as prepared in step I immediately above (0.056 g., 0.1 mmol), 1-hydroxybenzotriazole (HOBT) (0.017 g., 0.13 mmol), N-methyl morpholine (0.011 ml, 0.11 mmol) in $CH_2Cl_2$ and cooled to 0° to −10° C. (ice-propanol) is added 1-ethyl-3-(3-dimethylaminopropyl)carbodiimide hydrochloride (0.022 g., 0.12 mmol). The mixture is stirred in the cold bath for four hours, then allowed to warm to room temperature and stirred for an additional one one-half hours. TLC on concentrated aliquot (under $N_2$) subsequently extracted from EtOAc with ice cold $NaHCO_3$ and ice, cold 10% citric acid, and then ice water shows "product" and with 0.5% HOAc: 5% MeOH: $CH_2Cl_2$ shows none of the isoleucine starting compound remaining. Therefore, the reaction mixture is concentrated under a stream of $N_2$. 5 ml EtOAc is added to the remainder including a gummy precipitate for extraction by addition of 1 ml saturated $NaHCO_3$ and 1 ml ice/water to obtain two clean layers. The aqueous layer is removed and the organic layer washed with 1 ml 10% citric acid and 1 ml ice/water then washed again with 1 ml saturated $NaHCO_2$ and 1 ml ice/water and finally with 1 ml ice water followed by brine. The aqueous washes are pooled and extracted with ethyl acetate (about 3 ml) but no product is found here. Then, the resulting material is dried with $MgSO_4$ and concentrated to give 0.04 g. of product of step II shown in Scheme IX. The NMR of the product is consistent with a compound having the formula shown as the product of step II in Scheme IX.

Step II is repeated using the following quantities of reagents:

(0.30 g., 0537 mmol) the acid, N-[(2S,4R,5S)-5-(t-butoxycarbonylamino)-4-(t-butyldimethylsilyloxy)-2-isopropyl-7-methyl-1-oxooctyl]-L-isoleucine.

(0.115 g., 0.533 mmol) L-phenylalanine methyl ester hydrochloride;

(0.064 g., 0.64 mmol) N-methylmorpholine;

(0.09 g., 1.67 mmol) hydroxybenzotriazole; and (0.123 g., 0.64 mmol) ethyldimethylamino propyl carbodiimide.

The NMR of the product (0.43 g.) is again consistent with that of a compound shown as the product of step II in Scheme IX.

Step III:

The compound having the formula shown as the product of step II in Scheme IX (0.072 g., 0.1 mmol) in methylene chloride (0.3 ml) under $N_2$ is cooled in an ice bath. Trifluoroacetic acid (0.3 ml) is added dropwise. The reaction mixture is stirred as it warms to room temperature and then at ambient temperature for a total of about two hours. The resultant mixture is concentrated under a stream of $N_2$ and set in freezer overnight. The TLC appears to be consistent with the desired product, i.e., the BOC- protective group is no longer present but the TBDMS group is still apparently present. About 10 ml of ethyl acetate is added and then washed two times with 1 ml 5% NaHCO$_3$/ice, then one time with brine. (Ethyl acetate is used to wash down separatory funnel so final total ethylacetate is 20 ml). The resultant material is dried over MgSO$_4$ and concentrated to obtain 50 mg of about which is dried further under a stream of N$_2$ and still contains about 50 mg of product shown as the compound produced in step III of Scheme IX.

Step III is repeated using the following quantities of reagents:

(0.35 g.) The compound having the formula shown as the product of step II in Scheme IX;

(1.5 ml) methylene chloride; and (1.5 ml) trifluoroacetic acid.

The NMR of the product (0.28 g.) was consistent with the desired compound of formula shown as the product of step III in Scheme IX.

Step IV:

The compound having the formula shown as the product of step III as prepared above from the 72 mg of the compound in step II immediately above in CH$_2$Cl$_2$ (2 ml) under N$_2$ is cooled in an ice bath. A protected histidine is added to a solution of dicyclohexyl carbodiimide (20 mg) in CH$_2$Cl$_2$ (1 ml) in a dropwise manner. The reaction mixture is stirred in the cold bath for 15 minutes. A precipitate forms. Stirring is continued at room temperature for one-half hour. The reaction mixture is set in the freezer overnight. After the mixture is allowed to warm to room temperature it is stirred for an additional one-half hour. TLC with 5% MeOH/CH$_2$Cl$_2$; 0.5% HOAc, 5% MeOH/CH$_2$Cl$_2$ shows no compound of formula shown as the product of step III in Scheme IX and no protected histidine remains. After again cooling the solution the precipitate is filtered out and the precipitate washed with cold CH$_2$Cl$_2$. The filtrate is concentrated, after which about 3-4 ml ethyl acetate is added, then cooled and a fine precipitate is filtered off. The filtrate is concentrated in a vacuum and the residue chromatographed on silica gel eluted with 1% MeOH/CH$_2$Cl$_2$ to yield 0.036 g. of product.

The NMR is consistent with the product shown as the formula produced by step IV in Scheme IX.

Step IV is repeated using the following quantities of reagents:

(0.28 g., 0.00039 mol) the compound having the formula XXIX$_2$ as prepared in step III in 3 ml of dry CH$_2$Cl$_2$;

(0.076 g., 0.00041 mol) ethyl diethylamino propyl carbodiimide hydrochloride; and (0.165 g., 0.00041 mol) protected histidine.

The desired compound having the formula XXIX$_3$ (420 mg) is obtained.

The following MS analysis agree with the formula for the compound produced in step III in Scheme IX.

The rotation was $\alpha_D^{EtOH} = -40°$ and

MS: $[m+H]^+1011$. Calculated: 1011.

Step V(1):

The compound having the formula shown as the product of step IV in Scheme IX (0.23 g., 0.228 mmol) in CH$_2$Cl$_2$ (1.25 ml) is cooled in an ice bath. Trifluoroacetic acid (1.25 ml) is added dropwise to the solution which is stirred for one-half hour and then removed from the ice bath. After the reaction mixture is allowed to stand for 45 minutes at ambient temperature it is concentrated under a stream of N$_2$ and washed twice with 4% NaHCO$_3$/ice (5 ml), then once with brine (5 ml). The aqueous layers are pooled and extracted with about 25 ml of ethyl acetate. The ethyl acetate layer is washed with brine and combined with the first ethyl acetate solution which is dried with MgSO$_4$; concentrated to give a product (0.175 g.) for use in the next reaction step V(2).

Step V(2) and (3):

The product of step V(1) in CH$_2$Cl$_2$ (5 ml) to which is added protected L-phenylalanine (0.052 g., 0.211 mmol) is cooled in an ice bath. Ethyl diethylaminopropylcarbodiimide hydrochloride is added to the reaction mixture in portions over one minute and stirred in the cold bath for 40 minutes. The mixture is allowed to warm to room temperature and stirring is continued for two and one-half hours. TLC shows only faintly protected L-phenylalanine remaining but the compound which is a product of step V (1) that is the starting material noted above appears to still be largely remaining. After two additional hours of stirring at room temperature the starting material is still much in evidence by TLC. The reaction mixture is again cooled and an additional equivalent of protected L-phenylalanine and an additional equivalent of ethyl diethylaminopropylcarbodiimide hydrochloride is added to the mixture and is stirred in the cold bath for 15 minutes. After setting in the refrigerator overnight the mixture is allowed to warm to room temperature for an additional one-half hour. TLC now shows very little starting material. After another two hours no starting material remains.

The reaction mixture is concentrated in a vacuum without heat. The residue is added to ethyl acetate (50 ml), cooled in an ice bath, washed with 4% NaHCO$_3$ (10 ml)/ice-water, then with 5% citric acid/ice-water (10 ml), then with ice-water (5 ml), and finally with brine (5 ml). The material is dried with MgSO$_4$ and concentrated to yield 0.21 g. of product. The aqueous layers from washing above are pooled, extracted with ethyl acetate (about 35 ml), dried with MgSO$_4$ but little product is found. The material is purified by chromatography on silica gel (50 ml), eluted with 3% MeOH/CH$_2$Cl$_2$ to 10% MeOH/CH$_2$Cl$_2$.

MS $[M+H]^+1042$; $[m.+K]^+1080.5204$.

The MS is consistent with the compound shown as the product of step V in Scheme IX.

Step VI:

The compound having the formula shown as the product of step V in Scheme IX and treated to remove the TBDMS group as prepared immediately above after step V, Scheme IX (0.05 g., 0.0001 mol) is dissolved in THF. HOBT (0.04 g., 0.0003 mol) is added to the solution and the resulting reaction mixture is stirred at room temperature. After five hours an aliquot is concentrated under a stream of N$_2$ and the residue placed in 10% MeOH/CH$_2$Cl$_2$ for a TLC with 5% MeOH/CH$_2$Cl$_2$ showing the starting compound prepared immediately after step V above still remains. The reaction mixture is stirred overnight. There is some precipitate. A repeated TLC still shows starting compound. Stirring is continued at room temperature. Another TLC with 10% MeOH/CH$_2$Cl$_2$ of an aliquot in 10% MeOH/CH$_2$Cl$_2$ still shows starting compound. Additional HOBT (0.02 g.) in 1 ml THF is added to the mixture and it is again stirred overnight. No starting compound remains in TLC when done as before.

The mixture is now concentrated under a stream of N$_2$. The residue is partitioned between about 50 ml cold ethyl acetate and 10 ml cold 4% NaHCO$_3$. The pooled aqueous layers are extracted twice with 25 ml ethyl acetate and the pooled organic layers are washed with about 10 ml brine, dried over $Na_2SO_4$, and concentrated to yield about 110 mg of compound having the formula $XX_5$ as shown in Scheme IX. Purification by silica gel chromatography and characterization by M.S. is consistent with the desired compound of formula $XX_5$. MS [m.+H]+888.

In a manner similar to the synthesis described in U.S. Pat. No. 4,424,207 using resin to facilitate the isosteric replacement of the peptide bond, the compound having the formula XX of the present invention may be synthesized for use as renin-inhibiting peptides. The following examples are, therefore, also included in the present disclosure but are not meant to be limiting.

Generally, it is suggested the procedures of the resin synthesis include the following:

Optical rotations are measured in a Perkin Elmer Mode 243 polarimeter. Solid phase synthesis is performed on an automated solid phase peptide synthesizer, Sun-Thor 1000. HPLC is performed on a Beckman chromatograph equipped with a Beckman Model 165 dual wavelength detector. It is monitored at 220, 254 and 280 nm using $H_2O$-$CH_3CN$ containing .1% $CF_3CO_2H$ at 1.5 ml/min. with linear gradient, increasing in $CH_3CN$ on a 4×250 mm, 5.1 μ column of synchropak RP-P. Amino acid analyses are performed on a Dionex D-500 amino acid analyzer, following hydrolysis in degassed 6 M HCl at 110° for 24 hours in vacuo. Thin layer chromatography loads of 50–80 μg are applied to precoated plates of silica gel 60 F-254 (Merck). It is developed for 10–12 cm in the following solvent system: A, BuOH-HOAc-$H_2O$-Py (15:3:12:10); B, BuOH-HOAc-$H_2O$ (4:1:1); C, $CHCl_3$-MeOH-HOAc-$H_2O$ (10:10:1:10).

45.

Example IX

Boc-Phe-His-Leuψ(CHOH-$CH_2$)Val-Ile-Phe-$NH_2$

N α-tert-butyloxycarbonyl-phenylalanine (0.52 g., 2 mmol), hydroxybenzyltriazole (HOBT, 0.24 g., 2 mmol) in 5 ml DMF, and dicyclohexylcarbodiimide (DCC, 0.4 g., 2 mmol) in 5 ml $CH_2Cl_2$ are added to the 0.6 g. of P-methylbenzhydrylamine resin (polystyren 0.1% divinylbenzene (cross-linked)) which was previously neutralized with 10% $Et_3N$ in $CH_2Cl_2$ (3×20 ml). This mixture is shaken mechanically until the ninhydrin test indicates completion of the reaction (0.52 mmol/g. substitution). Any unreacted sites are covered by acetylation, using 20 ml of 0.2 M acetic anhydride/$CH_2Cl_2$ in the presence of catalytic amounts (0.05 g.) of 4-dimethylaminopyridine and mixed for 30 minutes. Following Table I and using 20 ml volume of solvent in each step, Boc-Ile, Boc-Leuψ(CHOH-$CH_2$)Val, and Boc-Phe are coupled in a similar manner as above except using 1 mmol of each reagent. Coupling Boc-His(Tos) requires activation with BOP. After completion of the synthesis, the resin is dried in vacuo; the resin shows a weight gain of 0.48 g. (94%). The entire resin is treated with HF-anisol 9(10:1) for 1.0 hour at $0^9$ C. After evaporation, the residue is washed with $Et_2O$, extracted with $CF_3CO_2H$ (2×10 ml), and filtered. The filtrate is evaporated, the residue dissolved in 5% HOAc/$H_2O$, and lyophilized, resulting in 345 mg of crude material. This material is dissolved in 10 ml of 50% HOAc/$H_2O$ and applied to a 2×96 cm column of sephadex G-15 that had been equilibrated with 50% aqueous HOAc. The column is eluted with 50% HOAc and the eluate collected in 5.2 ml fractions. The peptide material is detected by monitoring the eluate at 280 nm and the fractions comprising the main peak are pooled, concentrated to 20 ml, diluted with $H_2O$ (60 ml) and lyophilized to give 209 mg. This is further purified by dissolving in 50% $CH_3CN$-$H_2O$ (0.1% TFA) and applying it to a 2.5×110 cm column of VYDAC-C18, 30μ that had been equilibrated with $H_2O$-$CH_3CN$ 70:30 (0.1% TFA). The column is eluted at 4.5 ml/minute beginning at 30% $CH_3CN$ and ending with a system containing 60% $CH_3CN$ (0.1% TFA) over an eight-hour period. The eluate is monitored at 206 nm and collected in 20 ml fractions. Fractions comprising the main peak are pooled, the $CH_3CN$ evaporated and diluted with $H_2O$/HOAc (10:1) and lyophilized, giving 120 mg of pure material (Phe-His-Leuψ(-CHOH-$CH_2$)Val-Ile-Phe-$NH_2$). HPLC on a Synchropak RP-P a 4.6×250 mm column in the system, $H_2O$-$CH_3CN$ containing 0.1% TFA beginning 30% $CH_3CN$ and going linearly to 60% $CH_3CN$ in 15 minutes at 1.5 ml/minute showed a single peak. Single spot TLC $R_f(A)$ 0.31, $R_f(B)$ 0.45. Amino acid analysis: Phe, 2.0; His, 0.97; Ile, 1.01.

30 mg of Phe-His-Leuψ(CHOH-$CH_2$)Val-Ile-Phe-$NH_2$ is dissolved in 5 ml of $H_2O$ and 3 ml of DMF. the pH of this solution is adjusted to 7.5 with addition of NaOH (0.1 N), followed by the addition of $(Boc)_2O$ (0.1 g.) and stirred for three hours while the pH is maintained at 7.5. The excess of $(Boc)_2O$ is extracted with hexane and the aqueous layer is acidified to pH 2.5 by the addition of HCl (0.1 N). This solution is lyophilized and purified by HPLC as previously described except the column is eluted at 4.5 ml/minute beginning at 50% $CH_3CN$ and ending with a system containing 85% $CH_3CN$ (0.1% TFA) over an eight-hour period. HPLC showed a single peak. Single spot TLC $R_f(A)$ 0.41, $R_f(B)$ 0.48. Amino acid analysis: Phe, 1.99; His, 1; Ile, 0.98. The mass spec is consistent for the above compound, Boc-Phe-His-Leuψ(CHOH-$CH_2$)Val-Ile-Phe-$NH_2$.

TABLE I

CONVENTIONAL SOLID-PHASE SYNTHESIS PROCEDURE

| Stop | Reagent | Repetition | Time (minutes) |
| --- | --- | --- | --- |
| 1 | $CH_2Cl_2$ | 5 | 0.8 |
| 2 | $CF_3CO_2H$/$CH_2Cl_2$(1:1)2% anisol | 2 | 5.0, 25.0 |
| 3 | $CH_2Cl_2$ | 4 | 0.8 |
| 4 | DIPEA/$CH_2Cl_2$ | 3 | 4.0 |
| 5 | $CH_2Cl_2$ | 3 | 0.8 |
| 6 | DMF | 2 | 0.8 |
| 7A | Boc-amino acid/HOBT in DMF | 1 | 90.0 |
| 7B | DCC in $CH_2Cl_2$ | 1 | — |
| 8 | DMF | 2 | 0.8 |
| 9 | $CH_2Cl_2$ | 2 | 0.8 |
| 10 | EtOH | 2 | 2.0 |

C46.

Example X

Tba-Phe-His-Leuψ(CHOH-$CH_2$)Val-Ile-Phe-$NH_2$ this peptide was prepared by two different methods. Both methods gave identical products.

METHOD A 30 mg of purified Phe-His-Leuψ(CHOH-$CH_2$)Val-Ile-Phe-$NH_2$ are dissolved in DMF and the pH adjusted to 7.5. One equivalent of each t-butylacetic acid, HOBT, and DCC are added and mixed. The reaction is followed by HPLC (synchropak RP-P, 4.6×250 mm column at 1.5 ml/minute in the system H₂O-CH₃CN containing 0.1% TFA using a gradient from 40–80% CH₃CN over a period of 20 minutes) and is judged complete when the starting pentapeptide can no longer be detected. This mixture is made acid, filtered, and concentrated by rotary evaporator. The residue is applied to 2.2×30 cm column of VYDAC-$C_{18}$ (20μ) which had been equilibrated with H₂O/CH₃CN 35:65 (0.1% TFA). The column is eluted at 4.5 ml/minute beginning at 65% CH₃CN and ending with a system containing 85% CH₃CN (0.1% TFA) over a five-hour period. The eluate is collected in 8 ml fractions and the fractions containing the main peak are pooled, the CH₃CN evaporated and aqueous solution diluted with H₂O/HOAc (10:1) and lyophilized; yield 15 mg. HPLC on the synchropak RP-P column in the system described above showed a single peak. Single spot TLC $R_f$(A) 0.48, $R_f$(B) 0.64. Amino acid analysis: Phe, 198; His, 1.0; Ile, 1.0. The mass spec was consistent for the above compound.

METHOD B

The title compound is also prepared by addition of t-butylacetic acid (0.22 g., 2 mmol) and dicyclohexylcarbodiimide (0.2 g., 1 to H-Phe-His-Leuψ(CHOH-CH₂)Val-Ile-NH-Resin (0.8 g., P-methylbenzhydrylamine Resin) as described in Table I. After completion, the resin is dried in vacuo, the entire batch is treated with 10 ml of HF-anisol (10:1) for 45 minutes at 0° C. After evaporation, the residue is washed with Et₂O, extracted with CF₃CO₂H (2×10 ml), and filtered. The filtrate is evaporated, the residue dissolved in 15% HOAc/H₂O, and lyophilized, resulting in 275 mg of crude material. This material is dissolved in 10 ml of 50% HOAc-H₂O and applied to a 2×96 cm column of sephadex G-15 that had been equilibrated with 50% aqueous HOAc; the column is eluted with 50% HOAc and the eluate collected in 5.0 ml fractions. The peptide material is detected by monitoring the eluate at 280 nm and the fractions comprising the main peak are pooled, concentrated to 20 ml, diluted with H₂O (60 ml) and lyophilized to give 115 mg. This is further purified by dissolving in 60% CH₂CN-H₂O (0.1% TFA) and applying it to 2.5×110 cm column of VYDAC-$C_{18}$ that had been equilibrated with H₂O-CH₃CN 40:60 (0.1% TFA). The column is eluted at 3.0 ml/minute, beginning at 40% CH₃CN and ending with a system containing 85% CH₃CN (0.1% TFA) over a 16-hour period. The eluate is monitored at 206 nm and collected in 20 ml fractions. The main peak is pooled, the CH₃CN evaporated and diluted with H₂O/HOAc (10:1) and lyophilized to give 63 mg of pure material. HPLC on a synchropak RP-P column in the system described above showed a single peak identical to product prepared by Method A. Amino acid analysis, TLC results also indicated that both methods produce the same product.

Examples of a reaction sequence for the preparation of compounds of formula $XX_{10}$ disclosed herein follows.

C47.

Preparation $XX_{10}I$

Boc-Ile-Phe-OCH₃

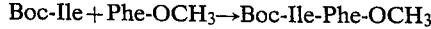

Add 2.80 g (13.0 mmoles) of Phe-OCH₃.HCl to 1.34 g (13.2 mmoles) of Et₃N and 100 ml of CH₂Cl₂. To this add 3.00 g (13.0 mmoles) of Boc-Ile, 1.98 g (13.0 mmoles) of 1-HOBT, and lastly, 2.68 g (13.0 mmoles) of DCC. After stirring for 1 hour and 40 minutes at room temperature, DCU is filtered off. Extract the filtrate with aq. NaHCO₃, 1M citric acid, and again with aq. NaHCO₃. *Filter the organic layers through* Na₂SO₄ and remove the solvent in vacuo. Chromatograph the crude product on silica gel, eluting with a gradient of 20% to 40%. EtOAc/hexane. The product, Boc-Ile-Phe-OCH₃, is crystallized from EtOAc-hexane to give 4.31 g (85%) of product m.p. 121–122°. Calc. for $C_{21}H_{32}N_2O_5$: C, 64.26; H, 8.22; N, 7.14. Found: C, 64.27; H, 8.32; N, 7.14.

C48.

Preparation $XX_{10}II$

Boc-Sta-Ile-Phe-OCH₃

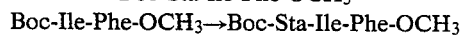

Boc-Ile-Phe-OCH₃, as prepared in Preparation $XX_{10}I$ above, (0.713 g, 1.82 mmoles) is stirred at room temperature in 10 ml of TFA-CH₂Cl₂ (1:1 v/v) for 30 minutes, after which TFA and CH₂Cl₂ are removed in vacuo and the residue is extracted with CH₂Cl and aq. NaHCO₃. The organic layers (total volume approx. 50 ml) are filtered through Na₂SO₄ into a flask containing 0.500 g (1.82 mmoles) of Boc-Sta, and 0.292 g (1.91 mmoles) of 1-HOBT. DCC (0.393 g, 1.91 mmoles) is then added. After stirring 1 hour at room temperature, DCU is filtered off and the filtrate is extracted with aq. NaHCO₃. The organic layers are filtered through Na₂SO₄, concentrated, and applied to a silica gel column. The product is eluted with 4% MeOH-96% CH₂Cl₂ *to give* 0.97 g (97%) of the product Boc-Sta-Ile-Phe-OCH₃.

Calc for $C_{29}H_{47}N_3O_7$: C, 63.36; H, 8.62; N, 7.64. Found: C, 63.81; H, 8.70; N, 7.52.

FAB mass spec.: [M+H] at m/z 550.

C49.

Preparation $XX_{10}III$

Boc-His-(Tos)-Sta-Ile-Phe-OCH₃

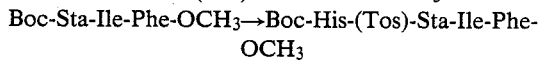

Stir 0.40 g (0728 mmoles) of Boc-Sta-Ile-Phe-OCH₃, as prepared in Preparation $XX_{10}II$ above, in 6 ml of TFA-CH₂Cl₂ (1:1 v/v) at room temperature for 30 minutes. Remove the solvent in vacuo and extract the residue with CH₂Cl₂ *and aq. NaHCO₃*. Filter the organic layers through Na₂SO₄ into a flask containing 0.42 g (1.02 mmoles) of Boc-His-(Tos), concentrate the solution to a volume of about 25 ml, and add 0.21 g (1.02 mmoles) of DCC. Stir for 40 minutes, then add 1 drop of HOAc and filter off DCU. Extract the filtrate with aq. NaHCO₃, filter the organic layers through Na₂SO₄, and remove the solvent in vacuo. The crude product is applied to a silica gel chromatography column and the product is eluted with 4% MeOH-96% CH₂Cl₂ to give 0.566 g (93%) of Box-His(Tos)-Sta-Ile-Phe-OCH₃.

Rf (8% MeOH-91.8% CH₂Cl₂-0.2% NH₄OH): 0.64.

FAB mass spec.: [M+H]⁺ at m/z 841.

¹H-NMR(CDClhd 3): δ0.73–0.94, m; 1.42, s; 2.43, s; 293, d; 3.10, d; 3.70, s; 603, d; 6.56, d; 6.75–6.95, m.

C50.

Preparation XX₁₀IV

Boc-His-Sta-Ile-Phe-OCH₃

A mixture of 0.206 g (0.245 mmoles) of III above Boc-His(Tos)-Sta-Ile-Phe-OCH₃, as prepared in Preparation XX₁₀III above, 0.187 g (1.22 mmoles) of 1-HOBT, and 15 ml of THF is stirred overnight at room temperature. The solvent is then removed in vacuo and the residue is extracted with CHCl₃ and aq. NaHCO₃. The organic layers are filtered through Na₂SO₄, concentrated, and applied to a silica gel chromatograph column. The product is eluted off the column with 8% MeOH-CH₂Cl₂ (91.9%) 0.1% NH₄OH to give 0.149 g (89%) of product, Boc-His-Sta-Ile-Phe-OCH₃, Rf=0.5 in 8% MeOH. 91.8% CH₂Cl₂-0.2% NH₄OH.

C51.

Preparation XX₁₀V

Boc-Ile-AMP

Boc-Ile+2-(aminomethyl)pyridine→Boc-Ile-AMP

Stir 3.15 g (13.6 mmoles) of Boc-Ile, 2.08 g (13.6 mmoles) of 1-HOBT, and 1.34 g (12.3 mmoles) of 2-(aminomethyl)pyridine in 150 ml of CH₂Cl₂ for 10 minutes. Add 2.81 g (13.6 mmoles) of DCC and stir at room temperature for 35 minutes, then filter off DCU. Extract the filtrate with aq. NaHCO₃, filter the organic layers through Na₂SO₄, and concentrate. Filter off DCU again, then chromatograph the crude production silica gel, eluting with 4% MeOH-CH₂Cl₂, to obtain 3.94 g (100%) of product. The product, Boc-Ile-AMP, is crystallized from EtOAc-hexane to give a first crop of 2.28 g with a m.p. of 102°–103.5°. Second and third crops totalling 1.50 g are also collected. Calc. for C₁₇H₂₇N₃O₃: C, 63.52; H, 8.47; N, 13.07. Found: C, 63.37; H, 8.55; N, 12.86.

C52.

Preparation XX₁₀VI

Boc-Sta-Ile-AMP Boc-Ile-AMP→Boc-Sta-Ile-AMP

Stir 1.60 g (4.98 mmoles) of Boc-Ile-AMP as prepared in Preparation XX₁₀V above in 20 ml of TFA-CH₂Cl₂ (1:1 v/v) at room temperature for 30 minutes. Remove TFA-CH₂Cl₂ in vacuo and extract the residue exhaustively with CH₂Cl₂ and aq. NaHCO₃-brine. Filter the organic layers through Na₂SO₄ and remove the solvent in vacuo. Add 30 ml of CH₂Cl₂ to the residue, then add 1.43 g (5.23 mmoles) of Boc-Sta, followed by 1.08 g (5.23 mmoles) of DCC. Stir overnight at room temperature, then add 30 mg of Boc-Sta and 30 mg of DCC. Stir an additional one hour, then filter off DCU. Extract the filtrate with water, filter the organic layers through Na₂SO₄, and concentrate in vacuo. Chromatograph the crude product on silica gel using first 4% MeOH-CH₂Cl₂ and then 6% MeOH-CH₂Cl₂-0.2% NH₄OH to obtain 2.16 g (91%) of product, Boc-Sta-Ile-AMP. Calc for C₂₅H₄₂N₄O₅: C, 62.73; H, 8.85; N, 11.71. Found: C, 62.37: H, 8.82; N, 11.71.

FAB mass spec.: [m+H]⁺ m/z 479.

C53.

Preparation XX₁₀VII

Boc-His(Tos-Sta-Ile-AMP

Boc-Sta-Ile-AMP→Boc-His(Tos)-Sta-Ile-AMP

Stir Boc-Sta-Ile-AMP (0.73 g, 1.52 mmoles) at room temperature in 10 ml of TFA-CH₂Cl₂ (1:1 v/v) for 30 minutes, then remove TFA and CH₂Cl₂ in vacuo. Extract the residue exhaustively with CH₂Cl₂ and aq. NaHCO₃-brine. Filter the organic layers through Na₂SO₄ and remove the solvent in vacuo. To the residue add 0.81 g (1.98 mmoles) of Boc-His(Tos) and 20 ml of CH₂Cl₂. Add 0.41 g (1.98 mmoles) of DCC and stir for two and one-half hours at room temperature. Filter off DCU and extract the filtrate with aq. NaHCO₃-brine. Filter the organic layers through Na₂SO₄, concentrate and chromatograph the crude product on silica gel, eluting with 8% MeOH-CH₂Cl₂-0.2% NH₄OH. Rechromatograph on silica gel using 6% MeOH (saturated with NH₃)-EtOAc to give 0.53 g (45%) of product, Boc-His(Tos)-Sta-Ile-AMP.

¹H-NMR(CDCl₃): δ0.70–0.97, m; 1.43, s; 1.84, s; 2.43, s; 2.93, d; 4.33, m; 4.57, d; 6.10, d; 6.9–8.5, m.

C54.

Preparation XX₁₀VIII

O-Acetyl-L-Phenyllactic Acid L-(−)-3-phenyllactic acid→O-acetyl-L-phenyllactic Acid A mixture of 0.09 g (0.54 mmoles) of L-(−)-3-phenyllactic acid, 0.2 ml of pyridine, and 0.2 ml of acetic anhydride is stirred at room temperature for one and one-half hours, after which it is extracted with CH₂Cl₂ and 3N HCl. The organic layers are filtered through Na₂SO₄ and the solvent is removed in vacuo to give 0.11 g (100%) of product, O-acetyl-L-phenyllactic acid.

Rf in 4% MeOH-95% CH₂Cl₂-1% HOAc is 0.32.

¹H-NMR (CDCl₃): δ2.07, s, 3H; 3.10, 3.15, 3.21, m, 2H; 5.25, m, 1H; 7.27, s, 5H; 8.66, bs, 1H.

C55.

Preparation XX₁₀IX

O-tert-Butylacetyl-L-phenyllactic Acid L-phenyllactic acid→O-tert-butylacetyl-L-phenyllactic acid Stir 0.100 g (0.602 mmoles) of L-phenyllactic acid, 0.128 g (1.26 mmoles) of Et₃N, and 0.0073 g (0.06 mmoles) of 4-dimethylaminopyridine in 15 ml of CH₂Cl₂. Add 0.170 g (1.26 mmoles) of tert-butylacetic acid chloride, stir at room temperature for 2 hours, then extract with CH₂Cl₂ and 1N HCl. Filter the organic layers through Na₂SO₄ and remove the solvent in vacuo. Chromatograph the residue on silica gel using first 4% MeOH-96% CH₂Cl and then 8% MeOH-CH₂Cl₂-0.2% HOAc to obtain 0.065 g (41%) of product, O-tert-butylacetyl-L-phenyllactic acid (Rf in 8% MeOH CH₂Cl₂-0.2% HOAc: 0.35)

¹H-NMR(CDCl₃): δ0.81, s, 0.83, s; 2.12, s; 3.1, m; 5.15, m; 6.17, bs; 7.19, s.

C56.

Preparation XX₁₀

O-Acetyl-L-Phenyllactyl-His-Sta-Ile-Phe-OCH₃
Boc-His-Sta-Ile-Phe-OCH₃→OAcetyl-L-phenyllactyl-His-Sta-Ile-Phe-OCH₃

Boc-His-Sta-Ile-Phe-OCH₃, as prepared in Preparation XX₁₀IV above (0.149 g, 0.217 mmoles) is stirred in 15 ml of TFA-CH₂Cl₂ (1:1 v/v) at room temperature for 30 minutes, after which the TFA and CH₂Cl₂ are removed in vacuo. The residue is extracted with CHCl₃ and aq. NaHCO₃ and the organic layers are separated and filtered through Na₂SO₄. The solvent is removed in vacuo and the residue is dissolved in 10 ml of CH₂Cl₂. To this is then added 0.50 g (0.239 mmoles) of O-acetyl-L-phenyllactic acid, as prepared in Preparation XX₁₀III above, followed by 0.049 g (0.239 mmoles) of DCC. The reaction is stirred overnight. Precipitated DCU is then filtered off and the filtrate is concentrated and then applied to a silica gel chromatograph column. The product is eluted with the solvent system 6% MeOH-93% CH₂Cl₂-0.1% NH₄OH to give, after solvent is removed in vacuo, 0.122 g (73%) of product, O-acetyl-L-phenyllactyl-His-Sta-Ile-Phe-OCH₃.

Rf in 6% MeOH-93% CH₂Cl₂-0.1% NH₄₀H: 0.27.
FAB mass spec. [m+H]⁺ at m/z 777.
¹H-NMR (CDCl₃): δ0.76–0.92, m; 2.18, s, CH₃CO-; 3.70, s, —OCH₃; 6.5–7.5, m.
HPLC: LiChrosorb C₁₈, 40% CH₃CN (0.2% TFA)/60% H₂O (0.2% TFA); λ225, k=8.0.

C57.

Preparation XX₁₀II

O-tert-butylacetyl-L-phenyllactyl-His-Sta-Ile-AMP

Boc-His(Tos)-Sta-Ile-AMP→O-Tert-butylacetyl-L-phenyllactyl-His-Sta-Ile-AMP

Boc-His(Tos)-Sta-Ile-AMP as prepared in Preparation XX₁₀VII above (0.172 g, 0.224 mmoles) is stirred at room temperature in 15 ml of TFA-CH₂Cl₂ (1:1 v/v) for 30 minutes. TFA and CH₂Cl₂ are then removed in vacuo and the residue is extracted with CH₂Cl₂ and aq. NaHCO₃. Filter the organic layer through Na₂SO₄, concentrate to 10 ml, and add 0.065 g (0.246 mmoles) of O-tert-butylacetyl-L-phenyllactic acid, as prepared in Preparation XX₁₀IX above, followed by 0.051 g (0.246 mmoles) of DCC. After stirring for 45 minutes, add 0.38 g (2.46 mmoles) of 1-HOBT. Stir the reaction for 24 hours and then extract with CH₂Cl₂ and aq. NaHCO₃. Filter the organic layers through Na₂SO₄, concentrate, and filter off DCU. Chromatograph the crude product (filtrate) on silica gel, eluting with 8% MeOH-91.8% CH₂Cl₂-0.2% NH₄OH to obtain 0.041 g (24%) of product, O-tert-butylacetyl-L-phenyllactyl-His-Sta-Ile-AMP.

FAB mass spec.: [M+H]⁺ at m/z 762.
¹H-NMR(CDCl₃): δ0.63–0.81, m; 0.89, s; 5.15, m; 6.45, bd; 6.75–8.5, m; 7.24, s.

C58.

Preparation XX₁₀III

O-acetyl-L-phenyllactyl-His-Sta-Ile-AMP
Boc-His-Sta-Ile-AMP→O-acetyl-L-phenyllactyl-His-Sta-Ile-AMP Stir 0.035 g (0.057 mmoles) of Boc-His(Tos)-Sta-Ile-AMP as prepared in Preparation XX₁₀VII above and 4 ml of TFA-CH₂Cl₂ (1:1 v/v) at room temperature for 20 minutes, then remove TFA and CH₂Cl₂ in vacuo. To the residue add 0.05 g (0.05 mmoles) of Et₃N and 20 ml of CH₂Cl₂. Stir for several minutes, then remove excess Et₃N and CH₂Cl₂ in vacuo. To the residue add 0.0142 g (0.068 mmoles) of O-acetyl-L-phenyllactic acid, as prepared in Preparation XX₁₀VIII above, and 5 ml of CH₂Cl₂, followed by 0.0142 g (0.068 mmoles) of DCC and 0.25 ml of DMF. Stir at room temperature for 21 hours, then remove CH₂Cl₂ and DMF in vacuo. Add CH₂Cl₂ to the residue and filter off DCU. Extract the filtrate with CH₂Cl₂ and aq. NaHCO₃. Filter the organic layers through Na₂SO₄, concentrate, and chromatograph on silica gel using 8% MeOH-CH₂Cl₂-0.3% NH₄OH to obtain 0.0231 g (58%) of product, O-acetyl-L-phenyllactyl-His-Sta-Ile-AMP.

Rf (8% MeOH-CH₂Cl₂-0.2% NH₄OH): 0.36.
¹H-NMR (CDCl₃): δ0.62–1.0, m; 2.17, s; 4.56, d; 5.10, m; 6.43, bd; 7.26, s; 6.7–8.5, m.
HPLC: μBondapak Phenyl column; 25% CH₃CN(0.2% TFA)/75% H₂O (0.2% TFA), k¹=4.0; λ225.

C59.

Preparation XX₁₀IV

L-Phenyllactyl-His-Sta-Ile-AMP
Bos-His-Sta-Ile-AMP→L-Phenyllactyl-His-Sta-Ile-AMP Stir 0.050 g (0.0812 mmoles) of Boc-His(Tos)-Sta-Ile-AMP, as prepared in Preparation XX₁₀VII above in 4 ml of TFA-CH₂Cl₂ (1:1 v/v) at room temperature for 20 minutes, then remove TFA and CH₂Cl₂ in vacuo. Add 0.5 ml of DMF to the residue, followed by 0.0247 g (0.243 mmoles) of Et₃N. To this, add 0.0148 g (0.0893 mmoles) of L-phenyllactic acid, 5 ml of CH₂Cl₂, and finally 0.0184 g (0.0893 mmoles) of DCC. After one hour, add an additional 0.0074 g of L-phenylactic acid and 0.0092 g of DCC. Stir 3 hours, then remove CH₂Cl₂ and DMF in vacuo. Add CH₂Cl₂ to the residue and filter off DCU. Concentrate the filtrate and apply it to a silica gel column. Elute the product with 8% MeOH-CH₂Cl₂-0.3% NH₄OH. Combine product fractions and rechromatograph on two waters C18 Sep Paks (in series) using a gradient of H₂O→10% MeOH-H₂O→30% MeOH-H₂₀ →66% MeOH-H₂O. (The product comes off with the 66% MeOH-H₂₀ solvent concentration.) The product fractions are combined, MeOH is removed in vacuo, and the remainder is lyophilized to give 0.0298 g (55%) of U-71,095.

Rf (8% MeOH-CH₂Cl₂-0.2% NH₄OH): 0.26.
¹H-NMR (CDCl₃-MeOH-d₄): δ0.65–0.96, m; 2.95, m; 4.5, m; 6.75–8.4, m; 7.25, s.
HPLC: μBondapak Phenyl column, 22% CH₃CN (0.2% TFA)/78% H₂O (0.2% TFA), k¹=6.7; λ225.

Additional compounds of the present invention can also be made by methods analogous to those described above. For example, it has been found the MS for the following compounds is consistent with the indicated structure:

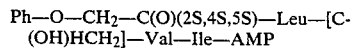

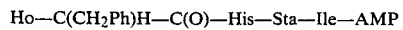

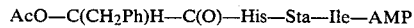

POA—His(2S,4R,5S)—Leu—[C(OH)HCH$_2$]—Val—Ile—Phe—OCH$_3$

POA—His(2S,4R,5S)—Leu—[C(OH)HCH$_2$]—Val—Ile—AMP.

C60.

Preparation XL$_{6c}$

Part A

To a stirred solution of 463 mg (2.43 mmol) of BOC-leucinol in 2 ml of tetrahydrofuran at −78° C. under argon is added 2.4 mL (2.4 mmol) of a 1 M solution of lithium bis(trimethylsilyl)amide in tetrahydrofuran. After 10 minutes, 0.3 ml (4.8 mmol) of methyliodide was added and the resulting mixture is allowed to warm to room temperature. It is then heated to reflux for 1 hour and then cooled. The mixture is partitioned between 40 ml of dichloromethane and 30 ml portions of dichloromethane. The combined residue is chromatographed on silica gel with 15% ethyl acetate in hexane to give 405 mg (1.75 mmol, 83%) of BOC-leucinol methyl ether. $^1$H-NMR (CDCl$_3$): δ0.9 d (d, d×3H, J=6 Hz), 1.44, 3.33.

Part B

By the same procedure as in the preparation of BOC-leucinol methyl ether (Part A), 280 mg (1.29 mmol) of BOC-isoleucinol in 1.3 of tetrahydrofuran is treated with 1.3 ml (1.3 mmol) of a 1M solution of lithium bis(trimethylsilyl)amide in tetrahydrofuran and 0.4 ml (0.4 mmol) of methyl iodide, affording 245 mg (1.06 mmol, 82%) of BOC-isoleucinol methyl ester after chromatography on silia gel with 15% ethyl acetate in hexane. $^1$H-NMR (CDCl$_3$): δ0.89, 0.91, 1.44, and 3.41.

Part C

A solution of 38.4 mg (0.086 mmol) of BOC-leu-(CHOTBSCH$_2$)val-OH in 0.35 ml of a 1M borane in tetrahydrofuran (0.35 mmol) is allowed to stir at room temperature for 5 hours. It is then treated dropwise with 0.35 ml of 1M aqueous NaOH. After 30 minutes, the resulting mixture is partitioned between 40 ml of dichloromethane and 5 ml of saturated aqueous NaHCO$_3$. The aqueous phase is extracted with four 5 ml portions of dichloromethane. The combined organic phase is dried (MgSO$_4$), filtered, and then concentrated. The resulting residue is chromatographed on silica gel with 20% ethyl acetate in hexane to give 24.7 mg (0.057 mmol, 66%) of the alcohol. $^1$H-NMR (CDCl$_3$): δ0, 0.81, and b 4.35.

Part D

By the same procedure as in the prearation of BOC-leucinol methyl ether (Part A), 24.7 mg (0.057 mmol) of the alcohol (Part C) in 0.4 ml of tetrahydrofuran with 0.06 ml (0.06 mmol) of a 1M solution of lithium bis(trimethylsilyl)amide in tetrahydrofuran and 0.02 ml (0.32 mmol) of methyliodide affords 19 mg (0.043 mmol, 75%) of the corresponding methyl ether after chromatography on silica gel with 10% ether in hexane. $^1$H-NMR (CDCl$_3$): δ0, 0.81, 1.36, and 3.19.

C61.

Preparation NLA$^1$

Part A

L-3-(1-Naphthyl)lactic acid

To a suspension of 0.154 g (0.71 mmoles) of L-3-(1-naphthylalamine) in 50 ml of 2.5N H$_2$SO$_4$ is added NaNO$_2$ (0.2 g) in small aliquots over 8 days. The reaction mixture is then extracted with Et$_2$O, water, and brine. The organic layers are filtered through Na$_2$SO$_4$ and taken to dryness to give 0.069 g (45%) of product. Rf=0.10.

Part B

O-Ac-L-3-(1-Naphthyl)lactic acid

A mixture of 0.038 g (0.176 mmoles) of the compound of Part A, 0.2 ml of pyridine, and 0.2 ml of acetic anhydride is stirred at room temperature for 3 hours. The reaction mixture is then extracted with CH$_2$Cl$_2$ and 1N HCl (2X) and the organic layers are filtered through Na$_2$SO$_4$, concentrated, and chromatographed on silica gel with 4% MeOH —CH$_2$Cl$_2$—0.1% HOAc to give 0.0383 g (84%).

NMR (CDCl$_3$): δ2.00, 3.3–3.9, 5.29–5.45, 7.37–8.16, and 8.33.

RF=0.36.

Part C

To 0.084 g (0.147 mmoles) of His(Tos)-Leuψ[C-H(OH)CH$_2$]-Val-Ile-AMP, 0.038 g (0.147 mmoles) of the compound from part B, O-Ac-3-(1-naphthyl)lactic acid, 0.020 g (0.147 mmoles) of 1-HOBT, 5 ml of CH$_2$Cl$_2$, and about 5 drops of DMF is added 0.030 g (0.147 mmoles) of DCC. After 35 minutes an additional 0.04 g of 1-HOBT is added. After stirring overnight the solvents are removed in vacuo and the residue is extracted with CHCl$_3$-CH$_2$Cl$_2$ and aq NaHCO$_3$. The organic layers are concentrated and chromatographed on silica gel using 8% MeOH-CH$_2$Cl$_2$. The fractions containing tosylated material were re-subjected to 1-HOBT in CH$_2$Cl$_2$ and THF and rechromatographed to give a total of 0.0527 g product.

FAB mass spec: [m+H] at m/z 812.

NMR (CDCL$_3$): δ2.01.

RF=0.14.

The following preparations exemplify compounds of the present invention.

C62.

Preparation XX$_{10}$H$_4$ (2S,4S,5S)Leu-Ψ-[CH(OTBDMS)CH$_2$]-Va;-Ile-AMP

A peptide of formula Boc(2S,4S,5S)Leu-Ψ-[CH(OTBDMS)CH$_2$]-Val-Ile-AMP (0.39 g.; 0.000600 mol.) prepared by methods analogous to those described above is dissolved in CH$_2$Cl$_2$ (2 ml.) under N$_2$. The solution is cooled in an ice bath. Tri-fluoroacetic (2 ml) acid is added dropwise to the solution over 2 minutes. The cooled solution is stirred for 10 minutes and then removed from the ice bath. Stirring is continued at room temperature for thirty minutes. TLC in 5% MeOH:CH$_2$Cl$_2$ shows the reaction is complete. After 45 minutes at room temperature, 0.285 g of product, (2S,4S,5S)-Leu-Ψ-[CH(OTBDMS)CH$_2$]-Val-Ile-AMP having a melting point of 134°–138° C. is obtained after a conventional work up.

C63.

Preparation XXH₃

Boc-im-tosyl-His(2S,4S,5S)-Leu-Ψ-[CH(OTBDMS)CH₂]-Val-Ile-AMP

The compound, (2S,4S,5S)-Leu-Ψ-[CH(OTBDMS)CH₂]-Val-Ile-AMP (0.10 g, 0.000182 mol.) prepared in Preparation $XX_{10}H_4$ above, is dissolved in CH₂Cl₂ (4 ml.) under N₂. Boc-im-tosyl-histidine (0.075 g.; 0.000182 mol. 1 equiv.) is added to the solution followed by the addition of diisopropylethylamine (0.0565 g., 0.076 ml, 0.00043 mol., 2.4 equiv.) and 2-chloro-1-methylpyridium iodide (0.056 g., 0.000219 mol., 1.2 equiv.). The resulting mixture is heated to reflux in an oil bath at 50° for 10 minutes and held at reflux temperature for 1 hour. The mixture is allowed to cool and is stirred at room temperature. The reaction mixture is spotted on two TLC plates and run in 5% MeOH:CH₂Cl₂ with 0.5 NH₄OH. One plate is developed with ninhydrin and the other with I₂. The reaction is complete showing a single product spot. 0.174 g of product Boc-im-tosyl-His(2S,4S,5S)-Leu-Ψ-[CH(TBDMS)CH₂]-Val-Ile-AMP is obtained after conventional work up procedures. The NMR of the product is consistent with the structural formula expected.

C64.

Preparation $XX_{10}H_2$ im-tosyl-His-(2S,4S,5S)-Leu-Ψ-[CH(OH)CH₂]-Val-Ile-AMP The protected peptide as prepared in Preparation $XX_{10}H_3$ above, Boc-im-tosyl-His-(2S,4S,5S)-Leu-[CH(OTBDMS)CH₂]-Val-Ile-AMP, is dissolved in CH₂Cl₂ (1 ml) under N₂ and cooled in an ice bath. Trifluoroacetic acid (1ml) is added dropwise to the solution over a one minute time interval. The reaction mixture is removed from the cold bath and stirred at room temperature for 1 hour and 5 minutes. The reaction mixture is poured into 15 ml of saturated aqueous NaHCO₃, cooled by an ice bath. After conventional extraction and purification, 0.089 g of product, im-tosyl-His(2S,4S,5S)-Leu-Ψ-[CH(OH)CH₂]-Val-Ile-AMP is obtained. HPLC is consistent with product structure.

C65.

Preparation $XX_{10}H_1$

Step A: O-Acetylphenyllactic Acid (Ac-PLA)

Phenyllacetic acid (0.75 g) is dissolved in pyridine under N₂ and the solution is cooled in an ice bath. Acetic anhydride (2.0 ml) is added dropwise over 1.5 min. The reaction mixture is removed from the ice bath and stirred at room temperature for 1 hour and 50 minutes. TLC in 4% MeOH:CH₂Cl₂ with 0.5% AcOH shows the reaction is complete. After 1 hour and 50 minutes the titled product, is extracted from the reaction mixture and purified by conventional methods to obtain 0.741 g. thereof. The NMR is consistent with the desired structure.

Step B Ac-PLA im-tosyl-His(2S,4S,5S)-Leu-Ψ-[CH(OTBDMS)CH₂]-Val-Ile-AMP

The amine, im-Tosyl-His(2S,4S,5S)-Leu-Ψ-(CH(OH)CH₂]-Val-Ile-AMP as prepared in Preparation $XX_{10}H_2$ above, (0.085 g., 0.000117 mol.) is dissolved in CH₂Cl₂ (5 ml.) under N₂. A cloudy solution is formed. The Ac-PLA (0.0244 g., 0.000117 mol., 1 equiv.) as prepared in Preparation $X_X1_0H_1$ Step A above is added and the mixture rinsed with a small additional amount of CH₂Cl₂ to form a clear solution. Diisopropyl-ethylamine (0.036 g., 0.049 ml., 0.000281 mol., 2.4 equiv.) is added followed by the addition of 2-chloro-1-methylpyridinium iodide (0.036 g., 0.000141 mol., 1.2 equiv.). The mixture is heated to reflux temperature and maintained for 1 hour and 10 minutes. The mixture is removed from the heat and allowed to cool to room temperature. TLC in 5% MeOH:CH₂Cl₂ with 0.5% NH₄OH and developed with I₂ shows the reaction is complete. Extraction and purification by conventional methods yields 0.097 g. of the product, Ac-PLA im-tosyl-His-(2S,4S,5S)-Leu-Ψ-[CH(OH)CH₂]-Val-Ile-AMP. The NMR is consistent with the desired product.

C66.

Preparation $XX_{10}H$

Ac PLA-His-(2S,4S,5S)-Leu-Ψ-[CH(OH)CH₂)-Val-Ile-AMP

The protected peptide, Ac PLA im-tosyl-His-(2S,4S,5S)-Leu-[CH(OH)CH₂]-Val-Ile-Amp as prepared in Preparation $XX_{10}H_1$ (0.095 g., 0.000104 mol.) is dissolved in THF (5 ml.) under N₂ and then DMF (1 ml.) is added. The resulting mixture is stirred until a solution is obtained. Then HOBT (0.14 g., 0.00104 mol., 10 equiv.) is added and the resulting mixture stirred at room temperature for 25 hours. TLC in 5% MeOH:CH₂Cl₂ with 0.5% NH₄0H is carried out on a plate and developed with I₂. The TLC shows the reaction is complete. Concentration of the reaction mixture on a rotary evaporator and removal of the DMF with a vacuum pump gives 0.073 g. of product, Ac-PLA-His(2S,4S,5S)-Leu-Ψ-[CH(OH)CH₂]-Val-Ile-AMP.

MS, theory for $C_{41}H_{60}N_2O_7[M+H]_+$: 762.4554. Found: 762.4521.

The compound $XX_{10}H_1$, H-PLA-His-(2S,4S,5S)-Leu-Ψ-[CH(OH)CH₂]-Val-Ile-AMP, is prepared by treating in ice cold methanol solution of the product of Preparation $XX_{10}H$ above, Ac-PLA-His-(2S,4S,5S)-Leu-Ψ-[CH(OH)-CH₂]-Val-Ile-AMP, with anhydrous ammonia and allowing the mixture to stand at ambient temperature for 20 hours.

MS, theory for $C_{39}H_{58}N_7O_6[M+H]_+$: 720.4448. Found: 720.4456.

It has also been found that the MS for each of the following compounds is consistent with the indicated structure:

Ph-O-CH₂—C(O)(2S,4S,5S)-Leu-[C(OH)HCH₂]-Val-Ile-AMP

POA-His(2S,4R,5S)-Leu-[C(OH)HCH₂]-Val-Ile-Phe-OCH₃

POA-His(2S,4R,5S)-Leu-[C(OH)HCH₂]-Val-Ile-AMP.

Additional compounds of the present invention can also be made by methods analogous to those described above. For example, the following compounds are within the scope of this invention:

Ph-O-CH₂—C(O)(2S,4S,5S)-Leu-[C(OH)HCH₂]-Val-Ile-AMP

Ho-C(CH₂Ph)H—C(O)-His-Sta-Ile-AMP

AcO-C(CH$_2$Ph)H—C(O)-His-Sta-Ile-AMP

POA-His(2S,4R,5S)-Leu-[C(OH)HCH$_2$]-Val-Ile-Phe-OCH$_3$

POA-His(2S,4R,5S)-Leu-[C(OH)HCH$_2$]-Val-Ile-AMP.

C67.

Preparation XX$_{20}$I$_1$

N-tert-Butyloxycarbonyl-L-isoleucyl-2-pyridylmethylamide XX$_{20}$I$_1$

To a stirred solution of 4.68 g (45.4 mmol) of 2-aminomethylpyridine (XX$_{20}$I$_2$), 10.0 g (43.2 mmol) of N-tert-butyloxycarbonyl-L-isoleucine, and 5.84 g (43.2 mmol) of 1-hydroxy-benzotriazole in 100 ml of dichloromethane is added 8.92 g (43.2 mmol) of dicyclohexylcarbodiimide. After stirring at room temperature for 16 h, the reaction mixture is partitioned between dichloromethane and saturated aqueous NaHCO$_3$. The aqueous phase is further extracted with two portions of dichloromethane. The combined organic phase is dried (MgSO$_4$), filtered, and then concentrated. The residue is chromatographed on silica gel with ethyl acetate to give 13.9 g (42.6 mmol, 98%) of the amide, N-tert-Butyloxycarbonyl-L-isoleucyl-2-pyridylmethylamide XX$_{20}$I$_1$, structure of which was supported by $^1$H-NMR and elemental analysis (calcd. for C$_{17}$H$_{27}$N$_3$O$_3$: C, 63.53; H, 8.47; N, 13.97; found: C, 63.73; H, 8.44; N, 13.00).

C67A.

Preparation XX$_{20}$I

5S-N-tert-Butyloxycarbonylamino-2S-isopropyl-7-methyl-4S-tert-butyldimethylsilyloxy-octanoyl-L-isoleucyl-2-pyridylmethylamide (XX$_{20}$I)

To a stirred solution of 65 mg (0.29 mmol) of L-isoleucyl-2-pyridylmethylamide (from treatment of the amide having the formula XX$_{20}$I$_1$, as prepared above with 1:1=trifluoroacetic acid dichloromethane and then neutralization with aqueous NaHCO$_3$), 100.5 mg (0.226 mmol) of 5S-N-tert-butyloxycarbonylamino-2S-isopropyl-7-methyl-4S-tert-butyldimethylsilyloxy-octanoic acid, and 35 μl (0.29 mmol) of diethylphosphoryl cyanide. After stirring at room temperature for 16 h, the reaction mixture is partitioned between dichloromethane and saturated aqueous NaHCO$_3$. The aqueous phase is further extracted with two portions of dichloromethane. The combined organic phase is dried (MgSO$_4$), filtered, and then concentrated. The resulting residue is chromatographed on silica gel with 60% ethyl acetate in hexane to give 137.3 mg 90.212 mmol, 94%) of the peptide, 5S-N-tert-butyloxycarbonylamino-2S-isopropyl-7-methyl-4S-tert-butyldimethylsilyloxy-octanoyl-L-isoleucyl-2-pyridylmethylamide (XX$_{20}$I), structure of which was supported by $^1$H-NMR.

C68.

Preparation XX$_{20}$II$_1$

Nα-tert-Butyloxycarbonyl-Nα-methyl-N$^{im}$-tosyl-L-histidine (XX$_{20}$II$_1$)

A 0.75 g portion of 50% sodium hydride in oil (15.6 mmol) is washed with three 7 ml portions of n-pentane under argon. The residue is suspended in 5 ml of dry tetrahydrofuran (distilled from sodium). To this stirred mixture is added 1.59 g (3.88 mmol) of Nα-tert-butyloxycarbonyl-N$^{im}$-tosyl-L-histidine XX$_{20}$II$_2$ in 5 ml of tetrahydrofuran, followed by 2.0 ml (32 mmol) of methyl iodide. After stirring at room temperature for 16 h, the reaction mixture is slowly added to a stirred solution of 20 ml of cold 1M aqueous NaHSO$_4$. Tetrahydrofuran is removed on a rotary evaporator. The aqueous phase is extracted with 100 ml and two 50 ml portions of ethyl acetate. The combined organic phase is washed with two 50 ml portions of 1M aqueous NaHSO$_3$, and then dried (MgSO$_4$). Concentration of the solution given 1.18 g (2.79 mmol, 72%) of Nα-tert-butyloxycarbonyl-Nα-methyl-N$^{im}$-tosyl-L-histidine (XX$_{20}$II$_1$), structure of which was supported by $^1$H-NMR and MS (calcd. for C$_{19}$H$_{25}$N$_3$O$_6$SK 462.1101; found 462.1114).

C69.

Preparation XX$_{20}$II

N-tert-Butyloxycarbonyl-Nα-methyl-N$^{im}$-tosyl-L-histidyl-5S-amino-2S-isopropyl-7-methyl-4S-tert-butyl-dimethylsilyloxy-octanoyl-L-isoleucyl-2-pyridylmethylamide (XX$_{20}$II)

To a stirred solution of 82.7 mg (0.15 mmol) of the free amine (from treatment of the peptide having the formula XX$_{20}$I as prepared above with 1:1=trifluoroacetic acid: dichloromethane and then neutralization with aqueous NaHCO$_3$), 77.7 mg (0.18 mmol) of the amino acid XX$_{20}$II$_1$, above, and 25 μl (0.18 mmol) of triethylamine in 2 ml of dichloromethane is added 30 μl (0.20 mmol) of diethylphosphoryl cyanide. After stirring at room temperature for 14 h, the reaction mixture is partitioned between dichloromethane and saturated aqueous NaHCO$_3$. The aqueous phase is further extracted with two portions of dichloromethane. The combined organic phase is dried (MgSO$_4$), filtered, and then concentrated. The resulting residue is chromatographed on silica gel with 20% hexane in ethyl acetate to give 120.8 mg (0.127 mmol, 84%) of the peptide, N-tert-butyloxycarbonyl-Nα-methyl-N$^{im}$-tosyl-L-histidyl-5S-amino-2S-isopropyl-7-methyl-4 S-tert-butyl-dimethylsilyloxy-octanoyl-L-isoleucyl-2-pyridylmethylamide XX$_{20}$II, structure of which was supported by $^1$H-NMR.

C70.

Preparation XX$_{20}$IV

N-tert-Butyloxycarbonyl-L-phenylalanyl-Nα-methyl-N$^{im}$-tosyl-L-histidyl-5S-amino-4S-hydroxy-2S-isopropyl-7-methyl-octanoyl-L-isoleucyl-2-pyridylmethylamide XX$_{20}$IV To a stirred solution of 92 mg (0.124 mmol) of the free amine (from treatment of the peptide having the formula XX$_{20}$II as prepared above with 1:1=trifluoroacetic acid: dichloromethane and then neutralization with aqueous NaHCO$_3$ to obtain a compound of formula XX$_{20}$III), 35.2 mg (0.133 mmol) of N-tert-butyloxycarbonyl-L-phenylalanine, and 21 μl (0.15 mmol) of triethylamine in 2 ml of dichloromethane is added 25 μl (0.16 mmol) of diethylphosphoryl cyanide. After stirring at room temperature for 14 h, the reaction mixture is partitioned between dichloromethane and saturated aqueous NaHCO$_3$. The aqueous phase was further extracted with two portions of dichloromethane. The combined organic phase is dried (MgSO$_4$), filtered, and then concentrated. The resulting residue was chromatographed on silica gel with 2% methanol in ethyl acetate to give 78.9 mg (0.08 mmol, 64%) of the peptide, N-tert-butyloxycarbonyl-L-phenylalanyl-N$^\alpha$-methyl-N$^{im}$-tosyl-L-histidyl-5S-amino-4 S-hydroxy-2S-isopropyl-7-methyl-octanoyl-L-isoleucyl-2-pyridylmethylamide XX$_{20}$IV, structure of which was supported by $^1$H-NMR and purity was analyzed by reverse-phase HPLC. Mass spectra [M+H]$_+$=833; HPLC retention time 13:1 minutes. The HPLC conditions are those set forth in (b) of Table B.

C71.

Preparaton XX$_{20}$V

N-tert-Butyloxycarbonyl-L-phenylalanyl-N$^\alpha$-methyl-L-histidyl-5S-amino-4S-hydroxy-2S-isopropyl-7-methyl-octanoyl-L-isoleucyl-2-pyridylmethylamide (XX$_{20}$V)

To a stirred solution of 78.9 mg (0.08 mmol) of the peptide having the formula XX$_{20}$IV as prepared above in 1 ml of methanol is added 108 mg (0.8 mmol) of 1-hydroxy-benzotriazole. After stirring at room temperature for 18 h, the reaction mixture is concentrated. The resulting residue is chromatographed on silica gel with 5% methanol (saturated with ammonia) in ethyl acetate to give 62.6 mg (0.075 mmol, 94%) of the peptide, N-tert-butyloxycarbonyl-L-phenylalanyl-N$^\alpha$-methyl-L-histidyl-5S-amino-4S-hydroxy-2S-isopropyl-7-methyl-octanoyl-L-isoleucyl-2-pyridylmethylamide (XX$_{20}$V), structure of which was supported by $^1$H-NMR and purity was analyzed by reverse-phase HPLC.

C72.

Preparation XX$_{20}$VI$_3$

N-tert-Butyloxycarbonyl-L-prolyl-L-phenylalanylbenzyl ester (XX$_{20}$VI$_3$)

To a stirred solution of 2.22 mmol of L-phenylalaninebenzyl ester (XX$_{20}$VI$_4$) (from neutralization of 950 mg of L-phenylalanine benzyl ester, p-toluenesulfonic acid) in 20 ml of dichloromethane is added 480 mg (2.23 mmol) of N-tert-butyloxycarbonyl-L-proline and 300 mg (2.22 mmol) of 1-hydroxy-benzotriazole, followed by 500 mg (2.42 mmol) of dicyclohexylcarbodiimide. After stirring at room temperature for 20 h, the reaction mixture is filtered. The filtrate is diluted with 40 ml of dichloromethane and then washed with 20 ml of saturated aqueous NaHCO$_3$. The aqueous phase is extracted with two 30 ml portions of dichloromethane. The combined organic phase is dried (MgSO$_4$), filtered, and then concentrated. The residue is chromatographed on silica gel with 2% methanol in dichloromethane to give 975 mg (2.15 mmol, 97%) of the dipeptide, N-tert-butyloxycarbonyl-L-prolyl-L-phenylalanylbenzyl ester (XX$_{20}$VI$_3$), structure of which was supported by $^1$H-NMR.

C73.

Preparation XX$_{20}$VI$_2$

N-tert-Butyloxycarbonyl-L-prolyl-L-phenylalanine (XX$_{20}$VI$_2$)

To a stirred solution of 543 mg (1.20 mmol) of the benzyl ester of formula XX$_{20}$VI$_3$ as prepared above in 5 ml of methanol is added 50 mg of 5% palladium on charcoal. The resulting suspension is allowed to stir under hydrogen at room temperature for 2 h. The reaction mixture is filtered through celite and the filtrate concentrated to give the dipeptide, N-tert-butyloxycarbonyl-L-prolyl-L-phenylalanine (XX$_{20}$VI$_2$), structure of which was supported by $^1$H-NMR.

C74.

Preparation XX$_{20}$VI$_1$

N-tert-Butyloxycarbonyl-L-prolyl-L-phenylalanyl-N$^\alpha$-methyl-N$^{im}$-tosyl-L-histidyl-5S-amino-4S-hydroxy-2S-isopropyl-7-methyl-octanoyl-L-isoleucyl-2-pyridylmethylamide (XX$_{20}$VI$_1$)

To a stirred solution of 67 mg (0.09 mmol) of the free amine (from treatment of the peptide of formula XX$_{20}$II as prepared above with 1:1=trifluoroacetic acid: dichloromethane and then neutralization with aqueous NaHCO$_3$), 36 mg (0.1 mmol) of the dipeptide of formula XX$_{20}$VI$_2$ as prepared above and 14 μl (0.1 mmol) of triethylamine in 2 ml of dichloromethane is added 18 μl (0.12 mmol) of diethylphosphoryl cyanide. After stirring at room temperature for 15 h, the reaction mixture is partitioned between dichloromethane and saturated aqueous NaHCO$_3$. The aqueous phase is further extracted with two portions of dichloromethane. The combined organic phase is dried (MgSO$_4$), filtered, and then concentrated. The resulting residue is chromatographed on silica gel with 2.5% methanol in ethyl acetate to give 67.3 mg (0.06 mmol, 69%) of the peptide, N-tert-butyloxycarbonyl-L-prolyl-L-phenylalanyl-N$^\alpha$-methyl-N$^{im}$-tosyl-L-histidyl-5S-amino-4S-hydroxy-2S-isopropyl-7-methyl-octanoyl-L-isoleucyl-2-pyridylmethylamide (XX$_{20}$VI$_1$), structure of which was supported by $^1$H-NMR and purity was analyzed by reverse-phase HPLC.

C75.

Preparation XX$_{20}$VI

N-tert-Butyloxycarbonyl-L-prolyl-L-phenylalanyl-N$^\alpha$-methyl-L-histidyl-5S-amino-4S-hydroxy-2S-isopropyl-7-methyl-octanoyl-L-isoleucyl-2-pyridylmethylamide (XX$_{20}$VI)

To a stirred solution of 67 mg (0.062 mmol) of the peptide of formula XX$_{20}$VI$_1$, as prepared above in 1 ml of methanol is added 25 mg (0.185 mmol) of 1-hydroxy-benzotriazole. After stirring at room temperature for 20 h, the reaction mixture is concentrated. The resulting residue is chromatographed on silica gel with 5% methanol (saturated with ammonia) in ethyl acetate to give 51.5 mg (0.055 mmol, 90%) of the peptide, N-tert-butyloxycarbonyl-L-prolyl-L-phenylalanyl-N$^{60}$-methyl-L-histidyl-5S-amino-4S-hydroxy-2S-isopropyl-7-methyl-octanoyl-L-isoleucyl-2-pyridylmethylamide (XX$_{20}$VI), structure of which was supported by $^1$H-NMR and purity was analyzed by reverse-phase HPLC. Mass spectra [M+H]$^+$=930.5789; HPLC retention time 16.5 minutes. The HPLC conditions are as set forth under (a) in Table B.

C76.

Preparation XX$_{30}$I$_7$ (2R,5S)-2-tert-Butyl-1-aza-3-oxabicyclo[3.3.0]octan-4-one (XX$_{30}$I$_7$)

A mixture of 651 mg (5.65 mmol) of L-proline, 3.0 ml (28 mmol) of 2,2-dimethyl-propanal, and 10 μl of trifluoroacetic acid in 20 ml of pentane is refluxed with a Dean-Stark trap for three days. The reaction mixture is concentrated and the remaining residue is evaporatively distilled at 0.1 mm Hg, 70° C. to give 955 mg (5.2 mmol, 92%) of compound, (2R,5S)-2-tert-butyl-1-aza-3-oxabicyclo[3.3.0]octan-4-one (XX$_{30}$I$_7$), structure of which was supported by $^1$H-NMR.

C77.

Preparation XX$_{30}$I$_6$ (2R,5S)-2-tert-Butyl-5-methyl-1-aza-3-oxabicyclo[3.3.0]octan-4-one (XX$_{30}$I$_6$)

To a stirred solution of 0.88 ml (6.2 mmol) of diisopropylamine in 25 ml of tetrahydrofuran at −78° C. under argon is added 3.8 ml (5.7 mmol) of a 1.5 M solution of n-butyllithium in hexane. The resulting solution is allowed to stir at 0° C. for 10 min and then recooled to −78° C. To this is added a solution of 950 mg (5.2 mmol) of compound of formula XX$_{30}$I$_6$ as prepared above in 5 ml of tetrahydrofuran. After 30 min, 0.39 ml (6.3 mmol) of methyl iodide is then added. After 2 h, the reaction mixture is allowed to warm to room temperature and then partitioned between dichloromethane and saturated aqueous NaHCO$_3$. The organic phase is dried (MgSO$_4$), filtered, and then concentrated. The resulting residue is evaporatively distilled at 0.06 mm Hg, 60° C. to give 764 mg (3.87 mmol, 75%) of compound, (2R,5S)-2-tert-butyl-5-methyl-1-aza-3-oxabicyclo[3.3.0]octan-4-one (XX$_{30}$I$_6$), structure of which was supported by $^1$H-NMR.

C78.

Preparation XX$_{30}$I$_5$

N-tert-Butyloxycarbonyl-α-methyl-L-proline (XX$_{30}$I$_5$)

A solution of 764 mg (3.87 mmol) of compound of the formula XX$_{30}$I$_6$ as prepared above in 10 ml of 15% aqueous HBr is stirred at room emperature for 22 h. The reaction mixture is concentrated and the resulting residue is evaporated with three 25 ml portions of absolute ethanol. To a stirred solution of this residue in 3 ml of dimethylformamide and 1 ml of water is added 306 mg (7.65 mmol) of NaOH in 1 ml of water, followed by 1.173 g (4.76 mmol) of 2-tert-butyloxycarbonyloxyimine-2-phenylacetonitrile. The resulting mixture is heated at 50° C. for 24 h and then cooled. It is then partitioned between ether and water. The aqueous phase is acidified with aqueous HCl and then extracted with several portions of dichloromethane. The combined organic phase is dried (MgSO$_4$), filtered, and then concentrated to give 775 mg (3.38 mmol, 87%) of a white solid, N-tert-butyloxycarbonyl-α-methyl-L-proline (XX$_{30}$I$_5$), structure of which was supported by $^1$H-NMR.

C79.

Preparation Xx$_{30}$I$_4$

N-tert-Butyloxycarbonyl-α-methyl-L-prolyl-L-phenylalanyl-methyl ester (XX$_{30}$I$_4$)

To a stirred mixture of 118 mg (0.513 mmol) of the acid of formula XX$_{30}$I$_5$ as prepared above, 123 mg (0.568 mmol) of phenylalanine methyl ester hydrochloride, 79 μl (0.57 mmol) of triethylamine, and 83.8 mg (0.62 mmol) of 1-hydroxybenzotriazole in 5 ml of dichloromethane is added 117 mg (0.567 mmol) of dicyclohexylcarbodiimide. After stirring at room temperature for 20 h, the reaction mixture is filtered and the filtrate diluted with ether. The organic phase is washed with saturated aqueous NaCl. It is then dried (MgSO$_4$), filtered, and concentrated. The resulting residue is chromatographed on silica gel with 2% methanol in dichloromethane to give 211 mg of the dipeptide, N-tert-Butyloxycarbonyl-α-methyl-L-prolyl-L-phenylalanyl-methyl ester (XX$_{30}$I$_4$) structure of which was supported by $^1$H-NMR.

C80.

Preparation XX$_{30}$I$_3$

N-tert-Butyloxycarbonyl-α-methyl-L-prolyl-L-phenylalanine (XX$_{30}$I$_3$)

To a stirred solution of 200 mg (0.51 mmol) of the dipeptide of formula XX$_{30}$I$_4$ as prepared above, in 3 ml of tetrahydrofuran is added 3 ml of 1M aqueous NaOH. The resulting mixture is stirred vigorously for 2½ h, and then partitioned between ether and water. The aqueous phase is acidified with aqueous HCl and then extracted with several portions of dichloromethane. The combined organic phase is dried (MgSO$_4$), filtered, and then concentrated to give 197 mg of the acid structure of N-tert-Butyloxycarbonyl-α-methyl-L-prolyl-L-phenylalanine (XX$_{30}$I$_3$) which was supported by $^1$H-NMR.

C81.

Preparation XX$_{30}$I$_2$

N-tert-Butyloxycarbonyl-N$^{in}$-tosyl-L-histidyl-5S-amino-2S-isopropyl-7-methyl-4S-tert-butyldimethylsilyloxy-octanoyl-L-isoleucyl-2-pyridylmethylamide (XX$_{30}$I$_2$)

To a stirred solution of 96.3 mg (0.175 mmol) of the free amine (from treatment of the peptide of formula XX$_{20}$I as prepared above in Preparation XX$_{20}$I with 1:1=trifluoroacetic acid: dichloromethane and then neutralization with aqueous NaHCO$_3$), 147 mg (0.36 mmol) of the amino acid XX$_{20}$II$_2$, and 73 μl (0.52 mmol) of triethylamine in 2 ml of dichloromethane is added 53 μl (0.35 mmol) of diethylphosphoryl cyanide. After stirring at room temperature for 16 h, the reaction mixture is partitioned between dichloromethane and saturated aqueous NaHCO$_3$. The aqueous phase is further extracted with two portions of dichloromethane. The combined organic phase is dried (MgSO$_4$), filtered, and then concentrated. The resulting residue is chromatographed on silica gel with 85% ethyl acetate in hexane to give 139.2 mg (0.148 mmol, 84%) of the peptide, N-tert-Butyloxycarbonyl-N$^{in}$-tosyl-L-histidyl-5S-amino-2S-isopropyl-7-methyl-4S-tert-butyldimethylsilyloxy-octanoyl-L-isoleucyl-2-pyridylmethylamide (XX$_{30}$I$_2$), structure of which was supported by $^1$H-NMR.

C82.

Preparation XX$_{30}$I$_1$

N-tert-Butyloxycarbonyl-α-methyl-L-prolyl-L-phenylalanyl-N$^{in}$-tosyl-L-histidyl-5S-amino-4S-hydroxy-2S-isopropyl-7-methyl-octanoyl-L-isoleucyl-2-pyridylmethylamide (XX$_{30}$I$_1$)

To a stirred solution of 110 mg (0.148 mmol) of the free amine (from treatment of the peptide of formula XX$_{30}$I$_2$ as prepared above with 1:1=trifluoroacetic acid: dichloromethane and then neutralization with aqueous NaHCO$_3$), 60 mg (0.16 mmol) of the dipeptide XX$_{30}$I$_3$, and 25 μl (0.18 mmol) of triethylamine in 2 ml of dichloromethane is added 29 μl (0.19 mmol) of diethylphosphoryl cyanide. After stirring at room temperature for 15 h, the reaction mixture is partitioned between dichloromethane and saturated aqueous NaHCO$_3$. The aqueous phase is further extracted with two portions of dichloromethane. The combined organic phase is dried (MgSO$_4$), filtered, and then concentrated. The resulting residue was chromatographed on silica gel with 5% methanol in ethyl acetate to give 131.2 mg (0.12 mmol, 82%) of the peptide, N-tert-Butyloxycarbonyl-α-methyl-L-prolyl-L-phenylalanyl-N$^{in}$-tosyl-L-histidyl-5 S-amino-4S-hydroxy-2S-isopropyl-7-methyl-octanoyl-L-isoleucyl-2-pyridylmethylamide (XX$_{30}$I$_1$), structure of which was supported by $^1$H-NMR.

C83.

Preparation XX$_{30}$I

N-tert-Butyloxycarbonyl-α-methyl-L-prolyl-L-phenylalanyl-L-histidyl-5 S-amino-4S-hydroxy-2S-isopropyl-7-methyl-octanoyl-L-isoleucyl-2-pyridylmethylamide (XX$_{30}$I) and its dicitrate salt To a stirred solution of 90.1 mg (0.083 mmol) of the peptide of formula XX$_{30}$I$_1$ as prepared above in 1.5 ml of methanol is added 34 mg (0.25 mmol) of 1-hydroxybenzotriazole. After stirring at room temperature for 14 h, the reaction mixture is concentrated. The resulting residue is chromatographed on silica gel with 7% methanol (saturated with ammonia) in ethyl acetate to give 70.2 mg (0.075 mmol, 91%) of the peptide, N-tert-Butyloxycarbonyl-α-methyl-L-prolyl-L-phenylalanyl-L-histidyl-5 S-amino-4S-hydroxy-2S-isopropyl-7-methyl-octanoyl-L-isoleucyl-2-pyridylmethylamide (XX$_{30}$I), structure of which was supported by $^1$H-NMR and purity was analysed by reverse-phase HPLC (retention time 18.1 minutes under conditions as set forth under (a) in Table B). FAB-MS:930.5841.

The dicitrate salt of the titled compound was prepared and shows the same behavior as the free base for FAB-MS and HPLC retention time.

C84.

Preparation of Boc-PEP-His-LVA-Ile-AMP

Part A

Boc-Ile-AMP (0.32 g, 1.0 mmole) is stirred in 10 ml of TFA-CH$_2$Cl$_2$ (1:1, v/v) for 30 minutes. TFA and CH$_2$Cl$_2$ are removed in vacuo and the residue is held under vacuum overnight. The residue is extracted with EtOAc and 5 ml of saturated aqueous NaHCO$_3$. The organic layers are filtered through Na$_2$SO$_4$ and concentrated. The crude product is chromatographed on silica gel using 4% MeOH-CH$_2$Cl$_2$ (NH$_4$OH sat'd) to give 0.194 g (88%) of Ile-AMP.

To 0.194 g (0.88 mmoles) of Ile-AMP, 0.134 g (0.88 mmoles) of 1-HOBT, 0.391 g (0.88 mmoles) of Boc-LeuΨ[CH(OSit-BuMe$_2$)]Val-OH, and 10 ml of CH$_2$Cl$_2$ is added 0.181 g (0.88 mmoles) of DCC. After stirring 5 hours, DCU is filtered off and the filtrate is extracted with CH$_2$Cl$_2$ and saturated aqueous NaHCO$_3$ (twice). The organic layers are filtered through Na$_2$SO$_4$, concentrated, and chromatographed on silica gel using 4% MeOH-CH$_2$Cl$_2$ to give 0.428 g (75%) of Boc-LeuΨ[CH(OSi-t-BuMe$_2$)CH$_2$]Val-Ile-AMP.

TLC (4% MeOH-CH$_2$Cl$_2$) Rf=0.14; NMR (CDCl$_3$): NMR peaks are observed at δ 0.11; 0.83–0.95, 0.90, 1.43, 3.55, 4.5, 4.56, 6.10, and 7.1–8.1.

Part B

A solution of 0.428g (0.660 mmoles) of the compound of Part A in 20 ml of TFA-CH$_2$Cl$_2$ (1:1, v/v) is stirred for 30 minutes. TFA and CH$_2$Cl$_2$ are removed in vacuo and the residue is extracted with methylene chloride and saturated aqueous sodium bicarbonate (2X). The organic layers are filtered through Na$_2$SO$_4$ and concentrated in vacuo to give 0.354 g (98%) of LeuΨ[CH(OSitBuMe$_2$)CH$_2$]Val-Ile-AMP, containing a trace of LeuΨ[CH(OH)CH$_2$]Val-Ile-AMP.

TLC (8% MeOH-CH$_2$Cl$_2$(NH$_4$OH)): Rf=0.53 (Rf=0.17 for impurity).

Part C

To 0.150 g (0.273 mmoles) of the compound of Part B and 0.161 g (0.393 mmoles) of Boc-His(Tos)-OH in 4 ml of CH$_2$Cl$_2$ was added 0.056 g (0.271 mmoles) of DDC. After 3 ½ hours N,N'-dicyclohexylurea (DCU) is filtered off. The filtrate is concentrated and the crude product is chromatographed on silica gel using 4% MeOH-CH$_2$Cl$_2$ (0.1% NH$_4$OH) to give 0.1942 g of Boc-His(Tos)-LeuΨ[CH(OSit-BuMe$_2$)CH$_2$]Val-Ile-AMP.

TLC [4% MeOH:96% CH$_2$Cl$_2$(NH$_4$OH)]: Rf=0.31.

Part D

A mixture of 0.1942 g of the compound of Part C and 6 ml of TFA-CH$_2$Cl$_2$ (1:1) is stirred at room temperature for 1 ½ hours. TFA and CH$_2$Cl$_2$ are then removed in vacuo and the residue is extracted with CH$_2$Cl$_2$ and saturated aqueous NaHCO$_3$ (2×). The organic layers are filtered through Na$_2$SO$_4$ and the solvent is removed in vacuo to give 0.1229 g of H-His(Tos)LVA-Ile-AMP.

TLC [4% MeOH:96% CH$_2$Cl$_2$(NH$_4$OH)]: Rf=0.12.

Part E

To 0.0148 g (0.0259 mmoles) of the compound of Part D and 0.0181 g (0.0518 mmoles) of Boc-(2S,5S)-ProΨ[CH$_2$O]Phe-OH in 2 ml of CH$_2$Cl$_2$ is added 0.0107 g (0.0518 moles) of DCC in 1 ml of CH$_2$Cl$_2$. After stirring for 2 hours, excess DCC is quenched with approximately ½ drop of HOAc and DCU is filtered off. The filtrate is extracted with CH$_2$Cl$_2$ and saturated aqueous NaHCO$_3$×). The combined organic layers are filtered through Na$_2$SO$_4$, concentrated, and the crude material is chromatographed on silica gel with 4% MeOH/CH$_2$Cl$_2$ to give 0.0168 g of Boc-PEP-His(Tos)-LVA-Ile-AMP.

0.0168 g of the product of the previous paragraph, 0.07g of 1-HOBT, 3 ml of CH$_2$Cl$_2$, and 1 ml of THF are stirred overnight at room temperature. The solvents are then removed in vacuo and the residue is extracted with CH$_2$Cl$_2$ and saturated aqueous NaHCO$_3$ (2×). The organic layers are filtered through Na$_2$SO$_4$, concentrated, and chromatographed on silica gel using 6% MeOH/CH$_2$Cl$_2$ (0.1% NH$_4$OH) to give 0.0087 g of Boc-PEP-His-(Tos)LVA-Ile-AMP.

TLC (8% MeOH:92% CH$_2$Cl$_2$, NH$_4$OH): Rf=0.38.

HPLC: Brownlee C$_{18}$ 10μ column, phosphate buffer, pH 3.0, 80% B (CH$_3$CN)-20% A (H$_2$O), k'=4.8 (λ 225, flow rate 1.5 ml/min); purity 100%.

FAB mass spec.: [M+H]$^+$ at m/z 903 (calc'd. 903).

C85.

Additional Compounds

Following the procedures set forth above, and those procedures known in the art, the renin-inhibiting compounds of TABLE A are prepared. Physicochemical data for these compounds is set forth in TABLE B. Data is generated in some instances from the trifluoroacetate salt of the structure depicted in TABLE A.

EXAMPLE B1

Renin Inhibitory Activity

Activity for the novel renin-inhibiting peptides of the present invention is determined in the following manner.

Lyophilized human plasma with 0.1% EDTA is obtained from New England Nuclear, North Billerica, Mass. 01862 as "Plasma Renin Activity Control". This lyophilized plasma is reconstituted, on the day of the assay, with cold sterile distilled water according to directions on the vial. The plasma renin activity (PRA) of the reconstituted plasma is assayed with "GAMMACOAT [$^{125}$I] Plasma Renin Activity Radioimmunoassay Kit" supplied by Clinical Assays, a Division of Travenol Laboratories, Inc., Cambridge, Mass. 02139. The procedure used with these kits is carried out essentially as described in the literature which accompanies them. The initial (enzymatic generation of Angiotensin 1) step is modified slightly to accommodate the testing of renin inhibitors and to minimize the amount of plasma required to perform the assay. Thus, for every milliliter of reconstituted plasma used in the assay, there is added and vortexed 10 $\mu$l of PMSF (0.3 M phenylmethylsulfonly fluoride in ethanol) and 100 $\mu$l of maleate generation buffer, both provided in the kit. 250 $\mu$l of this mixture is then transferred to each tube used in the generation step along with 10 $\mu$l of the potential renin inhibitor suspended or dissolved in 1% Tween 80 in water. This mixture is incubated for 90 minutes at 37° C. in a shaking water bath. Also, in addition to the tubes that incubate at 37° C., 4° C. blanks are run on all compounds assayed as a check for compound-antibody cross reactivity. These 4° C. blanks are identical in volume and composition to those that incubate at 37° C. At the end of the 90 minute incubation, the tubes are placed immediately in an ice water bath to terminate the reaction.

In the RIP, 100 $\mu$l of the 4° C. blank is added to a GAMMACOAT tube. In these GAMMACOAT tubes, the antibody is immobilized onto the lower inner wall thereby eliminating the need to pipette antibody. Finally, 1 ml of tracer buffer reagent is added to each tube and vortexed. All tubes are allowed to equilibrate for three hours at room temperature. At the end of the equilibration period, the contents of the tubes are decanted. The tubes are then counted in a gamma counter. The results of the RIP are evaluated with the Rodbard Radioimmunoassay Program available on Upjohn computer terminals and the plasma renin activity (PRA) is expressed as mg/ml/hr. Plasma renin activity values obtained for 4° C. blanks are subtracted from the appropriate 37° C. tubes. PRA values from the plasma tubes incubated with compound are compared to then 1% Tween 80 control tubes to yield a percent inhibition. The inhibition results are express as $I_{50}$ values which are obtained by plotting two inhibitor concentrations and estimating the concentration producing 50% inhibition. In addition to $I_{50}$ values, relative potencies are also calculated. A relative potency is determined by comparing the $I_{50}$ of RIP to the $I_{50}$ of the compound. However, it must be emphasized that relative potencies are calculated from the $I_{50}$ obtained for RIP on the day the compound is assayed and not from the average $I_{50}$ for RIP.

It has been determined that the GAMMACOAT-PRA assay is a suitable replacement for the RENAK assay (supplied by Hoffman-LaRoche and previously known as a diagnostic test for high renin states) to determine the activity of potential renin inhibitors.

EXAMPLE B2

Enzyme Stability Testing

Certain compounds of the present invention are stable to selected natural enzymes in the test described below. It is believed the stability to the enzymes provides more effective delivery of the renin-inhibiting activity. Certain enzymes were chosen to determine the noted stability. These were pepsin, chymotrypsin, elastase, and carboxypeptidase.

Pepsin is a broad term representing a mixture of acid proteases which have activity at very low pH and are secreted by the gastric mucosa into the gut. It was chosen because it would probably be the first type of proteolytic enzyme that any orally active peptide would have to be stable against. Usually pepsin cleavage sites are C-terminal to Phe, Tyr, Leu, and Trp amino acids.

Chymotrypsin and elastase are contained in the pancreatic juices secreted into the small intestine. These two enzymes possess the type of proteolytic cleavage that an orally active peptide will have to resist while passing through the intestinal tract prior to absorption. Chymotrypsin cleaves primarily C-terminal to Phe, Tyr, and Trp amino acid residues. Elastase is more specific to uncharged non-aromatic residues such as Ala, Val, Gly, and Ser.

Carboxypeptidases are also contained in the pancreatic juices released into the gut. This class of peptidase begins cleaving at the C-terminus and removes one residue at a time. Carboxypeptidase A will cleave virtually any residue but is less specific for lysine and arginine. Carboxypeptidase B (found circulating in the blood as well as being found in the gut) specifically cleaves at lysine and arginine residues. Rather than use a mixture of these two enzymes, a yeast enzyme, carboxypeptidase Y, was chosen to represent this type of proteolytic digestion. Carboxypeptidase Y has no amino acid specificity; it will sequentially cleave amino acid residues from the C-terminus of a peptide.

Trypsin is not chosen for routine analysis of stability because it is most specific for cleavage on the C-terminal side of Lys and Arg residues. The analogs of RIP that are preferred for oral administration in this invention do not have amino acids to the C-terminal of any Lys or Arg residues and therefore trypsin is an inappropriate protease for use in this study.

It should be emphasized that the specificities listed above are the primary cleavage sites for these enzymes. Proteolytic enzymes can cleave at sites other than their designated primary site.

The enzymes tested represented only a few of the possible digestive pathways that a peptide might face on its passage through the gut. Any oraly active peptide will have to be stable to the enzymes used in this study, but other enzymes which have not yet been tested may still degrade the peptide. However, if stability is shown against those peptidases used here, then it is believed the peptide will be stable in vivo.

Methods used to show the stability are applied to compounds of formula XX to determine the compounds and dosages therefor to be used for the preferred oral administration route noted above. The methods are as follows:

The conditions used for the enzymatic degradation of peptides including the enzyme concentrations and buffer systems, are listed in Table 1.

Enzymatic reactions are carried out at 37° for 0, 30, or 60 minutes. Enzymes are inactivated by immersing the reaction vessel in boiling water for 5 minutes, adding a portion of solvent B (described below) equivalent to the reaction volume, capping the reaction vial and immediately freezing it in a dry ice-ethanol bath. The vials are kept frozen until they were ready to be assayed. Later experiments showed that addition of solvent B is sufficient to inactivate the enzymes and that heating and freezing of the samples are not necessary so these steps were removed from the protocol. Also, 10% DMSO is determined to have no effect on enzymatic activity and is therefore used to help dissolve some of the less soluble peptides. The DMSO usually does not keep the more insoluble peptides in solution but it helps to maintain these peptides in a finer suspension.

HPLC OF FRAGMENTS

Fragmentation of the peptides is analyzed by reverse phase HPLC. Separations are carried out on a 25cm×0.46mm SynChrom RP-P column. A gradient of increasing concentrations of acetonitrile are used to elute the peptide fragments. Solvent A consists of 50mM $NaH_2PO_4$ (6.9 g/l), 1.0% $H_3PO_4$, 1% acetonitrile and 99% water. Solvent B consists of 12.5mM $NaH_2PO_4$ (1.75 g/l), 0.25% $H_3PO_4$, 75% acetonitrile and 25% water. A Kontron Model 200 Controller is programmed to deliver the solvents starting at 10% solvent B and linearly increase to 50% solvent B over 15 minutes. The solvent concentration is held at 50% solvent B for 10-20 minutes before being dropped back to 10% solvent B over a 2 minute period. The column is allowed to reequilibrate for at least 13 minutes before another sample is injected. Samples are injected onto the column using a Kontron model MSI660 Autosampler equipped with a 100 μl sample loop. Column effluent is monitored using a Beckman 165 dual wavelength detector. Absorption is measured at 204 and at 280.

DATA ANALYSIS

The signal of the UV absorption at 204 nm is fed into a Hewlett Packard Model 3390A integrator. The peak weight of the peptide eluting at a time consistent with that of the parent inhibitor is used to determine the extent of breakdown of the parent peptide. The percent change from the parent peak observed at 0 time is calculated for 30 minute and 60 minute incubation times. All peptides tested are compared with the results obtained for the compound RIP which is also run as a control in each experiment.

EXAMPLE B3

Oral Administration-Renin-Infused Rats

The in vivo evaluation technique in renin-infused rats was adapted from a description by Blaine, Schorn, and Boger in Hypertension G (Supp I): I111-I118, 1984. Their technique was modified so that oral administration as well as intravenous administration could be studied in the same preparation. Male Sprague-Dawley rats weighing 200-350 g were anesthetized with dial/urethane (100 mg/kg i.p.). A median ventral neck incision was made, the trachea was cannulated, and both vagus nerves were sectioned. One caroted artery was cannulated with PE 50 tubing and connected to a Statham P23D transducer and Grass polygraph for continuous recording of blood pressure. Both jugular veins were cannulated with PE 50 tubing to facilitate intravenous injections and infusions. In some experiments, an infant feeding tube (Davol #3641) was cut to a length of 7.5 inches and inserted into the rat's stomach via its mouth. The tube was clamped to prevent backflow of gastric contents. Oral administraton of compounds and/or vehicles was only carried out in animals which had not had access to food during the preceeding 24 hours. Following surgery, ganglion blockade was instituted with intravenous mecamylamine at 1.25 mg/kg. When mean arterial blood pressure had stabilized at about 60 mmHg, partially purified hog renin (ICN Pharmaceuticals Inc., Cleveland, Ohio) was infused at an initial primary dose of approximately 0.11 GU/min for 5 minutes followed by a sustaining infusion of approximately 0.028 GU/min. The renin infusion was adequate to restore blood pressure to the level observed before vagotomy and ganglion blockade. Blood pressure had stabilized in the majority of the preparations 20 minutes after the start of the renin infusion. After a 15 minute control period, a compound or its vehicle were infused intravenously or administered orally into the stomach. Blood pressure was monitored for a total of 105 minutes after the administraton of drug or vehicle.

EXAMPLE B4

Oral Administration-Sodium Depleted Monkeys

The in vivo evaluation in sodium-depleted monkeys was similar to that described by Pals et al in Clin. and Exper. Hypertension A7(1):105-121, 1985. Male cynomolgus monkey (weight 4 to 6 kg) were placed in primate restraining chairs. Following acclimation for a few days, each monkey was anesthetized and polyvinyl catheters were implanted under sterile conditions in the abdominal aorta and the thoracic vena cava via an external iliac artery and vein respectively. The catheters were routed subcutaneously from the grain area to the top of the head and exteriorized. At least one week was allowed for recovery from surgery. During this week, the monkeys were fed a quantity of "Standard SKF Monkey Diet deleting sodium" (ICN Nutritional Biochemicals, Cleveland, Ohio) adequate to furnish potassium at 1 meg/kg per day and were also given intravenous 0.9% saline adequate to provide sodium at 1 meg/kg per day. Sodium depletion was accomplished by omitting the daily intravenous administration of saline and substituting the intravenous administration of furosemide (1 mg/kg body weight per day) for six days. Drinking water was allowed ad lib. On the seventh day, the arterial catheter was connected to a Statham pressure transducer and a Grass polygraph for the continuous recording of blood pressure. Heart rate was continuously recorded from a Grass tachograph triggered by the arterial pressure pulse. Saralasin, an angiotensin II antagonist, was administered intravenously at 1 mg/kg about 5 hours prior to administration of intravenous renin inhibitory peptide or 18 hours prior to the oral administration of renin inhibitory peptide to elucidate the magnitude of the renin-dependent blood pressure compound. The renin inhibitory peptide in vehicle or the vehicle alone was administered intravenously via the jugular vein catheter or administered "orally" into the stomach via the nasal route with an infant feeding tube (Davol #3641).

Of the compounds of the present invention tested in these assays Boc-Pro-Phe-NMHis-Leu-Ψ[—

CHOHCH$_2$]-Val-Ile-AMP and its citrate salt (see C75. Preparation XX$_{20}$VI) are preferred.

The dicitrate salt of compound XX$_{20}$VI (See C75. Preparation of XX$_{20}$VI above) is prepared in methanol from 1 part of compound XX$_{20}$VI and 2 parts of citric acid. The solution is concentrated. Water is added to the residue and this mixture is then lyophilized to give the 1:2 adduct of Boc-Pro-Phe-NMHis-LewΨ[CH(OH)CH$_2$]Val-Ile-AMP and citric acid, which adduct shows the same behavior as the free base for FAB-MS and HPLC retention time.

TABLE 1
Conditions for Enzymatic Digestion of Renin Inhibitory Peptides

| Enzyme | Concentration | Buffer System | Amount Added per 0.25 ml of 0.8 mg/ml Peptide |
|---|---|---|---|
| Pepsin (Difco 0151-15) | 0.01 mg/ml | 0.05 M HCl | 0.25 ml |
| Carboxypeptidase Y (Sigma C 3888) | 50 U/ml | 50 mM Tris-HCl pH 7.5 | 5 μl |
| Chymotrypsin (Sigma C-3142) | 25 U/ml (0.51 mg solid/ml) | 50 mM Tris-HCl pH 7.5 | 5 μl |
| Elastase (Sigma E-1250) | 50 U/ml (9.2 μl/0.25 ml buffer) | 50 mM Tris-HCl pH 7.5 | 5 μl |

TABLE A

| Cpd | X | A$_6$ | B$_7$ | C$_8$ | D$_9$ | E$_{10}$/F$_{11}$ | G$_{12}$ | H$_{13}$ | I$_{14}$ | Z |
|---|---|---|---|---|---|---|---|---|---|---|
| 1 | Ac | FTrp | Pro | Phe | NMHis | LVA | Ile | abs | abs | AMP |
| 2 | POA | abs | abs | abs | NMHis | LVA | Ile | abs | abs | AMP |
| 3 | Ac | FTrp | Pro | Phe | NMHis | Statine | Ile | abs | abs | NH$_2$ |
| 4 | Ac | abs | Pro | Phe | NMHis | LVA | Ile | abs | abs | AMP |
| 5 | Ac | Phe | Pro | Phe | NMHis | LVA | Ile | abs | abs | AMP |
| 6 | H— | abs | Pro | Phe | NMHis | LVA | Ile | abs | abs | AMP |
| 7 | PGA | abs | abs | Phe | NMHis | LVA | Ile | abs | abs | AMP |
| 8 | Ac | PLA | abs | abs | NMHis | LVA | Ile | abs | abs | AMP |
| 9 | Ac | His | Pro | Phe | NMHis | LVA | Ile | abs | abs | AMP |
| 10 | Boc | abs | abs | Nal1 | NMHis | LVA | Ile | abs | abs | AMP |
| 11 | Boc | abs | Pro | Nal1 | NMHis | LVA | Ile | abs | abs | AMP |
| 12 | NOA1 | abs | abs | abs | NMHis | LVA | Ile | abs | abs | AMP |
| 13 | NOA2 | abs | abs | abs | NMHis | LVA | Ile | abs | abs | AMP |
| 14 | Ac | abs | abs | abs | NMHis | LVA | Ile | abs | abs | AMP |
| 15 | Boc | abs | abs | Phe | NMHis | LVA | abs | abs | abs | IBA |
| 16 | Boc | abs | abs | Phe | His | LVA | LeR | abs | abs | OME |
| 17 | Boc | abs | abs | Phe | His | LVA | IlR | abs | abs | OME |
| 18 | Boc | abs | abs | Phe | NMHis | LVA | abs | abs | abs | OME |
| 19 | Boc | abs | abs | DNal2 | NMHis | LVA | Ile | abs | abs | AMP |
| 20 | Boc | abs | abs | Phe | NMHis | LVAME | abs | abs | abs | abs |
| 21 | Boc | abs | abs | Phe | His | LVAME | abs | abs | abs | abs |
| 22 | Boc | abs | abs | Nal2 | NMHis | LVA | Ile | abs | abs | AMP |
| 23 | Ac | Phe | Pro | Phe | NMHis | Statine | Ile | abs | abs | NH$_2$ |
| 24 | Ac | FTrp | Pro | Phe | NMHis | Statine | Ile | abs | abs | NH$_2$ |
| 25 | Ac | FTrp | Pro | Phe | NMHis | PRP | abs | abs | abs | NH$_2$ |
| 26 | Boc | abs | Pro | Nal2 | NMHis | LVA | Ile | abs | abs | AMP |
| 27 | Boc | abs | Pro | DPhe | NMHis | LVA | Ile | abs | abs | AMP |
| 28 | Boc | abs | abs | Phe | NMHis | LVA | abs | abs | abs | MBA |
| 29 | Ac | abs | Pro | Phe | NMHis | PRP | abs | abs | abs | NH$_2$ |
| 30 | Boc | FTrp | Pro | Phe | NMPhe | LVA | Ile | abs | abs | AMP |
| 31 | Ac | FTrp | Pro | Phe | Pro | PRP | Ile | abs | abs | NH$_2$ |
| 32 | Ac | FTrp | Pro | Phe | Glu | PRP | Ile | abs | abs | NH$_2$ |
| 33 | Ac | FTrp | Pro | Phe | His | PRP | Gly | abs | abs | NH$_2$ |
| 34 | Ac | FTrp | Pro | Phe | His | Statine | MLE | abs | abs | NH$_2$ |
| 35 | Ac | FTrpD | Pro | Phe | His | Statine | Ile | abs | abs | NH$_2$ |
| 36 | Ac | FTrp | Pro | Phe | His | OAcStat | Ile | abs | abs | NH$_2$ |
| 37 | Ac | FTrp | Pro | Phe | His | Statine | abs | abs | abs | NH$_2$ |
| 38 | Ac | FTrp | Pro | Phe | His | PRP | abs | abs | abs | NH$_2$ |
| 39 | Ac | FTrp | Pro | Phe | His | Statine | Gly | abs | abs | NH$_2$ |
| 40 | Ac | FTrp | Pro | Phe | D—Pro | Statine | Ile | abs | abs | NH$_2$ |
| 41 | Ac | FTrp | Pro | Phe | Pro | Statine | Ile | abs | abs | NH$_2$ |
| 42 | Ac | FTrp | D—Pro | Phe | His | Statine | Ile | abs | abs | NH$_2$ |
| 43 | Ac | FTrp | abs | Phe | His | Statine | Ile | abs | abs | NH$_2$ |
| 44 | Ac | FTrp | Pro | Phe | Hyp | PRP | abs | abs | abs | NH$_2$ |
| 45 | Ac | FTrpD | abs | Phe | His | Statine | Ile | abs | abs | NH$_2$ |
| 46 | Boc | abs | PrR | Phe | His | LVA | Ile | abs | abs | AMP |
| 47 | Boc | abs | | PEP | His | LVA | Ile | abs | abs | AMP |
| 48 | Ac | abs | abs | NLA1 | His | LVA | Ile | abs | abs | AMP |
| 49 | Ac | PLA | abs | abs | His | LVA | Ile | abs | abs | BPA |
| 50 | Boc | abs | abs | Nal1 | His | LVA | abs | abs | abs | IBA |
| 51 | Ac | PLA | abs | abs | His | LVA | Ile | abs | abs | AEP |
| 52 | Boc | abs | abs | Phe | His | LVA | Ile | abs | abs | AMP |
| 53 | Boc | abs | abs | Phe | His | LVA | abs | abs | abs | NHM |
| 54 | Ac | abs | abs | Nla2 | His | LVA | abs | abs | abs | IBA |
| 55 | Ac | abs | abs | Gly | His | LVA | abs | abs | abs | IBA |
| 56 | Mec | aba | abs | Phe | His | LVA | abs | abs | abs | IBA |
| 57 | Ac | Trp | Pro | MPhe | His | Statine | Leu | abs | abs | NH$_2$ |
| 58 | H | Trp | Pro | MPhe | His | Statine | Leu | abs | abs | NH$_2$ |
| 59 | Ac | abs | PhR | Phe | His | Statine | Ile | abs | abs | NH$_2$ |
| 60 | CH$_3$ | NLA2 | abs | abs | His | LVA | abs | abs | abs | IBA |

TABLE A-continued

| Cpd | X | A₆ | B₇ | C₈ | D₉ | E₁₀/F₁₁ | G₁₂ | H₁₃ | I₁₄ | Z |
|---|---|---|---|---|---|---|---|---|---|---|
| 61 | CH₃ | NLA1 | abs | abs | His | LVA | abs | abs | abs | IBA |
| 62 | CH₃ | NLA1 | abs | abs | His | LVA | abs | abs | abs | IBA |
| 63 | Tsp | abs | abs | Phe | His | LVA | abs | abs | abs | IBA |
| 64 | Ac | Nla | abs | abs | His | LVA | Ile | abs | abs | AMP |
| 65 | CH₃ | NLA1 | abs | abs | His | LVA | Ile | abs | abs | AMP |
| 66 | CH₃ | NLA1 | abs | abs | His | LVA | abs | abs | abs | AMP |
| 67 | MSP | abs | abs | Phe | His | LVA | abs | abs | abs | AMP |
| 68 | Tsp | abs | abs | abs | His | LVA | Ile | abs | abs | AMP |
| 69 | NOA¹ | abs | abs | abs | His | LVA | Ile | abs | abs | AMP |
| 70 | NOA² | abs | abs | abs | His | LVA | Ile | abs | abs | AMP |
| 71 | CH₃ | NLA2 | abs | abs | His | LVA | Ile | abs | abs | AMP |
| 72 | Boc | His |  | PEP | His | LVA | Ile | abs | abs | AMP |
| 73 | Boc | Phe |  | PEP | His | LVA | Ile | abs | abs | AMP |
| 74 | Boc | abs | MPr | Phe | His | LRV | Ile | abs | abs | AMP |
| 75 | Boc | abs |  | PEP | His | Statine | Ile | Phe | abs | OCH₃ |
| 76 | Boc | abs |  | PEP | His | Statine | Ile | abs | abs | BPA |
| 77 | Boc | abs |  | PEP | His | Statine | Ile | abs | abs | AMP |
| 78 | Boc | His |  | PEP | His | Statine | Ile | abs | abs | AMP |
| 79 | Boc | His |  | PEP | His | Statine | Ile | Phe | abs | OCH₃ |
| 80 | N—Ac | His |  | PEP | His | Statine | Ile | Phe | abs | OCH₃ |
| 81 | N—Ac | Trp |  | PEP | His | Statine | Ile | Phe | abs | OCH₃ |
| 82 | Boc | Trp |  | PEP | His | Statine | Ile | Phe | abs | OCH₃ |
| 83 | Boc | Trp |  | PEP | His | Statine | Ile | FTrp | abs | OCH₃ |
| 84 | Boc | Trp |  | PEP | His | Statine | Ile | abs | abs | FIEA |
| 85 | Boc | Phe |  | PEP | His | AHPPA | Ile | Phe | abs | OCH₃ |
| 86 | Boc | Pro |  | PEP | His | LVA | Ile | abs | abs | AMP |
| 87 | H | abs | abs | abs | abs | LVA | Ile | Phe | abs | OCH₃ |
| 88 | H | abs | abs | abs | abs | LVA | Ile | abs | abs | AMP |
| 89 | POA | abs | abs | abs | His | 4RLVA | Ile | Phe | abs | OCH₃ |
| 90 | POA | abs | abs | abs | abs | LVA | Ile | abs | abs | AMP |
| 91 | H | abs | abs | PLA | abs | LVA | Ile | abs | abs | AMP |
| 92 | Boc | abs | abs | Phe | 3PB | LVA | abs | abs | abs | IBA |
| 93 | Ac | PLA | abs | abs | His | LVA | abs | abs | abs | IBA |
| 94 | Boc | abs | abs | Phe | 3PA | LVA | abs | abs | abs | IBA |
| 95 | Boc | abs | abs | Phe | 2PR | LVA | abs | abs | abs | IBA |
| 96 | Boc | abs | abs | Phe | 4PR | LVA | abs | abs | abs | IBA |
| 97 | Boc | FTrp | PrR | Phe | His | Sta | Ile | abs | abs | AMP |
| 98 | Boc | FTrp | PrR | Phe | His | Sta | Ile | FTrp | abs | OCH₃ |
| 99 | MEC | abs | abs | Phe | His | Sta | Ile | Phe | abs | OCH₃ |
| 100 | Ac | FTrp | PrR | Phe | His | Sta | Ile | FTrp | abs | OCH₃ |
| 101 | Ac | abs | PrR | Phe | His | OAcStat | Ile | abs | abs | AMP |
| 102 | Ac | abs | abs | PLA | His | Sta | Ile | Phe | abs | OCH₃ |
| 103 | Boc | abs | abs | NMPhe | His | Sta | Ile | abs | abs | AMP |
| 104 | Ac | FTrp | PrR | Phe | His | Sta | Ile | abs | abs | AMP |
| 105 | TBA | abs | abs | PLA | His | Sta | Ile | abs | abs | AMP |
| 106 | Ac | abs | abs | PLA | His | Sta | Ile | abs | abs | AMP |
| 107 | H | abs | abs | PLA | His | Sta | Ile | abs | abs | AMP |
| 108 | MSA | abs | abs | Phe | His | LVA | abs | abs | abs | IBA |
| 109 | H | abs | abs | NLA1 | His | LVA | Ile | abs | abs | AMP |
| 110 | Ac | abs | abs | PLAR | His | LVA | Ile | abs | abs | AMP |
| 111 | DEC | abs | abs | NLA1 | His | LVA | Ile | abs | abs | AMP |
| 112 | Ac | abs | abs | NLA1R | His | LVA | Ile | abs | abs | AMP |
| 113 | Boc | abs | abs | PEA | His | LVA | Ile | abs | abs | AMP |
| 114 | Ac | abs | abs | NLA1 | His | LVA | abs | abs | abs | MBA |
| 115 | Ac | abs | abs | Nla2 | His | LVA | Ile | abs | abs | AMP |
| 116 | Boc | abs | abs | HPhe | His | LVA | Ile | abs | abs | AMP |
| 117 | Ac | abs | abs | BLA | His | LVA | Ile | abs | abs | AMP |
| 118 | Ac | FTrp | Pro | Phe | His | Sta | Ile | abs | abs | NH₂ |
| 119 | Boc | abs | abs | Phe | Gly | LVA | abs | abs | abs | MBA |
| 120 | Poa | abs | abs | abs | His | LVA | Ile | abs | abs | AMP |
| 121 | Ac | FTrp | Pro | Phe | NMHis | LVA | Ile | abs | abs | NH₂ |
| 122 | Boc | abs | PrR | Phe | His | Statine | Ile | Phe | abs | OME |
| 123 | Boc | abs | PrR | Phe | His | Statine | Ile | Phe | abs | OME |
| 124 | Boc | abs | PrR | Phe | His | Statine | Ile | Phe | abs | OME |
| 125 | Ac | abs | PrR | Phe | His | Statine | Ile | abs | abs | AMP |
| 126 | Boc | abs | PrR | Phe | His | AHPPA | Ile | abs | abs | AMP |
| 127 | POA | abs | PrR | Phe | His | Statine | Ile | abs | abs | AMP |
| 128 | TBA | abs | PrR | Phe | His | Statine | Ile | abs | abs | AMP |
| 129 | Boc | abs | PrR | Phe | His | Statine | Ile | abs | abs | AMP |
| 130 | Boc | abs | Pro | Phe | NMHis | LVA | abs | abs | abs | CMA |
| 131 | Boc | abs | abs | Phe | NMHis | LVA | abs | abs | abs | CMA |
| 132 | NOA¹ | abs | abs | abs | His | LVA | abs | abs | abs | CMA |
| [Compounds 133–167 are described in the text.] | | | | | | | | | | |
| 168 | Ac | abs | abs | NLA1 | His | LVA | abs | abs | abs | CMA |
| 169 | Ac | Nal2 | Pro | Phe | His | Statine | abs | abs | abs | NH₂ |
| 170 | TBA | abs | Pro | Phe | His | Statine | Ile | abs | abs | NH₂ |
| 171 | DMA | abs | Pro | Phe | NMHis | LVA | Ile | abs | abs | AMP |
| 172 | TMA | abs | Pro | Phe | NMHis | LVA | Ile | abs | abs | AMP |
| 173 | Boc | abs | abs | Phe | His | LVA | abs | abs | abs | 2HPA |
| 174 | Boc | abs | Pro | Phe | His | LVA | Ile | abs | abs | AMP |
| 175 | Boc | abs | abs | Phe | Nle | LVA | Ile | abs | abs | AMP |

TABLE A-continued

| Cpd | X | A6 | B7 | C8 | D9 | E10/F11 | G12 | H13 | I14 | Z |
|---|---|---|---|---|---|---|---|---|---|---|
| 176 | Ac | FTrp | Pro | Phe | NMHis | Statine | abs | abs | abs | NH2 |
| 177 | Ac | FTrp | Pro | Phe | His | CRC | abs | abs | abs | NH2 |
| 178 | Ac | FTrp | Pro | Phe | His | ASta3R | abs | abs | abs | NH2 |
| 179 | Boc | abs | abs | Phe | His | LVA | abs | abs | abs | AMP |
| 180 | Boc | abs | abs | Phe | His | LVA | abs | abs | abs | MBA |
| 181 | Boc | abs | abs | Phe | His | LVA | abs | abs | abs | NBA |
| 182 | Boc | abs | abs | Phe | His | LVA | abs | abs | abs | CMA |
| 183 | Boc | abs | Pro | Phe | His | LVA | abs | abs | abs | CMA |
| 184 | Boc | abs | Pro | Phe | NMHis | LVA | Ile | abs | abs | OH |
| 185 | Boc | abs | Pro | abs | NMHis | LVA | Ile | abs | abs | AMP |
| 186 | H | Gly | Pro | Phe | NMHis | LVA | Ile | abs | abs | AMP |
| 187 | Ac | FTrp | Pro | Phe | His | LVA | abs | abs | abs | NH2 |

TABLE B

Physicochemical Data

| Compound | Ms[M + H]+ | HPLC Retention Data Time (min.) | Conditions[1] |
|---|---|---|---|
| 1 | 1086 | 15.3 | a |
| 2 | 720 | 12.2 | a |
| 3 | — | 10.1 | d |
| 4 | 872 | 18.5 | a |
| 5 | 1019 | 15.2 | a |
| 6 | 830 | 2.0 | a |
| 7 | 844 | 12.5 | a |
| 8 | 776.4696 | 18.5 | b(i) |
| 9 | 1009 | 2.0 | a |
| 10 | 883 | 16.4 | a |
| 11 | 980 | 15.3 | a |
| 12 | 770 | 7.9 | a |
| 13 | 770 | 7.5 | a |
| 14 | 628 | 13.3 | a |
| 15 | 685 | 4.7 | c(i) |
| 16 | 729 | 11.3 | a |
| 17 | 729 | 11.6 | a |
| 18 | 743 | 12.4 | a |
| 19 | 883 | 18.5 | a |
| 20 | 630 | 13.3 | a |
| 21 | 616 | 13.1 | a |
| 22 | 883 | 16.4 | a |
| 23 | — | 14.1 | d |
| 24 | — | 13.8 | d |
| 25 | 949 | 11.3 | d |
| 26 | 980 | 18.2 | a |
| 27 | 930 | 16.4 | a |
| 28 | 699 | 6.1 | c(ii) |
| 29 | — | 6.3 | d |
| 30 | 1154 | 13.5 | a |
| 31 | — | 13.8 | d |
| 32 | — | 11.1 | d |
| 33 | 992 | 9.2 | d |
| 34 | — | 11.6 | d |
| 35 | — | 11.9 | d |
| 36 | — | 10.2 | d |
| 37 | — | 8.65 | d |
| 38 | — | 9.39 | d |
| 39 | — | 8.4 | d |
| 40 | — | 11.66 | d |
| 41 | — | 11.7 | d |
| 42 | — | 9.22 | d |
| 43 | — | 8.28 | d |
| 44 | — | 9.38 | d |
| 45 | — | 8.75 | d |
| 46 | 902 | 11.5 | c(iii) |
| 47 | 903 | 4.8 | c(iv) |
| 48 | 812 | 4.7 | c(ii) |
| 49 | 844.5359 | 73 | b(ii) |
| 50 | 721 | 4.4 | c(v) |
| 51 | 776.4727 | 28.4 | b(i) |
| 52 | 819 | — | |
| 53 | 629 | 3.9 | c(vi) |
| 54 | 664 | 5.2 | c(ii) |
| 55 | 627 | 5.7 | c(vii) |
| 56 | 721 | 7.8 | c(viii) |
| 57 | — | 7.6 | d |
| 58 | — | 8.1 | d |
| 59 | 747 | 6.34 | d |
| 60 | 636 | 13.7 | a |
| 61 | 636 | 11.8 | a |
| 62 | 636 | 11.7 | a |
| 63 | 781 | 5.0 | c(xxiv) |
| 64 | 812 | 6.1 | c(iv) |
| 65 | 784 | 13.8 | a |
| 66 | 784 | 14.9 | a |
| 67 | 705 | 5.5 | c(vii) |
| 68 | 781 | 7.5 | c(iii) |
| 69 | 756 | 14.0 | a |
| 70 | 756 | 13.9 | a |
| 71 | 784 | 11.5 | a |
| 72 | 1040 | 2.6 | c(ii) |
| 73 | 1050 | 7.0 | c(i) |
| 74 | 915 | 20 | a |
| 75 | 858 | — | |
| 76 | 826 | — | |
| 77 | 847 | 3.1 | c(x) |
| 78 | 984 | 3.1 | c(xi) |
| 79 | 1055 | 4.9 | c(xii) |
| 80 | 997 | 5.1 | c(xiii) |
| 81 | 1074 | 5.4 | c(x) |
| 82 | 1132 | 5.0 | c(xiv) |
| 83 | 1199 | 4.7 | c(xv) |
| 84 | 1198 | 6.0 | c(xvi) |
| 85 | 1109 | 7.3 | c(xvi) |
| 86 | | | |
| 87 | 544.3169 | — | |
| 88 | 473.2892 | 10.8 | b(iv) |
| 89 | 777.4613 | 12.9 | b(i) |
| 90 | 569.3717 | 15.5 | b(iii) |
| 91 | 583.3880 | 22.7 | b(i) |
| 92 | 682.4526 | 7.4 | b(i) |
| 93 | 614.3946 | 8.0 | b(i) |
| 94 | 682.4532 | 6.8 | b(i) |
| 95 | 682.4513 | 5.25, 5.85 | b(i) |
| 96 | 682.4565 | 8.8, 9.3 | b(i) |
| 97 | 1060 | 4.8 | c(xii) |
| 98 | 1198 | 6.0 | c(xvi) |
| 99 | 884 | — | |
| 100 | 1140 | 5.0 | c(xvii) |
| 101 | 830 | 9.0 | c(xviii) |
| 102 | 777 | 8.0 | c(xix) |
| 103 | 777 | — | |
| 104 | 1002 | 4.8 | c(xx) |
| 105 | 762 | 6.5 | c(xxi) |
| 106 | 706 | 4.0 | c(xxii) |
| 107 | 664 | 6.7 | c(xxiii) |
| 108 | 691 | 6.0 | c(viii) |
| 109 | 770 | 7.3 | c(viii) |
| 110 | 762 | 3.4 | c(vii) |
| 111 | 869 | 8.2 | c(xxiv) |
| 112 | 812 | 5.4 | c(vi) |
| 113 | 847 | 5.5 | c(xxiv) |
| 114 | 678.4196 | 6.7 | c(xxiv) |
| 115 | 812.4710 | 5.6 | c(vi) |
| 116 | 833.5255 | 5.4 | c(xxv) |
| 117 | 776.4696 | 6.0 | c(xxv) |
| 118 | 925 | 11.3 | d |
| 119 | 605.4296 | 5.6 | c(ii) |
| 120 | 706.4290 | 13.8 | b(i) |
| 121 | 995 | 11.3 | d |
| 122 | 951 | 4.6 | c(xii) |

TABLE B-continued

| Compound | Ms[M + H]+ | Time (min.) | Conditions[1] |
|---|---|---|---|
| 123 | 917 | 5.6 | c(xix) |
| 124 | 1098 | 7.4 | c(xii) |
| 125 | 788 | — | |
| 126 | 880 | 6.0 | c(xix) |
| 127 | 880 | — | |
| 128 | 844 | 7.3 | c(xx) |
| 129 | 846 | 4.6 | c(xix) |
| 130 | 822 | 11.4 | d |
| 131 | 725 | 10.4 | d |
| 132 | 648 | 10.1 | d |
| 133 | — | 12.52 | d |
| 134 | — | 11.17 | d |
| 135 | — | 12.59 | d |
| 136 | — | 11.23 | d |
| 137 | — | 13.25 | d |
| 138 | — | 11.1 | d |
| 139 | — | 13.78 | d |
| 140 | — | 9.73 | d |
| 141 | — | 11.25 | d |
| 142 | — | 10.48 | d |
| 143 | — | 11.72 | d |
| 144 | — | 10.47 | d |
| 145 | — | 9.39 | d |
| 146 | 992 | 9.31 | d |
| 147 | — | 17.27 | d |
| 148 | — | 4.3 | d |
| 149 | — | 7.2 | d |
| 150 | — | 13.09 | d |
| 151 | — | 10.40 | d |
| 152 | — | 10.51 | d |
| 153 | — | 10.40 | d |
| 154 | — | 11.30 | d |
| 155 | — | 11.45 | d |
| 156 | — | 11.83 | d |
| 157 | — | 8.9 | d |
| 158 | — | 9.2 | d |
| 159 | — | 5.02 | d |
| 160 | — | 5.08 | d |
| 161 | | 7.9 | d |
| 162 | | 8.7 | d |
| 163 | 1086 | 15.3 | b |
| 164 | 1144 | 17.0 | b |
| 165 | 884 | 3.6 | b |
| 166 | 874 | 12.8 | b |
| 167 | 930 | 18.1 | b |
| 168 | 704.4364 | 12.3 | a |
| 169 | 794.4115 | 11.9 | e |
| 170 | 767.3265 | 11.93 | e |
| 171 | 900.5685 | 15.2 | a |
| 172 | 914.5831 | 15.3 | a |
| 173 | 673.4293 | 7.51 | b(i) |
| 174 | 916.5634 | 11.2 | a |
| 175 | 795.5395 | 6.0 | f(ii) |
| 176 | 826 | 13.7 | e |
| 177 | | | |
| 178 | | | |
| 179 | 706 | 15.4 | a |
| 180 | 685.4645 | 6.7 | c(xxiv) |
| 181 | 671.4503 | 7.2 | c(vi) |
| 182 | 711.4776 | 10.2 | a |
| 183 | 808.5300 | 11.1 | a |
| 184 | 840.5193 | 13.5 | f(i) |
| 185 | 783.5106 | 10.6 | a |
| 186 | 887.5549 | 12.4 | a |
| 187 | 867.4643 | 11.19 | e |

The k' value is calculated for the conditions indicated as the retention time of the compound minus the retention time of the solvent front and dividing this difference by the retention time of the solvent.

1. HPLC conditions:
   a. Brownlee RP-18 Spheri-10 18-10A, 25 cm×4.6 mm ID column, μM, UV detection at 254 nm, eluant: 90% methanol, 10% aqueous pH 3 phosphate buffer, flow rate 1.5 ml/min.
   b. Brownlee RP-18 Spheri-5, 25 cm×4.6 mm ID column, flow rate 2ml/min, solvent A is 90% pH 3 phosphate buffer, 10% acetonitrile ($CH_3CN$), solvent B is 10% THF, 10% pH 3 phosphate buffer and 80% $CH_3CN$, conditions: (i) 25% A changing to 0% A during 20 min using Waters Model 680 Automated Gradient Controller curve 8; (ii) 100% B; (iii) 50% A changing to 25% A otherwise as in (i); (iv) isocratic 75% $CH_3CN$-25% pH 3 phosphate buffer.
   c. The value reported is not a time in minutes but rather is k'. 25 cm×4.6 mm ID column: EM (EMerck Hibor LiChrosorb RP-181, W (Waters μBondapak phenyl, or BR (Brownlee RP-18 Spheri-10, UV detection at 225 nm, flow rate 1.5 ml/min, solvent system I; solvent A is 0.2% TFA in water and solvent B is 0.2% TFA in $CH_3CN$ or solvent system II: solvent A is 98% water, 1% $CH_3CN$, 1% $H_3PO_4$, 125 mM $NaH_2PO_4$; conditions: (i)BR, II 35%A 65%B; (ii) BR, II 40%A 60%B; (iii) W,II 65%A 35%B; (iv) BR, II 20%A 80%B; (v) BR, II 25%A 75%B; (vi) BR, II 50%A 50%B; (vii) BR, II 55%A 45%B; (viii) BR, II 60%A 40%B; (ix) EM, I 50%A 50%B; (x) EM, I 52.5%A 47.5%B; (xi) EM, I 65%A 35%B; (xii) EM, I 55%A 45%B; (xiii) EM, I 62.5%A 37.5%B; (xiv) EM, I 43%A 57%B; (xv) EM, I 42%A 58%B; (xvi) EM, I 45%A 55%B; (xvii) EM, II 50%A 40%B; (xviii) EM, II 60%A 40%B; (xix) EM, I 60%A 40%B; (xx) W, I 71%A 29%B; (xxi) W, I 67.5%A 32.5%B; (xxii) W, I 75%A 25%B; (xxiii) W, I 78%A 22%B; (xxiv) BR, II 45%A 55%B; (xxv) BR, II 47.5%A 52.5%B; (xxvi) BR, II 57.5%A 42.5%B.
   d. Retention time was determined on $C_{18}$ reverse phase SYNCHROPAK analytical HPLC using the following gradient system: 83.3% A and 16.7% B for 2 min; 83.3%A and 16.7% B changing to 100%B during 20 minutes; flow rate 1.5 ml/min, pressure about 1500 psi; UV detection at 220 or 280 nm; solvent A is 10% $CH_3CN$, 0.2% TFA, the rest water; solvent B is 70% $CH_3CN$, 0.2% TFA, the rest water.
   e. Retention time was determined on a Separations Group Videk-$C_{18}$ column (25 cm×4.6 mm id, 10 micron particle size) otherwise using the same conditions as in footnote d. above.
   f. Retention time was determined as in footnote a. above but using: (i) 75% $CH_3OH$, 25% aqueous pH 3 phosphate buffer; (ii) 80% methanol, 20% aqueous pH 3 phosphate buffer.

FORMULAS

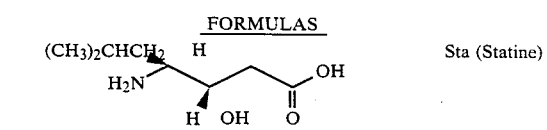

Sta (Statine)

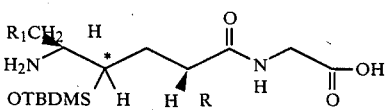

I

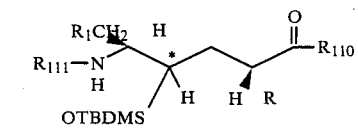

$I_1$

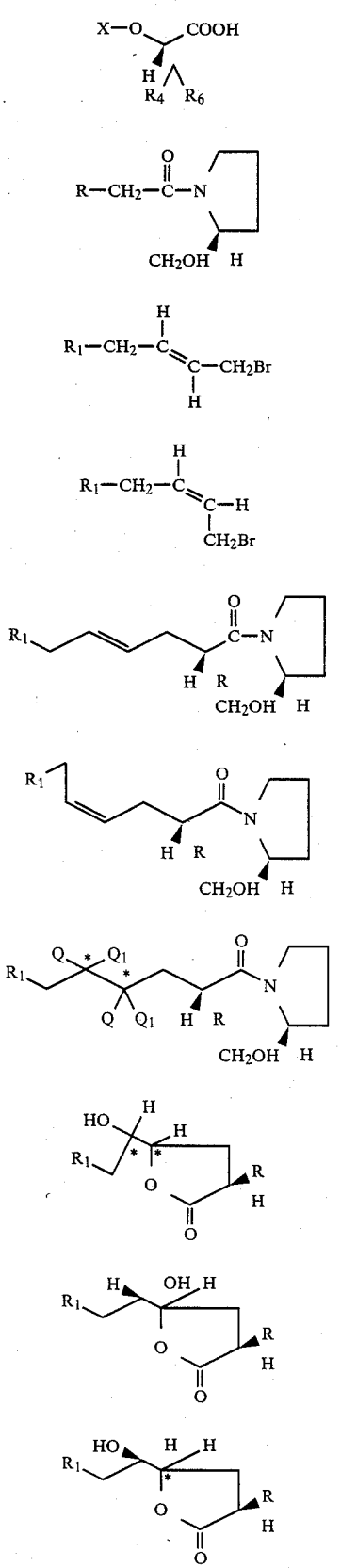
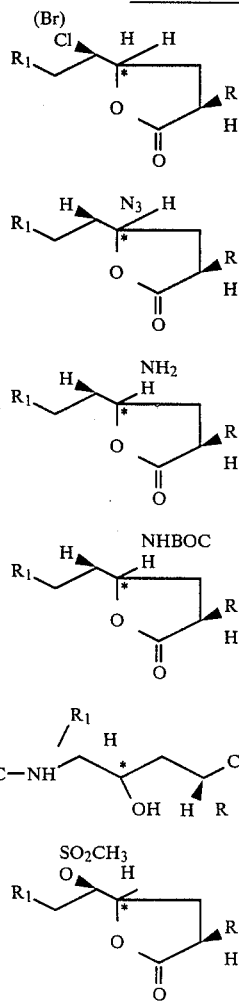
CHART A
SCHEME I 4,880,781
-continued
CHART A
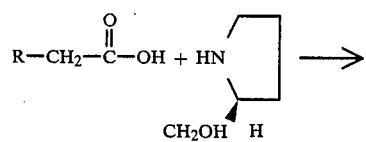
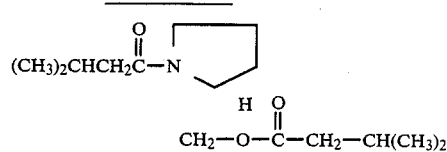
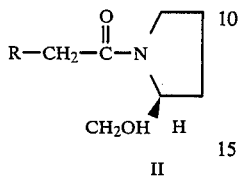
II
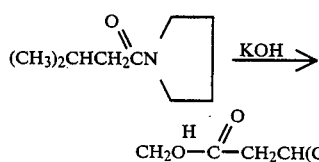
SCHEME I$_2$
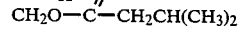
SCHEME I$_1$
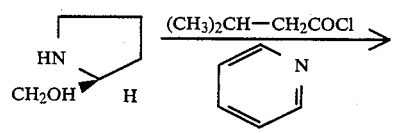
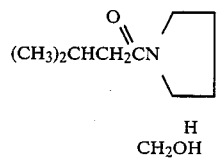
CHART B
SCHEME II
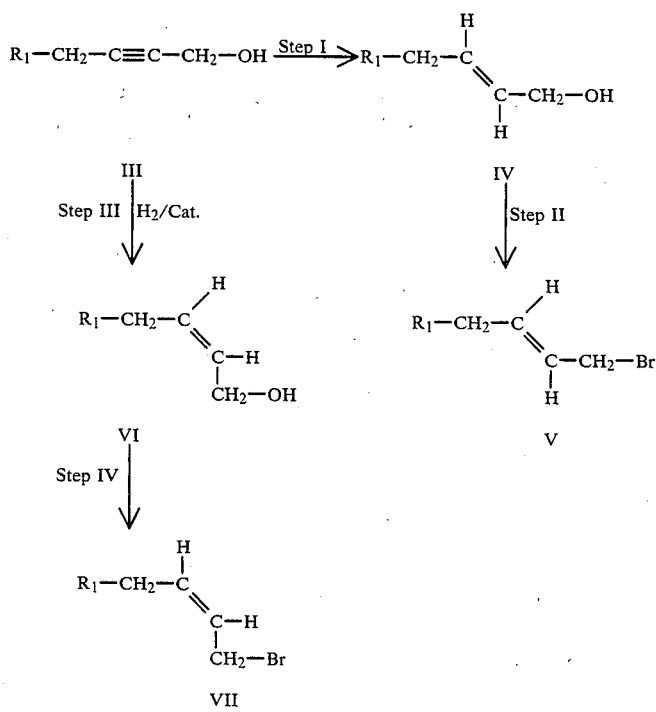
SCHEME II$_1$
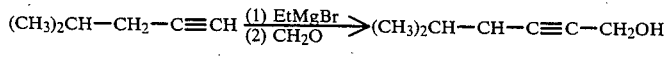
III wherein R$_1$ is isopropyl
SCHEME II$_2$
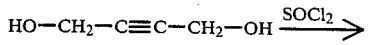

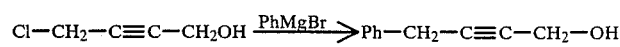
III wherein $R_1$ is phenyl
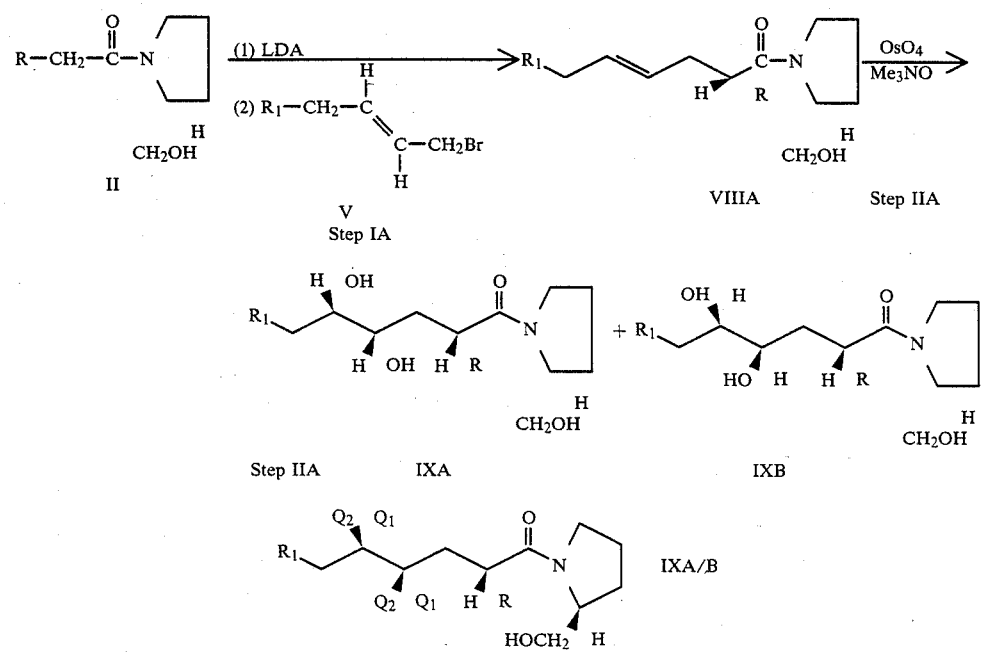
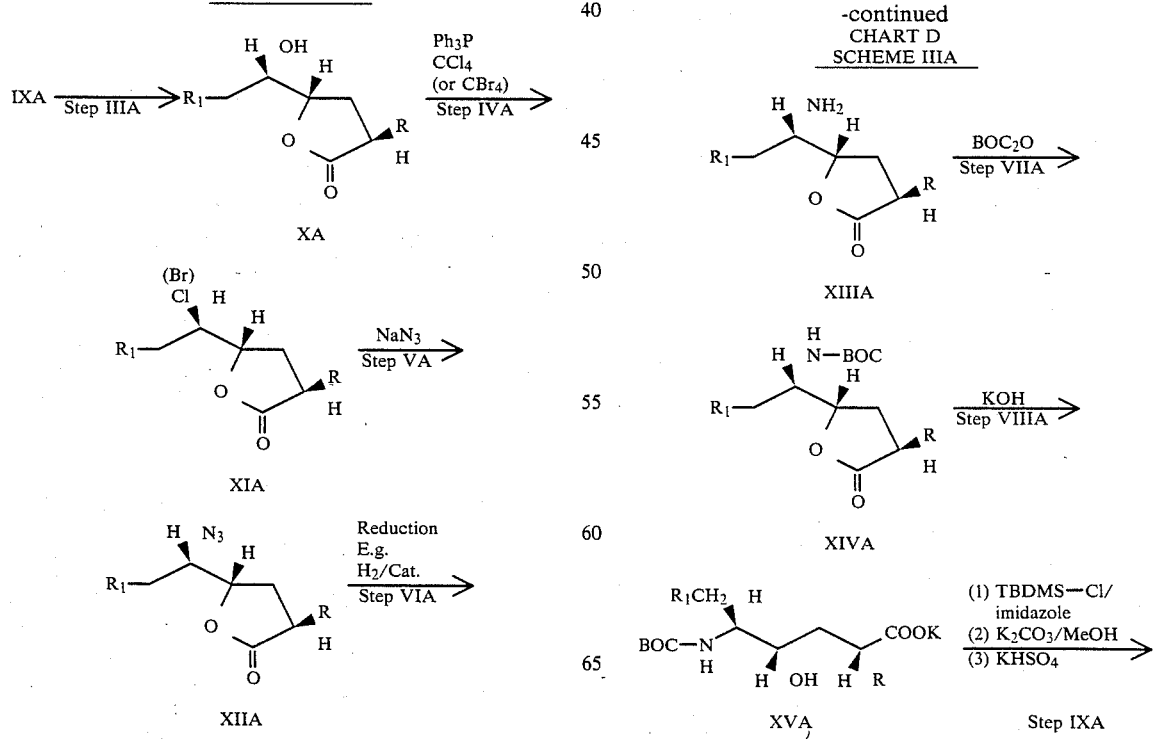

-continued
CHART D
SCHEME IIIA
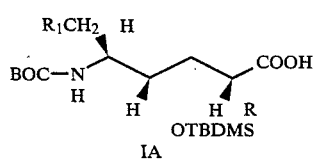
IA
CHART E
SCHEME IIIB
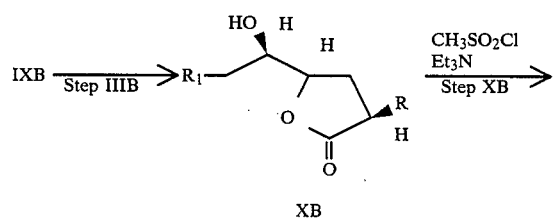
XB
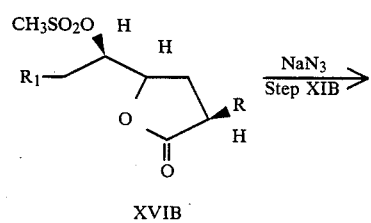
XVIB
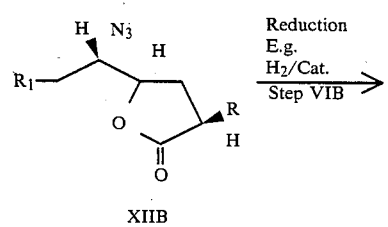
XIIB
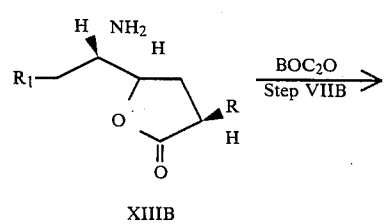
XIIIB
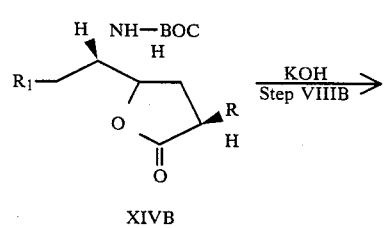
XIVB
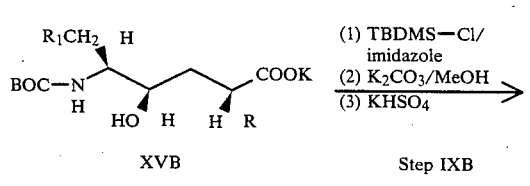
XVB   Step IXB
-continued
CHART E
SCHEME IIIB
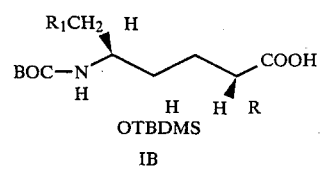
IB
CHART F
SCHEME III C/D
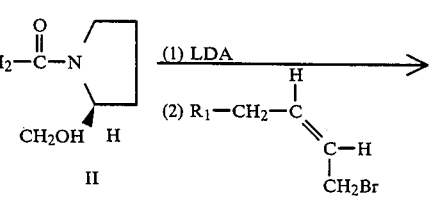
Step IB    VII
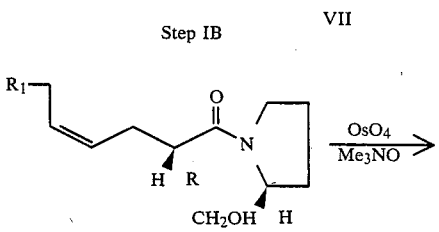
VIIIB    Step IIB
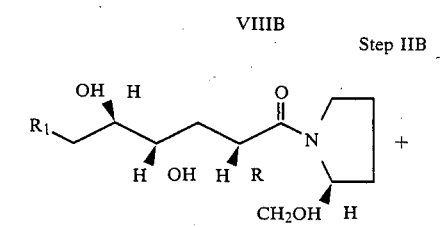
IXC
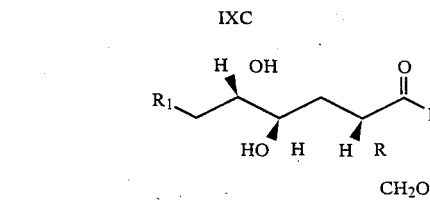
IXD
IXC/D
CHART G
SCHEME IIIC
IXC ⟶   Step IIIC 4,880,781
-continued
CHART G
SCHEME IIIC
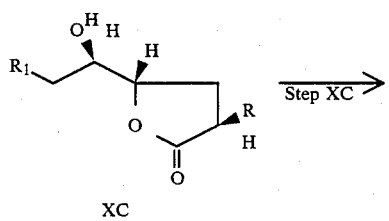
XC
→ Step XC
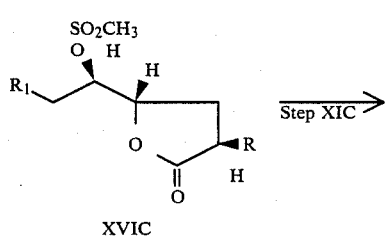
XVIC
→ Step XIC
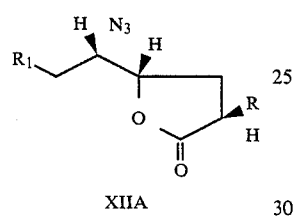
XIIA
CHART H
SCHEME IIID
IXD →(Step IID)→ 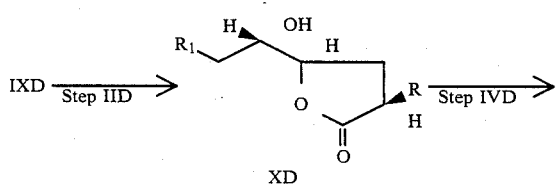 →(Step IVD)→
XD
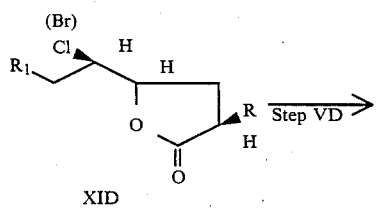
XID
→ Step VD →
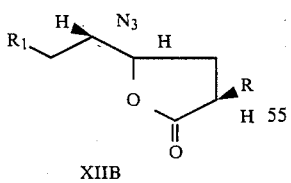
XIIB
CHART I
SCHEME IV
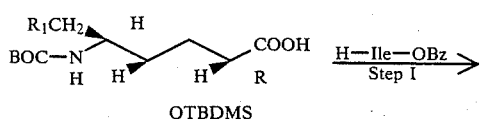
I
-continued
CHART I
SCHEME IV
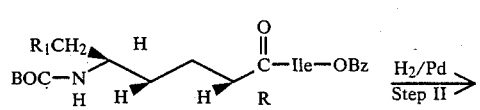
→ H$_2$/Pd Step II →
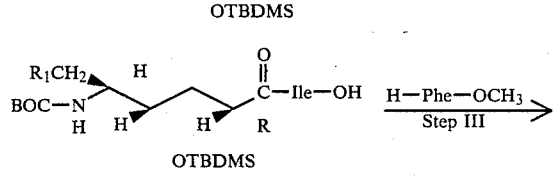
XXIV
→ H—Phe—OCH$_3$ Step III →
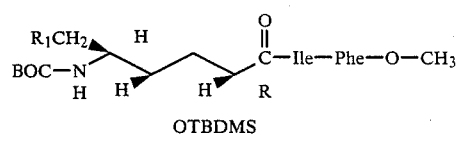
XXI
CHART J
SCHEME V
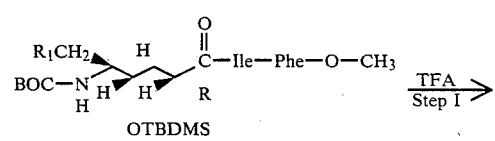
XXI
→ TFA Step I →
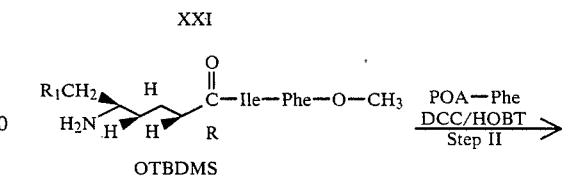
H$_2$N- XXII
→ POA—Phe DCC/HOBT Step II →
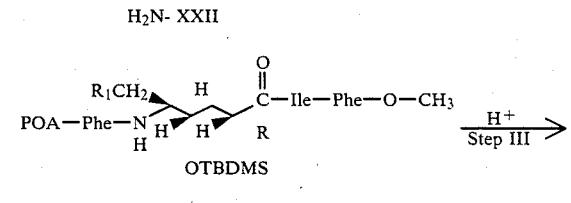
→ H$^+$ Step III →
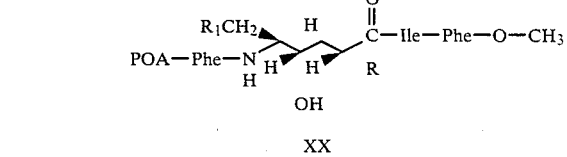
XX
CHART K
SCHEME V'
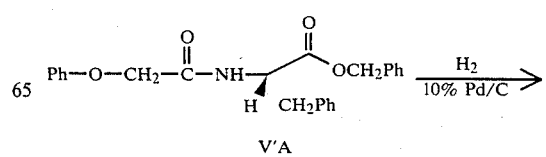
V'A
→ H$_2$ 10% Pd/C →

-continued
CHART K
SCHEME V'
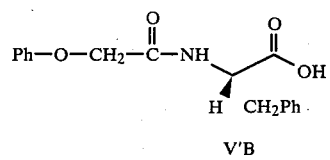
V'B
CHART L
SCHEME VI
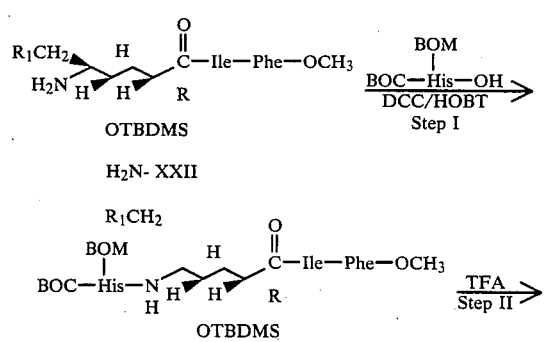
-continued
CHART L
SCHEME VI
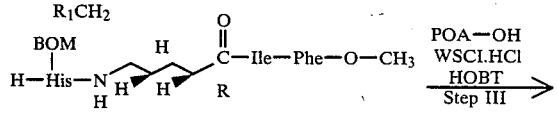
H$_2$N-XXIII
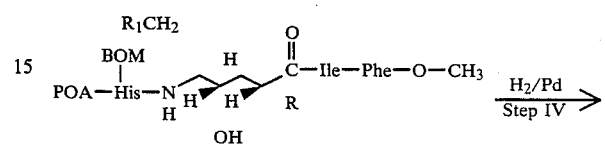
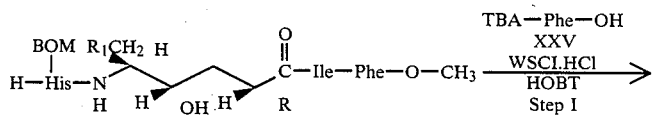
XX$_2$
CHART M
SCHEME VII
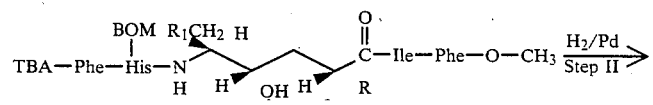
H$_2$N—XXIII
(further structures)
XX$_3$
CHART N
SCHEME VIII
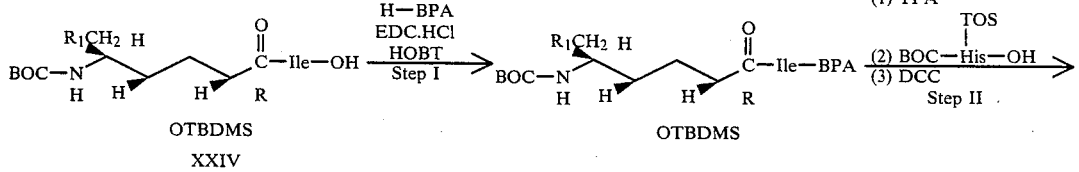
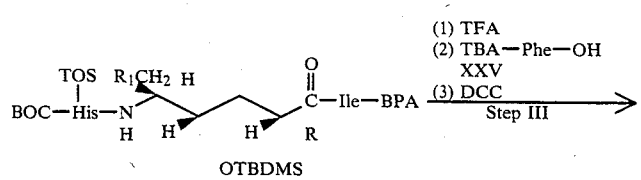

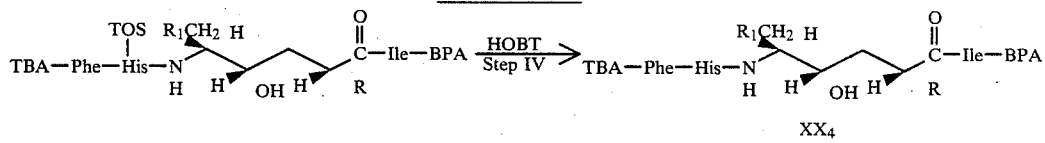
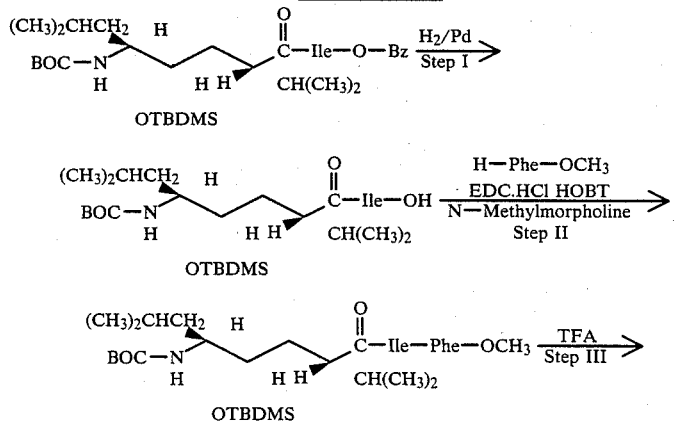
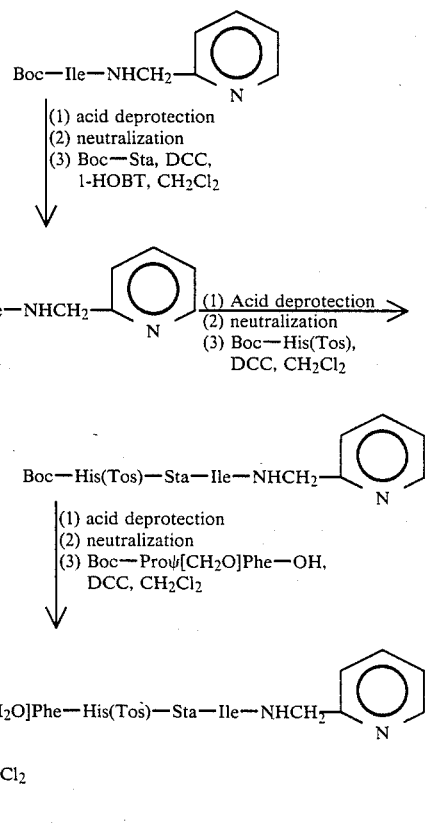
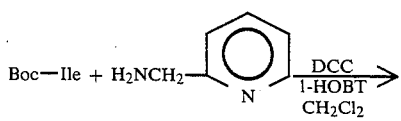

CHART Q
SCHEME Q-I

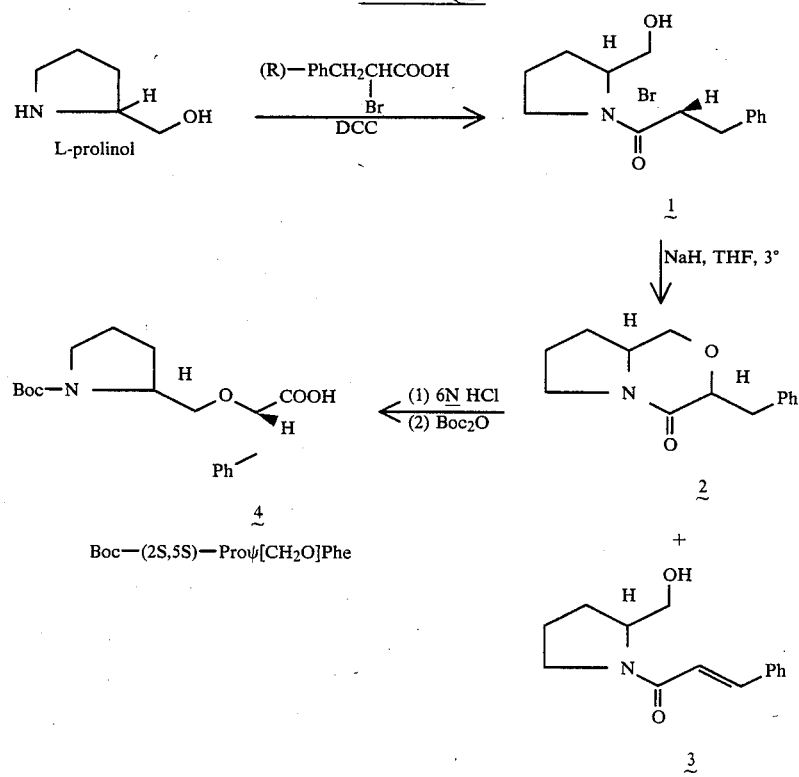

We claim:
1. A renin inhibitory peptide of the formula X–A$_6$–B$_7$–C$_8$–D$_9$–E$_{10}$–F$_{11}$–G$_{12}$–H$_{13}$–I$_{14}$–Z,
  wherein X is
  (a) hydrogen,
  (b) C$_1$–C$_5$alkyl
  (c) R$_5$–O–CH$_2$–C(O)–,
  (d) R$_5$–CH$_2$–O–C(O)–,
  (e) R$_5$–O–C(O)–,
  (f) R$_5$–(CH$_2$)$_n$–C(O)–,
  (g) R$_4$N(R$_4$)–(CH$_2$)$_n$–C(O),
  (h) R$_5$–SO$_2$–(CH$_2$)$_q$–C(O)–, or
  (i) R$_5$–SO$_2$–(CH$_2$)$_q$–O–C(O)–;
  wherein A$_6$ is absent or a divalent moiety of the formula XL$_1$, XL$_2$, or XL$_{2a}$

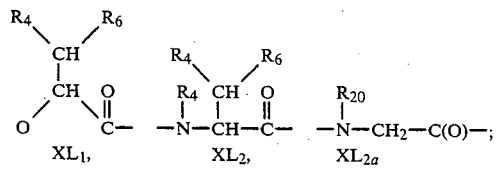

wherein B$_7$ is absent or a divalent moiety of the formula XL$_b$

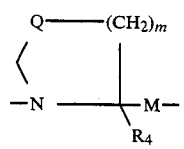

wherein C$_8$ is absent or a divalent moiety of the formula XL$_1$, XL$_2$ or XL$_{2a}$,

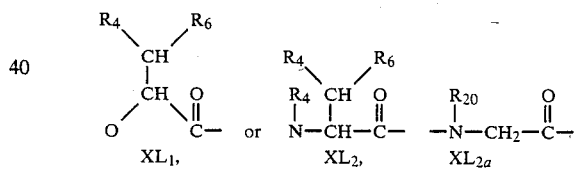

wherein D$_9$ is a divalent moiety of the formula XL$_3$,

wherein E$_{10}$–F$_{11}$ is a divalent moiety of the formula XL$_6$, XL$_{6a}$, XL$_{6b}$, XL$_{6c}$, XL$_{6d}$, or XL$_{6e}$,

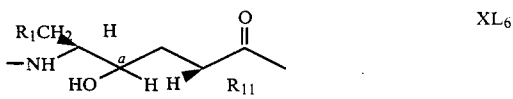

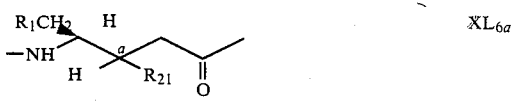

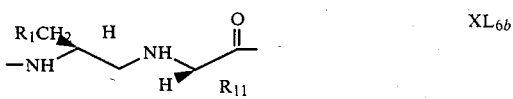

-continued

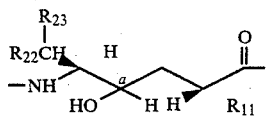   XL$_{6c}$

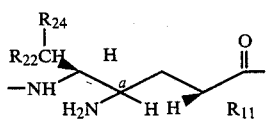   XL$_{6d}$

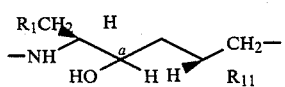   XL$_{6e}$ wherein * indicates an asymmetric center which is either in the R or S configuration;
wherein G$_{12}$ is absent or a divalent moiety of the formula XL$_4$ or XL$_{4a}$

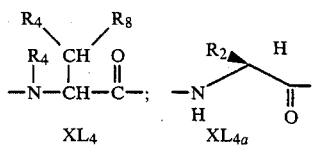

wherein H$_{13}$ is absent or a divalent moiety of the formula XL$_4$

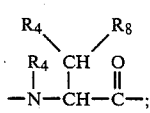   XL$_4$ wherein I$_{14}$ is absent or a divalent moiety of the formula XL$_5$

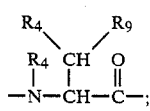   XL$_5$ wherein Z is
 (a) —O—R$_{10}$,
 (b) —N(R$_4$)R$_{14}$, or
 (c) C$_4$-C$_8$cyclic amino;
wherein R is
 (a) isopropyl,
 (b) isobutyl,
 (c) phenylmethyl, or
 (d) C$_3$-C$_7$cycloalkyl;
wherein R$_1$ is
 (a) hydrogen,
 (b) C$_1$-C$_5$alkyl,
 (c) aryl,
 (d) C$_3$-C$_7$cycloalkyl,
 (e) —Het,
 (f) C$_1$-C$_3$alkoxy, or
 (g) C$_1$-C$_3$alkylthio;
wherein R$_2$ is
 (a) hydrogen, or
 (b) —CH(R$_3$)R$_4$;
wherein R$_3$ is
 (a) hydrogen,
 (b) hydroxy,
 (c) C$_1$-C$_5$alkyl,
 (d) C$_3$-C$_7$cycloalkyl,
 (e) aryl,
 (f) —Het,
 (g) C$_1$-C$_3$alkoxy, or
 (h) C$_1$-C$_3$alkylthio;
wherein R$_4$ at each occurrence is the same or different and is
 (a) hydrogen, or
 (b) C$_1$-C$_5$alkyl;
wherein R$_4$ in D$_9$ is C$_1$-C$_5$ alkyl;
wherein R$_5$ is
 (a) C$_1$-C$_6$alkyl,
 (b) C$_3$-C$_7$cycloalkyl,
 (c) aryl,
 (d) —Het, or
 (e) 5-oxo-2-pyrrolidinyl;
wherein R$_6$ is
 (a) hydrogen,
 (b) C$_1$-C$_5$alkyl,
 (c) —(CH$_2$)$_p$—aryl,
 (d) —(CH$_2$)$_p$—Het,
 (e) C$_3$-C$_7$cycloalkyl, or
 (f) 1- or 2-adamantyl;
wherein R$_7$ is
 (a) hydrogen,
 (b) C$_1$-C$_5$alkyl,
 (c) hydroxy,
 (d) amino C$_1$-C$_4$alkyl—,
 (e) guanidinyl C$_1$-C$_3$alkyl-,
 (f) aryl,
 (g) —Het,
 (h) methylthio,
 (i) C$_3$-C$_7$cycloalkyl, or
 (j) amino;
wherein R$_7$ in D$_9$ is 1H-imidazol-4-yl;
wherein R$_8$ is
 (a) hydrogen,
 (b) C$_1$-C$_5$alkyl,
 (c) hydroxy,
 (d) aryl,
 (e) —Het,
 (f) guanidinyl C$_1$-C$_3$alkyl-, or
 (g) C$_3$-C$_7$cycloalkyl;
wherein R$_9$ is
 (a) hydrogen,
 (b) hydroxy,
 (c) amino C$_1$-C$_4$alkyl-, or
 (d) guanidinyl C$_1$-C$_3$alkyl-;
wherein R$_{10}$ is
 (a) hydrogen,
 (b) C$_1$-C$_5$alkyl,
 (c) —(CH$_2$)$_n$R$_{16}$,
 (d) —(CH$_2$)$_n$R$_{17}$,
 (e) C$_3$-C$_7$cycloalkyl,
 (f) a pharmaceutically acceptable cation,
 (g) —(CHR$_{25}$)—CH$_2$—R$_{15}$, or
 (h) —CH$_2$—(CHR$_{12}$)—R$_{15}$;
wherein R$_{11}$ is —R or —R$_2$;
wherein R$_{12}$ is —(CH$_2$)$_n$—R$_{13}$;
wherein R$_{13}$ is
 (a) aryl,
 (b) amino,
 (c) mono-, di or tri-C$_1$-C$_3$alkylamino,
 (d) —Het,
 (e) C$_1$-C$_5$alkyl
 (f) C$_3$-C$_7$cycloalkyl,
 (g) C$_1$-C$_5$alkenyl, (h) $C_3$-$C_7$cycloalkenyl,
(i) hydroxy,
(j) $C_1$-$C_3$alkoxy,
(k) $C_1$-$C_3$alkanoyloxy,
(l) mercapto,
(m) $C_1$-$C_3$alkylthio,
(n) —COOH,
(o) —CO—O—$C_1$-$C_6$alkyl,
(p) —CO—O—$CH_2$—($C_1$-$C_3$alkyl)—N($C_1$-$C_3$alkyl)$_2$,
(q) —CO—$NR_{22}R_{26}$;
(r) $C_4$-$C_7$cyclic amino,
(s) $C_4$-$C_7$cycloalkylamino,
(t) guanidyl,
(u) cyano,
(v) N-cyanoguanidyl,
(w) cyanoamino,
(x) (hydroxy $C_2$-$C_4$alkyl)amino, or
(y) di-(hydroxy $C_2$-$C_4$alkyl)amino;
wherein $R_{14}$ is
(a) hydrogen,
(b) $C_1$-$C_{10}$alkyl,
(c) —$(CH_2)_n$—$R_{18}$,
(d) —$(CH_2)_n$—$R_{19}$,
(e) —$(CHR_{25})$—$CH_2$—$R_{15}$,
(f) —$CH_2$—$(CHR_{12})$—$R_{15}$,
(g) (hydroxy $C_1$-$C_8$alkyl), or
(h) ($C_1$-$C_3$alkoxy)$C_1$-$C_8$alkyl;
wherein $R_{15}$ is
(a) hydroxy,
(b) $C_3$-$C_7$cycloalkyl,
(c) aryl,
(d) amino,
(e) mono-, di-, or tri- $C_1$-$C_3$alkylamino,
(f) mono- or di-[hydroxy $C_2$-$C_4$alkyl]amino,
(g) —Het,
(h) $C_1$-$C_3$alkoxy-,
(i) $C_1$-$C_3$alkanoyloxy-,
(j) mercapto,
(k) $C_1$-$C_3$alkylthio-,
(l) $C_1$-$C_5$alkyl,
(m) $C_4$-$C_7$cyclic amino,
(n) $C_4$-$C_7$cycloalkylamino,
(o) $C_1$-$C_5$alkenyloxy,
(p) $C_3$-$C_7$cycloalkenyl;
wherein $R_{16}$ is
(a) aryl,
(b) amino,
(c) mono- or di- $C_1$-$C_3$alkylamino,
(d) hydroxy,
(e) $C_3$-$C_7$cycloalkyl,
(f) $C_4$-$C_7$cyclic amino, or
(g) $C_1$-$C_3$alkanoyloxy;
wherein $R_{17}$ is
(a) —Het,
(b) $C_1$-$C_5$alkenyl,
(c) $C_3$-$C_7$cycloalkenyl,
(d) $C_1$-$C_3$alkoxy,
(e) mercapto,
(f) $C_1$-$C_3$alkylthio,
(g) —COOH,
(h) —CO—O—$C_1$-$C_6$alkyl,
(i) —CO—O—$CH_2$—($C_1$-$C_3$alkyl)—N($C_1$-$C_3$alkyl)$_2$,
(j) —CO—$NR_{22}R_{26}$,
(k) tri-$C_1$-$C_3$alkylamino,
(l) guanidyl,
(m) cyano,
(n) N-cyanoguanidyl,
(o) (hydroxy $C_2$-$C_4$alkyl)amino,
(p) di-(hydroxy $C_2$-$C_4$alkyl)amino, or
(q) cyanoamino;
wherein $R_{18}$ is
(a) amino,
(b) mono-, or di- $C_1$-$C_3$alkylamino,
(c) $C_4$-$C_7$cyclic amino, or
(d) $C_4$-$C_7$cycloalkylamino;
wherein $R_{19}$ is
(a) aryl,
(b) —Het,
(c) tri-$C_1$-$C_3$alkylamino,
(d) $C_3$-$C_7$cycloalkyl,
(e) $C_1$-$C_5$alkenyl,
(f) $C_3$-$C_7$cycloalkenyl,
(g) hydroxy,
(h) $C_1$-$C_3$alkoxy,
(i) $C_1$-$C_3$alkanoyloxy,
(j) mercapto,
(k) $C_1$-$C_3$alkylthio,
(l) —COOH,
(m) —CO—O—$C_1$-$C_6$alkyl,
(n) —CO—O—$CH_2$—($C_1$-$C_3$alkyl)—N($C_1$-$C_3$alkyl)$_2$,
(o) —CO—$NR_{22}R_{26}$,
(p) guanidyl,
(q) cyano,
(r) N-cyanoguanidyl,
(s) cyanoamino,
(t) (hydroxy $C_2$-$C_4$alkyl)amino, (u) di-(hydroxy $C_2$-$C_4$alkyl)amino; or
(v) —$SO_3H$;
wherein $R_{20}$ is
(a) hydrogen,
(b) $C_1$-$C_5$alkyl, or
(c) aryl-$C_1$-$C_5$alkyl;
wherein $R_{21}$ is
(a) —$NH_2$, or
(b) —OH;
wherein $R_{22}$ is
(a) hydrogen, or
(b) $C_1$-$C_3$alkyl;
wherein $R_{23}$ is
(a) —$(CH_2)_n$—OH,
(b) —$(CH_2)_n$—$NH_2$,
(c) aryl, or
(d) $C_1$-$C_3$alkyl;
wherein $R_{24}$ is
(a) —$R_1$,
(b) —$(CH_2)_n$—OH, or
(c) —$(CH_2)_n$—$NH_2$;
wherein $R_{25}$ is —$(CH_2)_n$—$R_{13}$;
wherein $R_{26}$ is
(a) hydrogen,
(b) $C_1$-$C_3$alkyl, or
(c) phenyl-$C_1$-$C_3$alkyl;
wherein m is one or two;
wherein for each occurrence n is independently an integer of zero to five, inclusive;
wherein p is zero to 2 inclusive;
wherein q is 1 to 5, inclusive;
wherein Q is
(a) —$CH_2$—,
(b) —CH(OH)—,
(c) —O—, or
(d) —S—; and
wherein M is (a) —CO—, or
(b) —CH$_2$—;
wherein aryl is phenyl or naphthyl substituted by zero to 3 of the following:
(a) C$_1$-C$_3$alkyl,
(b) hydroxy,
(c) C$_1$-C$_3$alkoxy,
(d) halo,
(e) amino,
(f) mono- or di-C$_1$-C$_3$alkylamino,
(g) —CHO,
(h) —COOH,
(i) COOR$_{26}$,
(j) COHR$_{26}$,
(k) nitro,
(l) mercapto,
(m) C$_1$-C$_3$alkylthio,
(n) C$_1$-C$_3$alkylsulfinyl,
(o) C$_1$-C$_3$alkylsulfonyl,
(p) C$_1$-C$_3$alkylsulfonyl—N(R$_4$)—
(q) SO$_3$H,
(r) SO$_2$NH$_2$,
(s) —CN, or
(t) —CN$_2$NH$_2$;
wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
(i) C$_1$-C$_6$alkyl,
(ii) hydroxy,
(iii) trifluoromethyl,
(iv) C$_1$-C$_4$alkoxy,
(v) halo,
(vi) aryl,
(vii) aryl C$_1$-C$_4$alkyl-,
(viii) amino, and
(ix) mono- or di-C$_1$-C$_4$alkylamino; with the overall provisos that
(1) E$_{10}$-F$_{11}$ is XL$_{6a}$, XL$_{6b}$, XL$_{6c}$, XL$_{6d}$, or XL$_{6e}$ only when at least one of the following occurs:
(i) A$_6$ is present and
(A) A$_6$ is XL$_1$ or
(B) A$_6$ is XL$_2$ wherein R$_6$ is Het which is N$^{in}$-formyl-Trp,
(ii) B$_7$ is present and R$_4$ of B$_7$ is other than hydrogen,
(iii) C$_8$ is present and is XL$_1$,
(iv) D$_9$ is N$_\alpha$-methyl-histidine,
(v) B$_7$ and C$_8$ both are present and B$_7$ is XL$_b$ wherein M is —CH$_2$— and C$_8$ is XL$_1$; or
(vi) X is R$_5$—SO$_2$—(CH$_2$)$_q$—C(O)— or R$_5$—SO$_2$—C(CH$_2$)$_q$—OC(O)—;
(2) E$_{10}$F$_{11}$ is XL$_{6e}$ only when G$_{12}$, H$_{13}$ and I$_{14}$ are absent;
(3) B$_7$C$_8$D$_9$ is Pro-Phe-His, E$_{10}$F$_{11}$ is XL$_6$, R$_1$ is isopropyl, or isobutyl; and R$_{11}$ is isopropyl, isobutyl, or benzyl, only when one of the following occurs:
(a) only 1 of G$_{12}$, H$_{13}$, and I$_{14}$ is present;
(b) G$_{12}$ is other than D or L val or D or L Ile;
(c) H$_{13}$ is other than D or L Tyr, D or L Phe, or D or L His; or
(d) A$_6$ is FTrp or XL$_1$;
(4) R$_{16}$ or R$_{17}$ is an amino-containing substituent, hydroxy, mercapto, or —Het bonded through the hetero atom only when n for that substituent is an integer from two to five, inclusive;
(5) R$_{18}$ or R$_{19}$ is hydroxy, mercapto, or amino, or a monosubstituted nitrogen containing group bonded through the nitrogen only when n is not one;
(6) A$_6$, B$_7$, C$_8$, H$_{13}$ and I$_{14}$ are all absent, D$_9$ and G$_{12}$ are both present, and —NR$_4$— of D$_9$ is —NH— and Z is —OR$_{10}$ and R$_{10}$ is hydrogen, C$_1$-C$_5$alkyl, or —(CH$_2$)$_m$—R$_{16}$ or Z is —N(R$_4$)R$_{14}$ and R$_{14}$ is hydrogen, C$_1$-C$_{10}$alkyl or —(CH$_2$)$_n$—R$_{18}$, or Z is C$_4$-C$_8$cyclic amino, only when R$_5$—(CH$_2$)$_n$— is other than C$_1$-C$_8$alkyl, C$_5$-C$_7$cycloalkyl or aryl;
(7) A$_6$, B$_7$, C$_8$, D$_9$, H$_{13}$, I$_{14}$ are all absent and G$_{12}$ is present only when Z is —OR$_{10}$ and R$_{10}$ is —(CH$_2$)$_n$—R$_{17}$, —(CHR$_{25}$)—CH$_2$R$_{15}$ or —CH$_2$—(CHR$_{12}$)—R$_{15}$ or when Z is —N(R$_4$)R$_{14}$ and R$_{14}$ is —(CH$_2$)$_n$—R$_{19}$, —(CHR$_{25}$)— CH$_2$R$_{15}$, or —CH$_2$—(CHR$_{12}$)—R$_{15}$;
(8) R$_{12}$ is —(CH$_2$)$_n$—R$_{13}$ and n is zero and both R$_{13}$ and R$_{15}$ are oxygen-, nitrogen-, or sulfur-containing substituents bonded through the hetero atom, only when the hetero atom is not also bonded to hydrogen;
(9) when R$_{12}$ is —(CH$_2$)$_n$—R$_{13}$ and n is zero, then R$_{13}$ and R$_{15}$ cannot both be —COOH;
(10) R$_{25}$ is —(CH$_2$)$_n$—R$_{13}$ and n is zero only when R$_{13}$ is other than a primary or secondary nitrogen-containing group hydroxy or mercapto group or when R$_4$ of —N(R$_4$)R$_{14}$ is other than hydrogen;
(11) Z is C$_4$-C$_8$cyclic amino, only when at least one of G$_{12}$, H$_{13}$, and I$_{14}$ is present;
(12) R$_{17}$ or R$_{19}$ is —Het, only when —Het is other than cyclic amino;
(13) R$_{17}$ or R$_{19}$ is —COOH only when n for that moiety is other than zero; and
(14) at least one of A$_6$, B$_7$, C$_8$, D$_9$, G$_{12}$, H$_{13}$ or I$_{14}$ must be present;
or a carboxy-, amino-, or other reactive group-protected form
or a pharmaceutically acceptable acid addition salt thereof.

2. A compound of claim 1 wherein C$_8$ is XL$_1$.
3. A compound of claim 1 wherein A$_6$ is XL$_2$ wherein R$_6$ is N$^{in}$-formyl-3-indolyl.
4. A compound of claim 1 wherein D$_9$ is XL$_3$ wherein R$_4$ of —N(R$_4$)— is methyl.
5. A compound of claim 1 wherein E$_{10}$-F$_{11}$ is XL$_6$.
6. A compound of claim 2 wherein A$_6$ and B$_7$ are absent, D$_9$ is XL$_3$, and E$_{10}$F$_{11}$ is XL$_6$ or XL$_{6a}$.
7. A compound of claim 3 wherein A$_6$ is XL$_2$, wherein R$_6$ is N$^{in}$-formyl-3-indolyl, B$_7$ is XL$_b$, C$_8$ is XL$_2$, D$_9$ XL$_3$, and E$_{10}$-F$_{11}$ is XL$_6$.
8. A compound of claim 4 wherein A$_6$ is absent or XL$_2$, B$_7$ is absent or XL$_b$ wherein M is —CO—, D$_9$ is XL$_3$ wherein R$_4$ of —N(R$_4$)— is methyl, E$_{10}$-F$_{11}$ is XL$_6$, or XL$_{6a}$ and G$_{12}$ is XL$_{4a}$.
9. A compound of claim 5, wherein A$_6$ and B$_7$ are absent, E$_{10}$-F$_{11}$ is XL$_6$, and G$_{12}$ is XL$_{4a}$.
10. Ac-PLA-NMHis-LVA-Ile-AMP, a compound of claim 6, or a pharmaceutically acceptable acid addition salt thereof.
11. A compound of claim 3 selected from the group consisting of:
Ac-FTrp-Pro-Phe-NMHis-Statine-Ile-NH$_2$;
Ac-FTrp-Pro-Phe-NMHis-LVA-Ile-NH$_2$;
Ac-FTrp-Pro-Phe-NMHis-PRP-NH$_2$;

or a pharmaceutically acceptable acid addition salt thereof.

12. A compound of claim 4 selected from the group consisting of:
Boc-Pro-Phe-NMHis-LVA-Ile-AMP;
Boc-Phe-NMHis-LVA-Ile-AMP;
Ac-FTrp-Pro-Phe-NMHis-LVA-IleNH$_2$;
Ac-FTrp-Pro-Phe-NMHis-LVA-Ile-AMP;
BOC-FTrp-Pro-Phe-NMHis-LVA-Ile-AMP; and
TBA-Phe-NMHis-LVA-Ile-AMP;
or a pharmacologically acceptable acid addition salt thereof.

13. A method for treating or preventing hypertension in a mammal susceptible to or experiencing hypertension comoprising the oral administration of an amount effective to treat hypertension of a pharmaceutically acceptable acid addition salt of a compound of claim 1.

14. A compound of claim 1 wherein $G_{12}$, $H_{13}$ and $I_{14}$ are absent.

15. A compound of claim 14 wherein at least one of the following occurs:
(i) $A_6$ is present and
 (A) $A_6$ is $XL_1$ or
 (B) $A_6$ is $XL_2$ and $XL_2$ is FTrp,
(ii) $B_7$ is present, $R_4$ of $B_7$ is other than hydrogen,
(iii) $C_8$ is $XL_1$, or
(iv) $B_7$ and $C_8$ both are present and $B_7$ is $XL_b$ wherein M is $CH_2$ and $C_8$ is $XL_1$.

16. A compound of claim 1 wherein $A_6$, $B_7$, $G_{12}$, $H_{13}$ and $I_{14}$ are absent and $E_{10}$–$F_{11}$ is $XL_6$.

17. A compound of claim 16 wherein $C_8$ is $XL_1$.

18. A compound of claim 1 wherein $A_6$, $B_7$, $C_8$, $H_{13}$ and $I_{14}$ are absent and $E_{10}$–$F_{11}$ is $XL_6$.

19. A compound of claim 1 wherein $A_6$, $B_7$, $H_{13}$ and $I_{14}$ are absent and $E_{10}$–$F_{11}$ is $XL_6$.

20. A compound of claim 5, wherein $A_6$, $B_7$, $G_{12}$, $H_{13}$ and $I_{14}$ are absent.

21. A compound of claim 20 selected from the group consisting of:
Boc-Phe-NMHis-LVA-IBA,
Boc-Phe-NMHis-LVA-MBA,
or a pharmaceutically acceptable salt thereof.

22. Boc-Phe-NMHis-LVA-MBA, a compound of claim 21.

23. A compound of claim 1 selected from the group consisting of:
Ac-Pro-Phe-NMHis-PRP-NH$_2$;
Boc-Pro-Phe-NMHis-LVA-Ile-AMP;
Ac-Pro-Phe-NMHis-LVA-Ile-AMP;
Boc-Phe-NMHis-LVA-Ile-AMP; and
Boc-Nall-NMHis-LVA-Ile-AMP.

24. A compound of claim 1 selected from the group consisting of:
DMA-Pro-Phe-NMHis-LVA-Ile-AMP;
TMA-Pro-Phe-NMHis-LVA-Ile-AMP;
Ac-FTrp-Pro-Phe-NMHis-Sta-NH$_2$;
Boc-Pro-Phe-NMHis-LVA-Ile-OH;
Boc-Pro-NMHis-LVA-Ile-AMP; and
H-Gly-Pro-Phe-NMHis-LVA-Ile-AMP.

25. A renin inhibitory peptide of claim 1
wherein $A_6$ is absent;
wherein $B_7$ is a divalent moiety of the formula $XL_b$;
wherein $C_8$ is a divalent moiety of the formula $XL_2$;
wherein $E_{10}$–$F_{11}$ is a divalent moiety of the formula $XL_6$,
wherein $G_{12}$ a divalent moiety of the formula $XL_{4a}$;
wherein $H_{13}$ and $I_{14}$ are absent; and
wherein Z is —N(CH$_2$)$_n$—R$_{18}$.

26. A compound of claim 25 wherein $R_4$ of —N(R-4)— in $D_9$ is methyl, $R_1$ and $R_{11}$ are isopropyl, $R_{18}$ is 2-pyridinyl, and n is 1.

27. Boc-Pro-Phe-NMHis-LVA-Ile-AMP, or its salts with citric or aspartic acid, compounds of claim 26.

28. Boc-Pro-Phe-NMHis-LVA-Ile-AMP, a compound of claim 27.

29. A method for treating or preventing hypertension in a mammal susceptible to or experiencing hypertension comprising the oral administration of an amount effective to treat or prevent hypertension of a pharmaceutically acceptable acid addition salt of a compound of claim 25.

* * * * *